US007671082B2

(12) United States Patent
Moher et al.

(10) Patent No.: US 7,671,082 B2
(45) Date of Patent: *Mar. 2, 2010

(54) PRODRUGS OF EXCITATORY AMINO ACIDS

(75) Inventors: Eric David Moher, Greenwood, IN (US); James Allen Monn, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/059,112

(22) Filed: Mar. 31, 2008

(65) Prior Publication Data
US 2008/0182889 A1 Jul. 31, 2008

Related U.S. Application Data

(63) Continuation of application No. 10/516,559, filed as application No. PCT/US03/15405 on Jun. 6, 2003, now Pat. No. 7,371,872.

(60) Provisional application No. 60/415,936, filed on Oct. 3, 2002, provisional application No. 60/415,937, filed on Oct. 3, 2002.

(30) Foreign Application Priority Data

Jun. 11, 2002 (EP) .................................. 02380120
Jun. 11, 2002 (EP) .................................. 02380121

(51) Int. Cl.
A01N 43/12 (2006.01)
A61K 31/38 (2006.01)
C07D 333/00 (2006.01)
C07D 409/02 (2006.01)

(52) U.S. Cl. ......................................... 514/443; 549/49
(58) Field of Classification Search ...................... None
See application file for complete search history.

(56) References Cited

U.S. PATENT DOCUMENTS

| | | | |
|---|---|---|---|
| 5,688,826 A | 11/1997 | Massey et al. | |
| 5,958,960 A | 9/1999 | Massey et al. | |
| 6,316,498 B1 | 11/2001 | Nakazato et al. | |
| 6,333,428 B1 | 12/2001 | Nakazato et al. | |
| 6,716,452 B1 | 4/2004 | Piccariello et al. | |
| 6,770,676 B2 | 8/2004 | Nakazato et al. | |
| 7,371,872 B2 * | 5/2008 | Moher et al. | ............ 549/53 |
| 2005/0192273 A1 * | 9/2005 | Johnson et al. | .......... 514/225.8 |

FOREIGN PATENT DOCUMENTS

| | | |
|---|---|---|
| EP | 1459765 | 9/2004 |
| WO | WO 93/06127 | 4/1993 |
| WO | WO 98/04277 | 2/1998 |
| WO | WO 99/38839 | 8/1999 |
| WO | WO 00/12464 | 3/2000 |
| WO | WO 02/00605 | 1/2002 |
| WO | WO 02/34237 | 5/2002 |
| WO | WO 02/055481 | 7/2002 |
| WO | WO 02/055485 | 7/2002 |
| WO | WO 03/061698 | 7/2003 |
| WO | WO 03/084610 | 10/2003 |
| WO | WO 03/104217 | 12/2003 |

OTHER PUBLICATIONS

"Amino acids, cyclic", http://www.nlm.nih.gov/cgi/mesh/2009/MB_cgi?mode=&term=Amino+Acids,+Cyclic& field=entry#TreeD12.125.072, accessed Feb. 19, 2009, attached as PDF.*
Hu, M., et al., "Use of the Peptide Carrier System to Improve the Intestinal Absorption of L- a -Methyldopa: Carrier Kinetics, Intestinal Permeabilities, and In Vitro Hydrolysis of Dipeptidyl Derivatives of L-a-Methyldopa," Pharmaceutical Research, vol. 6, No. 1 (1989).
Wang, H-P., et al., "Synthesis and Pharmacological Activities of a Novel Tripeptide Mimetic Dopamine Prodrug," Bioorganic & Medicinal Chemistry Letters, vol. 5, No. 19, pp. 2195-2198 (1995).
Yang, C., et al., "Prodrug based optimal drug delivery via membrane transporter/receptor," Exp. Opin. Biol. Ther; (2001)1(2):159-175.
Bradshaw, T., et al., "Preclinical evaluation of amino acid prodrugs of novel antitumor 2-(4-amino-3-methylphenyl)benzothiazoles," Molecular Cancer Therapeutics 1(4):239-246 (Feb. 2002).
Ohsumi, K., et al., "Synthesis and antitumor activities of amino acid prodrugs of amino-combretastatins," Anti-Cancer Drug Design 14:539-548 (1999).
Sanchez, J. et al., "Quinolone antibacterial agents. Synthesis and structure-activity relationships of a series of amino acid prodrugs of racemic and chiral 7-(3-amino-l-pyrrolidinylquinolines, highly soluble quinolone prodrug with in vivo pseudomonas activity," Journal of Medicinal Chemistry 35(10):1764-1773 (1992).
Yang, C.Y., et al., "Intestinal Peptide Transport Systems and Oral Drug Availability," Pharmaceutical Research, 16(9):1331-1343 (1999).
Meredith, D., et al., "Modified amino acids and peptides as substrates for the intestinal peptide transporter PepT1," Eur: J. Biochem, 267:3723-3728 (2000).
Sawada, K., et al., "Recognition of $_L$-Amino Acid Ester Compounds by Rat Peptide Transporters PEPT1 and PEPT2," The Journal of Pharmacology and Experimental Therapeutics, 291(2):705 (1999).
Han, H-K., et al., "Designing Prodrugs for the HPEPT1 Transporter," College of Pharmacy, The University of Michigan, p. 1259-260, 2000.
Dantzig, A.H., et al., "Uptake of the cephalosporin, cephalexin, by a dipeptide transport carrier in the human intestinal cell line, Caco-2." Biochimica et Biophysica Acta, 1027:211-217 (1990).
Han, H-K., "Targeted Prodrug Design to Optimize Drug Delivery," AAPS Pharmsci, 2(1) article 6 (2000).
Monn, et al., Synthesis and Metabotropic Glutamate Receptor Activity of S-Oxidized Variants of (-)-4-Amino-2-Thiabicyclo-[3.1.0]hexane-4,6-dicarboxylate: Identification of Potent, Selective, and Orally Bioavailable Agonists for mGlu2/3 Receptors. Journal of Medicinal Chemistry, 2007, 50, 233-240.

* cited by examiner

Primary Examiner—James O Wilson
Assistant Examiner—Noble Jarrell
(74) Attorney, Agent, or Firm—Danica Hostettler; Elizabeth A. McGraw

(57) ABSTRACT

This invention relates to synthetic excitatory amino acid prodrugs and processes for their preparation. The invention further relates to methods of using, and pharmaceutical compositions comprising, the compounds for the treatment of neurological disorders and psychiatric disorders.

15 Claims, No Drawings

PRODRUGS OF EXCITATORY AMINO ACIDS

This application is a continuation of U.S. patent application Ser. No. 10/516,559, filed Nov. 30, 2004, now U.S. Pat. No. 7,371,872 which is the national phase application, under 35 U.S.C. 371, for PCT/US03/15405 filed 6 Jun. 2003, which claims the priority of EP Application No. 02380120.2 filed 11 Jun. 2002, EP Application No. 02380121.0 filed 11 Jun. 2002, U.S. Provisional Application No. 60/415,936 filed 3 Oct. 2002, and U.S. Provisional Application No. 60/415,937 filed 3 Oct. 2002.

This invention provides synthetic excitatory amino acid prodrugs (compounds of Formula I) and processes for their preparation. The invention further relates to methods of using, and pharmaceutical compositions comprising, the compounds of Formula I for the treatment of neurological disorders and psychiatric disorders.

BACKGROUND OF THE INVENTION

Treatment of neurological or psychiatric disorders, such as anxiety disorders, have been linked to selective activation of metabotropic excitatory amino acid receptors. For example, (+)-4-amino-2-sulfonylbicyclo[3.1.0]hexane-4,6-dicarboxylic acid is disclosed as an active mGluR2 receptor agonist in U.S. Pat. No. 5,688,826 (the '826 patent), issued Nov. 18, 1997. Additionally, (+)-2-amino-4-fluorobicyclo[3.1.0]hexane-2,6-dicarboxylic acid is disclosed as an active mGluR2 receptor agonist in U.S. Pat. No. 5,958,960 (the '960 patent), issued Sep. 28, 1999.

The present invention provides for prodrug forms of mGluR2 receptor agonist compounds, which enhance the in vivo potency of the respective parent compound and produce higher oral exposure of the parent compound. Compounds of the present invention represent the best approach for maintaining the safety and efficacy of previously disclosed mGluR2 receptor agonists with increased oral bioavailability.

Synthetic excitatory amino acid prodrugs and processes for their preparation are disclosed in PCT Application Serial Nos. PCT/US01/45866 and PCT/US02/00488.

SUMMARY OF THE INVENTION

The present invention provides a compound of Formula I

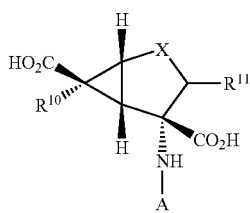

(I)

wherein
A is H-(Q)$_p$-;
Q is independently selected, each time taken, from the group amino acyl;
p is an integer from 1 to 10;
X is O, S, SO, SO$_2$, or CR$^3$R$^4$;
R$^3$ is fluoro, X'OR$^5$, SO$_3$H, tetrazol-5-yl, CN, PO$_3$R$^6{}_2$, hydroxy, or NO$_2$, and R$^4$ is hydrogen; or R$^3$ and R$^4$ each represent fluoro; or R$^3$ and R$^4$ together represent =O, =NOR$^7$, or =CR$^8$R$^9$; or one of R$^3$ or R$^4$ represents amino and the other represents carboxyl; or R$^3$ represents N$_3$, (CH$_2$)$_m$COOR$^{5a}$, (CH$_2$)$_m$PO$_3$R$^{6a}{}_2$, NHCONHR$^{5b}$, or NHSO$_2$R$^{5c}$, and R$^4$ represents hydrogen; or R$^3$ and R$^4$ together represent =CHCOOR$^{5b}$, =CHPO$_3$R$^{6a}{}_2$, or =CHCN;

X' represents a bond, CH$_2$, or CO;
m is an integer from 1 to 3;
R$^5$, R$^{5a}$, R$^{5b}$, R$^{5c}$, R$^7$, R$^8$, and R$^9$ are independently a hydrogen atom; an optionally substituted (1-6C) alkyl group; an optionally substituted (2-6C) alkenyl group; an optionally substituted (2-6C) alkynyl group; an optionally substituted aromatic group; an optionally substituted heteroaromatic group; a non-aromatic carbocyclic group; a non-aromatic heterocyclic group; a non-aromatic monocyclic carbocyclic group fused with one or two monocyclic aromatic or heteroaromatic groups; or a non-aromatic monocyclic heterocyclic group fused with one or two monocyclic aromatic or heteroaromatic groups;
R$^6$ and R$^{6a}$ independently represent hydrogen or a (1-6C) alkyl group;
R$^{10}$ is hydrogen or fluoro; and
R$^{11}$ is hydrogen, fluoro, or hydroxy;
or a pharmaceutically acceptable salt thereof.

The present invention also provides a compound of Formula I wherein substitutents are defined as above, provided that the compound is not one in which X is CR$^3$R$^4$ wherein R$^3$ is fluoro and R$^4$ is hydrogen, p is 1, and Q is L-alanyl; or a pharmaceutically acceptable salt thereof.

The present invention also provide a compound of Formula I wherein A is H-(Q)$_p$-; Q is independently selected, each time taken, from the group amino acyl; p is an integer from 1 to 3; X is O, S, SO, SO$_2$, or CR$^3$R$^4$; R$^3$ is fluoro or hydroxy, and R$^4$ is hydrogen; or R$^3$ and R$^4$ together represent =O; R$^{10}$ is hydrogen or fluoro; and R$^{11}$ is hydrogen, fluoro, or hydroxy; or a pharmaceutically acceptable salt thereof.

The present invention also provides a compound of Formula I wherein A is H-(Q)$_p$-; Q is L-alanyl; p is 1; X is CR$^3$R$^4$; R$^3$ is fluoro and R$^4$ is hydrogen; R$^{10}$ is hydrogen; and R$^{11}$ is hydrogen; or a pharmaceutically acceptable salt thereof.

It will be appreciated that the compounds of Formula I contain at least four asymmetric carbon atoms. The present invention includes all stereoisomeric forms of the compounds of Formula I, including each of the individual enantiomers and mixtures thereof such as prodrug forms of compounds disclosed in the '826 patent such as, for example, 1SR,4RS, 5RS,6RS-4-amino-(2-sulfonylbicyclo[3.1.0]hexane)-4,6-dicarboxylic acid.

A further aspect of the present invention provides for a pharmaceutical formulation comprising in association with a pharmaceutically acceptable carrier, dilutent, or excipient, a compound of Formula I, or a pharmaceutically acceptable salt thereof.

A further aspect of the present invention provides for a method for affecting the cAMP-linked metabotropic glutamate receptors in a patient, which comprises administering to a patient requiring modulated excitatory amino acid neurotransmission a pharmaceutically-effective amount of a compound of Formula I. This invention also provides for a use of a compound of Formula I for the manufacture of a medicament for affecting the cAMP-linked metabotropic glutamate receptors in a patient.

A further aspect of the present invention provides a method of administering an effective amount of a compound of Formula II that comprises administering to a patient requiring modulated excitatory amino acid neurotransmission a pharmaceutically effective amount of a compound of Formula I. This invention also provides for a use of a compound of Formula I for the manufacture of a medicament for administering an effective amount of a compound of Formula II.

A further aspect of the present invention provides for a method for treating a neurological disorder in a patient that comprises administering to the patient in need of treatment thereof a pharmaceutically-effective amount of a compound of Formula I. This invention also provides for a use of a compound of Formula I for the manufacture of a medicament for treating a neurological disorder in a patient.

A further aspect of the present invention provides for a method for treating a psychiatric disorder in a patient that comprises administering to the patient in need of treatment thereof a pharmaceutically-effective amount of a compound of Formula I. This invention also provides for a use of a compound of Formula I for the manufacture of a medicament for treating a psychiatric disorder in a patient.

Compounds of Formula I may be made by a process that is analogous to one known in the chemical art for the production of structurally analogous heterocyclic compounds or by a novel process described herein. Such processes and intermediates useful for the manufacture of a compound of Formula I as defined above are illustrated by the following procedures in which, unless otherwise specified, the meanings of the generic radicals are as defined herein.

The present invention provides a process for preparing compounds of Formula I comprising acylating a compound of formula (ii):

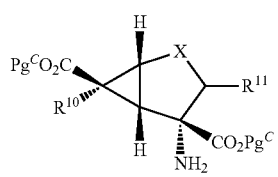

(ii)

with a corresponding amino acyl of Formula III

Pg$^N$-A- (III)

wherein Pg$^N$ is a nitrogen-protecting group and A is as defined above;

whereafter, for any of the above procedures, when a functional group is protected using a protecting group, removing the protecting group;

whereafter, for any of the above procedures: when a pharmaceutically acceptable salt of a compound of Formula I is required, reacting the basic form of such a compound of Formula I with an acid affording a pharmaceutically acceptable counterion; or for a compound of Formula I which bears an acidic moiety, reacting the acidic form of such a compound of Formula I with a base which affords a pharmaceutically acceptable cation; or for a zwitterionic compound of Formula I, neutralizing the acid-addition salt form or base-addition salt form of such a compound of Formula I; or by any other conventional procedure.

The present invention also provides for compounds of Formula I, wherein X is CH$^2$, R$^{10}$ is fluoro, and the other variables are as defined above.

DETAILED DESCRIPTION OF THE INVENTION

Compounds of the invention have been found to be useful prodrugs of compounds that are selective agonists of metabotropic glutamate receptors, and are therefore useful in the treatment of diseases of the central nervous system such as neurological diseases, for example neurodegenerative diseases, and as antipsychotic, anxiolytic, drug-withdrawal, antidepressant, anticonvulsant, analgesic and anti-emetic agents.

It will be appreciated that the compounds of Formula I contain at least four asymmetric carbon atoms, three being in the cyclopropane ring and one being at the α-carbon of the amino acid group. Accordingly, the compounds of the invention may exist in and be isolated in enantiomerically pure form, in racemic form, or in a diastereoisomeric mixture.

The amino acid moiety preferably has the natural amino acid configuration, i.e., the L-configuration relative to D-glycerol aldehyde.

The present invention includes pharmaceutically acceptable salts of a compound of Formula I. These salts can exist in conjunction with the acidic or basic portion of the molecule and can exist as acid addition, primary, secondary, tertiary, or quaternary ammonium, alkali metal, or alkaline earth metal salts. Generally, the acid addition salts may be prepared by the reaction of an acid with a compound of Formula I. Alternatively, acid addition salts may be prepared by reacting the penultimate compound (protected intermediate) with appropriate equivalents of acid to produce the corresponding salt form, which, in turn, may be reacted to produce a compound of Formula I or other salts. The alkali metal and alkaline earth metal salts are generally prepared by the reaction of the hydroxide form of the desired metal salt with a compound of Formula I.

Some particular salts provide certain formulation advantages due to their crystalline form. Non-crystalline amorphous forms of compounds may be hygroscopic. Crystalline forms of pharmaceutical compounds are sometimes more desirable because they exhibit favorable solid-state properties.

Acids commonly employed to form such salts include inorganic acids, for example hydrochloric, hydrobromic, nitric, sulphuric or phosphoric acids, or with organic acids, such as organic carboxylic acids, for example, glycolic, maleic, hydroxymaleic, fumaric, malic, tartaric, citric, salicyclic, o-acetoxybenzoic, or organic sulphonic, 2-hydroxyethane sulphonic, toluene-p-sulphonic, methane-sulfonic, naphthalene-2-sulphonic, benzene sulfonic, or ethane sulfonic acid.

In addition to pharmaceutically acceptable salts, other salts are included in the invention. They may serve as intermediates in the purification of compounds or in the preparation of other pharmaceutically acceptable acid addition salts, or are useful for identification, characterization, or purification.

In the present invention, compounds of Formula I include solvates thereof. Particularly, compounds of Formula I include hydrates thereof.

Furthermore, the present invention contemplates prodrugs of fluorinated compounds as disclosed in International Application Nos. PCT/JP99/03984, PCT/JP99/00324, and PCT/JP01/05550. See International Publication Nos. WO/0012464, WO/9938839, and WO/0200605, respectively. For example, the present invention contemplates prodrugs of 1S,2R,5S,6S-2-amino-6-fluoro-4-oxobicyclo[3.1.0]hexane-2,6-dicarboxylic acid; 1S,2R,4S,5S,6S-2-amino-6-fluoro-4-hydroxybicyclo[3.1.0]hexane-2,6-dicarboxylic acid; 1S,2R,3R,5S,6S-2-amino-3-fluorobicyclo[3.1.0]hexane-2,6-dicarboxylic acid; and 1S,2R,3S,5S,6S-2-amino-6-fluoro-3-hydroxybicyclo[3.1.0]hexane-2,6-dicarboxylic acid.

A variety of physiological functions have been shown to be subject to influence by excessive or inappropriate stimulation of excitatory amino acid transmission. The Formula I compounds of the present invention are believed to have the ability to treat a variety of neurological disorders in mammals associated with this condition, including acute neurological disorder such as cerebral deficits subsequent to cardiac bypass surgery and grafting, stroke, cerebral ischemia, spinal cord trauma, head trauma, perinatal hypoxia, cardiac arrest, and hypoglycemic neuronal damage. The Formula I compounds are believed to have the ability to treat a variety of chronic neurological disorders, such as Alzheimer's disease, Huntington's Chorea, amyotropic lateral sclerosis, AIDS-induced dementia, ocular damage and retinopathy, cognitive disorders, and idiopathic and drug-induced Parkinson's. The present invention also provides methods for treating these disorders which comprises administering to a patient in need thereof an effective amount of a compound of Formula I or a pharmaceutically acceptable salt thereof.

The Formula I compounds of the present invention treat a variety of other neurological disorders in patients that are associated with glutamate dysfunction, including muscular spasms, convulsions, migraine headaches, urinary incontinence, pain, premenstrual dysphoric disorder (PDD), psychosis, (such as schizophrenia), drug tolerance, withdrawal, cessation, and craving (such as nicotine, opiates, cocaine, benzodiazepines, and ethanol), anxiety and related disorders, emesis, brain edema, chronic pain, and tardive dyskinesia. The Formula I compounds are also useful as antidepressant and analgesic agents. Therefore, the present invention also provides methods for treating these disorders which comprise administering to a patient in need thereof an effective amount of a compound of Formula I, or a pharmaceutically acceptable salt thereof.

The following definitions are to set forth the meaning and scope of the various terms used herein. The general terms used herein have their usual meanings.

The term "affecting" refers to a Formula II compound acting as an agonist at an excitatory amino acid receptor. The term "excitatory amino acid receptor" refers to a metabotropic glutamate receptor, a receptor that is coupled to cellular effectors via GTP-binding proteins. The term "cAMP-linked metabotropic glutamate receptor" refers to a metabotropic receptor that is coupled to inhibition of adenylate cyclase activity.

The term "neurological disorder" refers to both acute and chronic neurodegenerative conditions, including cerebral deficits subsequent to cardiac bypass surgery and grafting, cerebral ischemia (for example stroke resulting from cardiac arrest), spinal cord trauma, head trauma, Alzheimer's Disease, Huntington's Chorea, amyotrophic lateral sclerosis, AIDS-induced dementia, perinatal hypoxia, hypoglycemic neuronal damage, ocular damage and retinopathy, cognitive disorders, idiopathic and drug-induced Parkinson's Disease. This term also includes other neurological conditions that are caused by glutamate dysfunction, including muscular spasms, migraine headaches, urinary incontinence, drug tolerance, withdrawal, cessation, and craving (i.e. opiates, benzodiazepines, nicotine, cocaine, or ethanol), smoking cessation, emesis, brain edema, chronic pain, sleep disorders, convulsions, Tourette's syndrome, attention deficit disorder, and tardive dyskinesia.

The term "psychiatric disorder" refers to both acute and chronic psychiatric conditions, including schizophrenia anxiety and related disorders (e.g. panic attack and stress-related cardiovascular disorders), depression, bipolar disorders, psychosis, obsessive compulsive disorders, generalized anxiety disorder, acute stress disorder, and panic disorder.

As used herein the term "effective amount" refers to the amount or dose of the compound, upon single or multiple dose administration to the patient, which provides the desired effect in the patient under diagnosis or treatment.

An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances. For example, a typical daily dose may contain from about 5 mg to about 300 mg of the active ingredient. The compounds can be administered by a variety of routes including oral, rectal, transdermal, subcutaneous, intravenous, intramuscular, bucal, or intranasal routes. Alternatively, the compound may be administered by continuous infusion.

As used herein the term "patient" refers to a mammal, such as a mouse, guinea pig, rat, dog or human. It is understood that the preferred patient is a human.

The term "treating" (or "treat") as used herein includes its generally accepted meaning which encompasses prohibiting, preventing, restraining, and slowing, stopping, or reversing progression of a resultant symptom. As such, the methods of this invention encompass both therapeutic and prophylactic administration.

The general chemical terms used herein have their usual meanings. For example, the term "(1-6C) alkyl" means a straight or branched group. Examples of values for a (1-6C) alkyl group include (1-4C) alkyl such as methyl, ethyl, propyl, isopropyl, butyl, and isobutyl. The term "(2-6C) alkenyl" includes (2-4C) alkenyl, such as allyl. The term "(2-6C) alkynyl" includes (2-4C) alkenyl, such as propynyl.

The term "optionally substituted," as used in the terms "optionally substituted (1-6C) alkyl group," "optionally substituted (2-6C) alkenyl group," and "optionally substituted (2-6C) alkynyl group," herein signifies that one or more substituents may be present, preferably one to three, said substituents being selected from atoms and groups which, when present in the compound of Formula I, do not prevent the compound of Formula I from modulating metabotropic glutamate receptor function.

Examples of atoms and groups which may be present in an optionally substituted (1-6C) alkyl group, an optionally substituted (2-6C) alkenyl group, or an optionally substituted (2-6C) alkynyl group are an optionally substituted aromatic group, an optionally substituted heteroaromatic group, a non-aromatic carbocyclic group, a non-aromatic heterocyclic group, a non-aromatic monocyclic carbocyclic group fused with one or two monocyclic aromatic or heteroaromatic groups and a non-aromatic monocyclic heterocyclic group fused with one or two monocyclic aromatic or heteroaromatic groups.

The term "heteroaromatic group" includes an aromatic 5-6 membered ring containing from one to four heteroatoms selected from oxygen, sulfur and nitrogen, and an aromatic bicyclic group consisting of a 5-6 membered ring containing from one to four heteroatoms selected from oxygen, sulfur and nitrogen fused with a benzene ring or a 5-6 membered ring containing from one to four heteroatoms selected from oxygen, sulfur and nitrogen. Examples of heteroaromatic groups are furyl, thiophenyl, oxazolyl, isoxazolyl, thiazoyl, isothiazolyl, imidazolyl, pyrimidyl, benzofuryl, benzothiophenyl, benzimidazolyl, benzoxazolyl, benzothiazolyl and indolyl.

The term "aromatic group" includes phenyl and a polycyclic aromatic carbocyclic ring such as naphthyl.

The term "optionally substituted," as used in the terms "optionally substituted heteroaromatic group" and "optionally substituted aromatic group," herein signifies that one or more substituents may be present, said substituents being selected from atoms and groups which, when present in the compound of Formula I, do not prevent the compound of Formula I from modulating metabotropic glutamate receptor function.

Examples of atoms and groups which may be present in an optionally substituted heteroaromatic or an optionally substituted aromatic group are amino, hydroxy, nitro, halogeno, (1-6C)alkyl, (1-6C)alkoxy, (1-6C)alkylthio, carboxy, (1-6C)alkoxycarbonyl, carbamoyl, (1-6C)alkanoylamino, (1-6C)alkylsulphonyl, (1-6C)alkylsulphonylamino, optionally substituted phenyl, phenoxy, phenylthio, phenylsulphonyl, phenylsulphonylamino, toluenesulphonylamino, (1-6C)fluoroalkyl and (1-6C)fluoroalkoxy. Examples of particular values are amino, hydroxy, fluoro, chloro, bromo, iodo, methyl, methoxy, methylthio, carboxy, acetylamino, methanesulphonyl, nitro, acetyl, phenoxy, phenylthio, phenylsulphonyl, methanesulphonylamino and trifluoromethyl.

Examples of values for an optionally substituted aromatic group are 1-naphthyl, 2-naphthyl, phenyl, 2-biphenyl, 3-biphenyl, 4-biphenyl, 2-hydroxyphenyl, 3-hydroxyphenyl, 4-hydroxyphenyl, 2-fluorophenyl, 3-fluorophenyl, 4-fluorophenyl, 2,4-difluorophenyl, 3,4-difluorophenyl, pentafluorophenyl, 2-chlorophenyl, 3-chlorophenyl, 4-chlorophenyl, 2,4-dichlorophenyl, 3,4-dichlorophenyl, 3-chloro-4-fluorophenyl, 3,5-dichlorophenyl, 2-bromophenyl, 3-bromophenyl, 4-bromophenyl, 2-methylphenyl, 3-methylphenyl, 4-methylphenyl, 2-methoxyphenyl, 3-methoxyphenyl, 4-methoxyphenyl, 2,3-dimethoxyphenyl, 2,5-dimethoxyphenyl, 3,4-dimethoxyphenyl, 3,5-dimethoxyphenyl, 2-trifluoromethylphenyl, 3-trifluoromethylphenyl, 4-trifluoromethylphenyl, 2-fluoro-3-trifluoromethylphenyl, 3-trifluoromethyl-4-fluorophenyl, 3-trifluoromethyl-5-fluorophenyl, 2-fluoro-5-trifluoromethylphenyl, 2-phenoxyphenyl, 3-phenoxyphenyl, 3-carboxyphenyl, and 4-carboxyphenyl.

The term "non-aromatic carbocyclic group" includes a monocyclic group, for example a (3-10C)cycloalkyl group, such as cyclopropyl, cyclobutyl, cyclopentyl, cyclohexyl, cycloheptyl, cyclooctyl, cyclononyl or cyclodecyl, and a fused polycyclic group such as 1-adamantyl or 2-adamantyl, 1-decalyl, 2-decalyl, 4a-decalyl, bicyclo[3,3,0]oct-1-yl, -2-yl or -3-yl, bicyclo[4,3,0]non-1-yl, -2-yl, -3-yl or -7-yl, bicyclo[5,3,0]dec-1-yl, -2-yl, -3-yl, -4-yl, -8-yl or -9-yl and bicyclo[3.3.1]non-1-yl, -2-yl, -3-yl or 9-yl.

The term "non-aromatic heterocyclic group" includes a 4 to 7 membered ring containing one or two heteroatoms selected from oxygen, sulphur and nitrogen, for example azetidin-1-yl or -2-yl, pyrrolidin-1-yl, -2-yl or -3-yl, piperidin-1-yl, -2-yl, -3-yl or -4-yl, hexahydroazepin-1-yl, -2-yl, -3-yl or -4-yl, oxetan-2-yl or -3-yl, tetrahydrofuran-2-yl or -3-yl, tetrahydropyran-2-yl, -3-yl or -4-yl, hexahydrooxepin-2-yl, -3-yl or -4-yl, thietan-2-yl or -3-yl, tetrahydrothiophen-2-yl or -3-yl, tetrahydrothiopyran-2-yl, -3-yl or -4-yl, hexahydrothiepin-2-yl, -3-yl or -4-yl, piperazin-1-yl or -2-yl, morpholin-1-yl, -2-yl or -3-yl, thiomorpholin-1-yl, -2-yl or -3-yl, tetrahydropyrimidin-1-yl, -2-yl, -4-yl or -5-yl, imidazolin-1-yl, -2-yl or -4-yl, imidazolidin-1-yl, -2-yl or -4-yl, oxazolin-2-yl, -3-yl, -4-yl or -5-yl, oxazolidin-2-yl, -3-yl, -4-yl or -5-yl, thiazolin-2-yl, -3-yl, -4-yl or -5-yl, or thiazolidin-2-yl, -3-yl, -4-yl or -5-yl.

The term "a non-aromatic monocyclic carbocyclic group fused with one or two monocyclic aromatic or heteroaromatic groups" includes a (3-10C)cycloalkyl group fused with a benzene ring or a an aromatic 5-6 membered ring containing from one to four heteroatoms selected from oxygen, sulfur and nitrogen, such as indanyl, 1,2,3,4-tetrahydronaphth-1-yl or -2-yl, 5,6,7,8-tetrahydroquinolin-5-yl -6-yl, -7-yl or 8-yl, 5,6,7,8-tetrahydroisoquinolin-5-yl, -6-yl, -7-yl or 8-yl, 4,5,6,7-tetrahydrobenzothiophen-4-yl, -5-yl, -6-yl or -7-yl, dibenzo[2,3,6,7]cycloheptan-1-yl or -4-yl, dibenzo[2,3,6,7]cyclohept-4-en-1-yl or -4-yl, or 9-fluorenyl.

The term "a non-aromatic monocyclic heterocyclic group fused with one or two monocyclic aromatic or heteroaromatic groups" includes a 4 to 7 membered ring containing one or two heteroatoms selected from oxygen, sulphur and nitrogen, fused with a benzene ring or a an aromatic 5-6 membered ring containing from one to four heteroatoms selected from oxygen, sulfur and nitrogen, such as 2,3-dihydrobenzopyran-2-yl, -3-yl or -4-yl, xanthen-9-yl, 1,2,3,4-tetrahydroquinolin-1-yl, -2-yl, -3-yl or -4-yl, 9,10-dihydroacridin-9-yl or -10-yl, 2,3-dihydrobenzothiopyran-2-yl, -3-yl or -4-yl, or dibenzothiopyran-4-yl.

The term "nitrogen-protecting group," as used herein and as represented by "$Pg^N$," refers to those groups intended to protect or block the nitrogen group against undesirable reactions during synthetic procedures. Choice of the suitable nitrogen-protecting group used will depend upon the conditions that will be employed in subsequent reaction steps wherein protection is required, as is well within the knowledge of one of ordinary skill in the art. Commonly used nitrogen-protecting groups are disclosed in T. W. Greene and P. G. M. Wuts, Protective Groups In Organic Synthesis, $3^{rd}$ Ed. (John Wiley & Sons, New York (1999)). A preferred nitrogen-protecting group is tert-butoxycarbonyl.

The term "carboxy-protecting group," as used herein and as represented by "$Pg^C$," refers to one of the ester derivatives of the carboxylic acid group commonly employed to block or protect the carboxylic acid group while reactions are carried out on other functional groups of the compound. Particular values include, for example, methyl, ethyl, tert-butyl, benzyl, methoxymethyl, trimethylsilyl, and the like. Further examples of such groups may be found in T. W. Greene and P. G. M. Wuts, Protecting Groups in Organic Synthesis, $3^{rd}$ Ed. (John Wiley & Sons, New York (1999)). Preferred carboxy-protecting group are methyl and ethyl. The ester is decomposed by using a conventional procedure which does not affect another portion of the molecule.

The term "hydroxyl protecting group" denotes group understood by one skilled in the organic chemical arts of the type described in Chapter 2 of Greene and Wuts. Representative hydroxyl protecting groups include, for example, ether groups, substituted ethyl ether groups, isopropyl ether groups, phenyl and substituted phenyl ether groups, benzyl and substituted benzyl ether groups, alkylsilyl ether groups, ester protecting groups, and the like. The species of hydroxyl protecting group employed is not critical so long as the derivatized hydroxyl group is stable to the conditions of subsequent reaction(s) on other positions of the intermediate molecule and can be selectively removed at the appropriate point without disrupting the remainder of the molecule including any other hydroxyl protecting group(s).

The term "amino acyl" means an amino acyl derived from an amino acid selected from the group consisting of natural and unnatural amino acids as defined herein. The natural amino acids may be neutral, positive or negative depending on the substituents in the side chain. "Neutral amino acid" means an amino acid containing uncharged side chain substituents. Exemplary neutral amino acids include alanine, valine, leucine, isoleucine, proline, phenylalanine, tryptophan, methionine, glycine, serine, threonine, cysteine, glutamine, and asparagine. "Positive amino acid" means an amino acid in which the side chain substituents are positively charged at physiological pH. Exemplary positive amino acids include lysine, arginine and histidine. "Negative amino acid" means an amino acid in which the side chain substituents bear a net negative charge at physiological pH. Exemplary negative amino acids include aspartic acid and glutamic acid. Preferred amino acids are α-amino acids. The most preferred amino acids are α-amino acids having L stereochemistry at the α-carbon. Exemplary natural α-amino acids are valine, isoleucine, proline, phenylalanine, tryptophan, methionine, glycine, serine, threonine, cysteine, tyrosine, asparagine, glutamine, lysine, arginine, histidine, aspartic acid and glutamic acid.

"Unnatural amino acid" means an amino acid for which there is no nucleic acid codon. Examples of unnatural amino acids include, for example, the D-isomers of the natural α-amino acids as indicated above; Aib (aminobutyric acid), βAib (3-aminoisobutyric acid), Nva (norvaline), β-Ala, Aad (2-aminoadipic acid), βAad (3-aminoadipic acid), Abu (2-aminobutyric acid), Gaba (γ-aminobutyric acid), Acp (6-aminocaproic acid), Dbu (2,4-diaminobutryic acid), α-aminopimelic acid, TMSA (trimethylsilyl-Ala), alle (allo-isoleucine), Nle (norleucine), tert-Leu, Cit (citrulline), Orn, Dpm (2,2'-diaminopimelic acid), Dpr (2,3-diaminopropionic acid), α- or β-Nal, Cha (cyclohexyl-Ala), hydroxyproline, Sar (sarcosine), O-methyl tyrosine, phenyl glycine and the like; cyclic amino acids; $N^\alpha$-alkylated amino acids where $N^\alpha$-alkylated amino acid is $N^\alpha$-(1-10C)alkyl amino acid such as MeGly ($N^\alpha$-methylglycine), EtGly ($N^\alpha$-ethylglycine) and EtAsn ($N^\alpha$-ethylasparagine) and amino acids in which the α-carbon bears two side-chain substituents. Exemplary unnatural α-amino acids include D-alanine, D-leucine and phenylglycine. The names of natural and unnatural amino acids and residues thereof used herein follow the naming conventions suggested by the IUPAC-IUB Joint Commission on Biochemical Nomenclature (JCBN) as set out in "Nomenclature and Symbolism for Amino Acids and Peptides (Recommendations, 1983)" European Journal of Biochemistry, 138, 9-37 (1984). To the extent that the names and abbreviations of amino acids and residues thereof employed in this specification and appended claims differ from those noted, differing names and abbreviations will be made clear.

Although all of the compounds of Formula I are useful active mGluR2 receptor agonists, certain compounds are preferred. The following paragraphs define preferred classes.
A) Q is glycyl, alanyl, valyl, leucyl, isoleucyl, propyl, phenylalanyl, tyrosyl, tryptophyl, methionyl, lysyl, or serinyl.
B) Q is alanyl.
C) Q is methionyl.
D) p is 1.
E) p is 2.
F) X is $SO_2$.
G) X is $CR^3R^4$.
H) $R^3$ is fluoro and $R^4$ is hydrogen.
I) $R^3$ is hydroxy and $R^4$ is hydrogen.
J) $R^3$ and $R^4$ together represent =O.
K) $R^{10}$ is hydrogen.
L) $R^{10}$ is fluoro.
M) $R^{11}$ is hydrogen.
N) The compound is a free base.
O) The compound is a salt.
P) The compound is the hydrochloride salt.
Q) The compound is the mesylate salt.
R) The compound is the esylate salt.
S) The compound is the tosylate salt.

The preceding paragraphs may be combined to define additional preferred classes of compounds.

The compounds of Formula I are useful for the treatment of disorders of mammals, and the preferred mammal is a human.

The compounds of the present invention can be prepared by a variety of procedures, some of which are illustrated in the schemes below. The particular order of steps required to produce the compounds of Formula I is dependent upon the particular compound being synthesized, the starting compound, and the relative liability of the substituted moieties. Some substituents may have been eliminated in the following schemes for the sake of clarity, and are not intended to limit the teaching of the schemes in any way. As one of ordinary skill in the art will appreciate, substituents $R^{15}$ and $R^{16}$ represent the appropriate side chain to form the desired amino acyl.

If not commercially available, the necessary starting materials for the following schemes may be made by procedures which are selected from standard techniques of organic and heterocyclic chemistry, techniques which analogous to the syntheses of known, structurally similar compounds, and the procedures described in the preparations and examples, including novel procedures.

Scheme 1

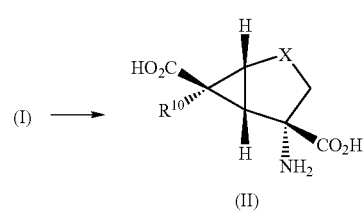

Compounds of Formula I are converted via enzymatic or hydrolytic process in vivo to form compounds of Formula II, as shown in Scheme 1 above. In particular, a crystalline form of a compound of Formula I may be prepared according to the route outlined in Scheme 2 below.

Scheme 2

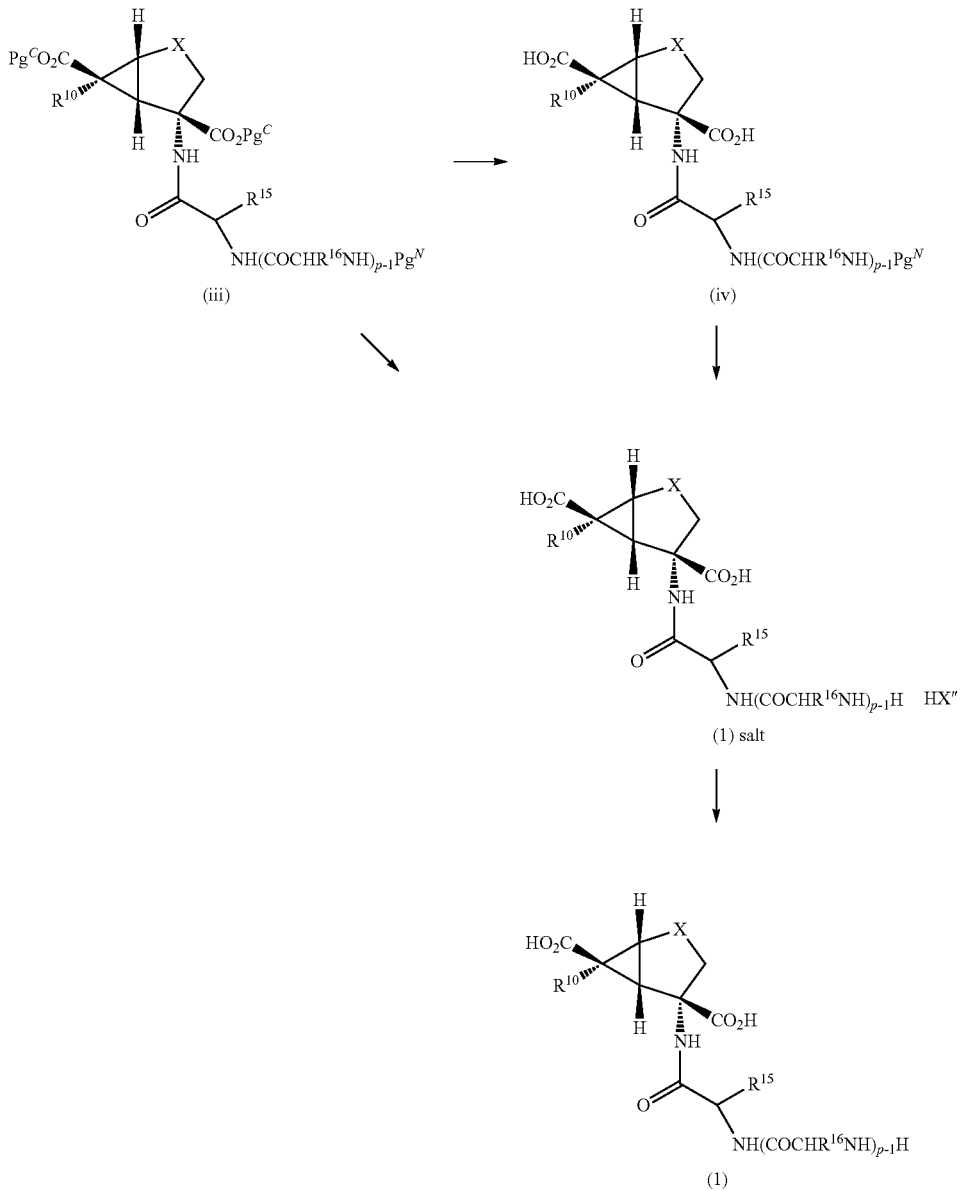

The hydrolysis of the di-ester protected peptidyl compound of formula (iii) with a suitable base such as lithium hydroxide or sodium hydroxide in a suitable solvent, such as THF or THF/water, affords the di-acid protected peptidyl compound of formula (iv). A compound of formula (iv) may be deprotected with a suitable acid in a suitable solvent. Such conditions may produce the corresponding acid salt of the di-acid peptidyl compound, depicted in Formula I salt, as an amorphous solid or, directly, a crystalline solid, wherein X" represents the corresponding anion. In the case of an amorphous solid, subsequent crystallization may occur from suitable solvents. Carboxylate salts may be formed by the introduction of a cationic species by a reagent such as sodium acetate. Finally, the zwitterionic compound may be afforded by treatment of the crystalline salt compound with an appropriate base.

For example, a di-acid protected peptidyl compound of formula (iv) when treated hydrogen chloride gas in suitable solvent provides the deprotected hydrochloride salt as an amorphous solid. The amorphous hydrochloride compound may then be crystallized from acetone and water to afford the crystalline hydrochloride salt compound. In the case of a crystalline solid which is formed directly, filtration of the reaction mixture may afford the crystalline salt. The zwitterionic compound is afforded by treatment of the crystalline hydrochloride salt compound with sodium hydroxide; alternatively, treatment of the mesylate salt compound or the tosylate salt compound with sodium hydroxide will also afford the zwitterionic compound. It will be appreciated by one of ordinary skill in the art that a compound of Formula I may be prepared in one procedure where the indicated intermediates are not isolated.

Scheme 3

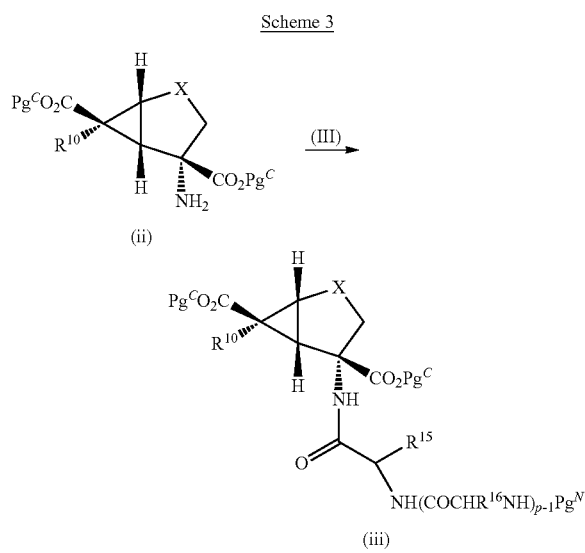

The di-ester of formula (ii) is acylated with a compound of Formula III using a suitable coupling agent to afford a di-ester protected peptidyl compound of formula (iii). Alternatively, this transformation could be achieved using the acid chloride of a compound of Formula III.

Suitable peptide coupling reagents include dicyclohexylcarbodiimide (DCC), 1-(3-dimethylaminopropyl)-3-ethylcarbodiimide (EDC), isobutyl chloroformate, diphenyl chlorophosphate, 2-chloro-4,6-dimethoxy-1,3,5-triazine (CDMT), bis(2-oxo-3-oxazolidinyl)phosphinic chloride, and benzotriazol-1-yloxytris(dimethylamino)phosphonium hexafluorophosphate.

Scheme 4

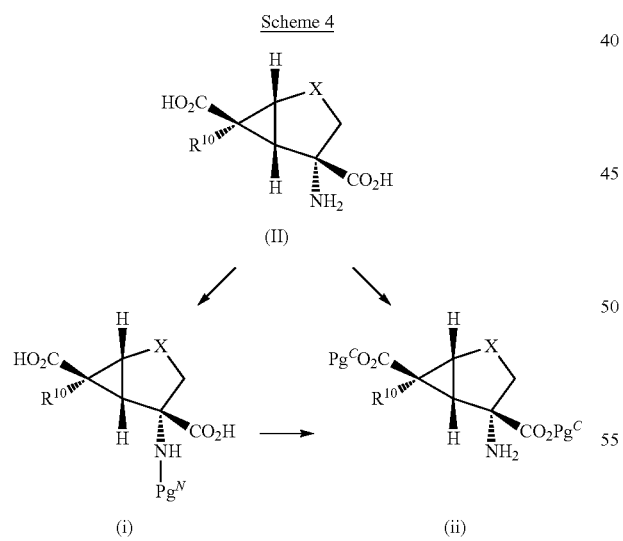

In Scheme 4 above, a compound of Formula II, a di-acid, is treated with a suitable carboxy-protecting agent, such as catalytic hydrochloric acid or thionyl chloride and methanol or ethanol, affording the corresponding di-ester of formula (ii). Alternatively, a compound of Formula II first may be treated with a nitrogen-protecting agent such as $BOC_2O$ to afford a nitrogen-protected compound of formula (i). Next, a compound of formula (i) may be treated with a carboxy-protecting agent such as methyl iodide in the presence of a base such as potassium carbonate, followed then by an nitrogen deprotecting agent such as hydrochloric acid or trifluoroacetic acid to afford a compound of formula (ii).

Additionally, one of ordinary skill in the art would recognize that depending on X, an appropriate protecting agent may be necessary. For example, if X represents $CR^3R^4$, $R^3$ represents hydroxy, and $R^4$ represents hydrogen, then one of ordinary skill in the art would appreciate that a suitable hydroxyl protecting group may be necessary before proceeding with any of the above schemes.

Compounds of Formula II are known in the art. For example, preparations of these compounds may be found in U.S. Pat. No. 5,688,826 (the '826 patent) and U.S. Pat. No. 5,958,960 (the '960 patent).

Various improvements upon the synthetic route to compounds of Formula II have been made over the processes previously disclosed. The improvements involve sulfur and alcohol oxidation, as well as optical resolution of various intermediates as described below.

The first improvement relates to the conversion described in the '826 patent at column 8, lines 22-34, and column 7, beginning at column 33 (Formula V), involving oxidation of a compound of Formula VII of the '826 patent Formula (VII) of the '826 patent

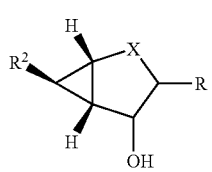

to form a compound of Formula V of the '826 patent

Formula (V) of the '826 patent

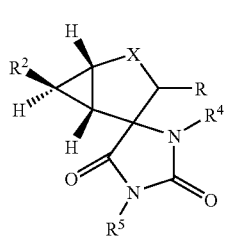

It has been discovered that the sulfur trioxide-pyridine complex or trifluoroacetic anhydride in conjunction with DMSO are preferred of the many oxidation methods known in the art.

Second, with respect to the resolution of a compound of Formula III of the '826 patent Formula (III) of the '826 patent in which $R^2$ represents a carboxyl group, referred to in column 8, at lines 3-7, and column 6, beginning at line 1 (Formula III), it has been discovered that (R)-α-methylbenzylamine and quinine are preferred. (R)-α-methylbenzylamine is particularly preferred.

Further, it has been discovered that when oxidizing the sulfide of a compound of Formula III of the '826 patent where X is sulfur to form a compound of Formula III of the '826 patent where X is sulfonyl, as referred to in the '826 patent at column 8, lines 39-53, that a basic aqueous system and hydrogen peroxide used in combination with a catalyst are preferred.

The following Examples further illustrate the compounds of the present invention and the methods for their synthesis. The Examples are not intended to be limiting to the scope of the invention in any respect, and should not be so construed. All experiments are run under a positive pressure of dry nitrogen or argon. All solvents and reagents are purchased from commercial sources and used as received, unless otherwise indicated. Dry tetrahydrofuran (THF) may be obtained by distillation from sodium or sodium benzophenone ketyl prior to use. Proton nuclear magnetic resonance ($^1$H NMR) spectra are obtained on a Bruker Avance II bay-500 at 500 MHz, a Bruker Avance I bay-200 at 200 MHz, or a Varian Inova/Varian 300/Varian 400 at 500 MHz. Electrospray mass spectroscopy (ESI) is performed on a Agilent MSD/B instrument using acetonitrile/aqueous ammonium acetate as the mobile phase. Free atom bombardment mass spectroscopy (FABMS) is performed on a VG ZAB-2SE instrument. Field desorption mass spectroscopy (FDMS) is performed using either a VG 70SE or a Varian MAT 731 instrument. Optical rotations are measured with a Perkin-Elmer 241 polarimeter. Chromatographic separation on a Waters Prep 500 LC is generally carried out using a linear gradient of the solvents indicated in the text. The reactions are generally monitored for completion using thin layer chromatography (TLC). Thin layer chromatography is performed using E. Merck Kieselgel 60 $F_{254}$ plates, 5 cm×10 cm, 0.25 mm thickness. Spots are detected using a combination of UV and chemical detection (plates dipped in a ceric ammonium molybdate solution [75 g of ammonium molybdate and 4 g of cerium (IV) sulfate in 500 mL of 10% aqueous sulfuric acid] and then heated on a hot plate). Flash chromatography is performed as described by Still, et al. Still, Kahn, and Mitra, *J. Org. Chem.*, 43, 2923 (1978). Elemental analyses for carbon, hydrogen, and nitrogen are determined on a Control Equipment Corporation 440 Elemental Analyzer or are performed by the Universidad Complutense Analytical Centre (Facultad de Farnacia, Madrid, Spain). Melting points are determined in open glass capillaries on a Gallenkamp hot air bath melting point apparatus or a Büchi melting point apparatus, and are uncorrected.

The abbreviations, symbols and terms used in the examples have the following meanings.

Ac=acetyl
Anal.=elemental analysis
ATR=attenuated total internal reflection
Bn or Bzl=benzyl
Bu=butyl
BOC=t-butoxycarbonyl
calcd=calculated
$D_2O$=deuterium oxide
DCC=dicyclohexylcarbodiimide
DCM=1,2-dichloromethane
DIBAL-H=diisobutyl aluminum hydride
DMAP=4-dimethylaminopyridine
DMF=dimethylformamide
DMSO=dimethylsulfoxide
DSC=differential scanning calorimetry
EDC=N-ethyl-N'N'-dimethylaminopropyl carbodiimide hydrochloride
ES=Electrospray
Et=ethyl
EtOH=ethanol
FAB=Fast Atom Bombardment (Mass Spectrascopy)
FDMS=field desorption mass spectrum
FTIR=Fourier transform infrared spectrometry
HOAt=1-hydroxy-7-azabenzotriazole
HOBt=1-hydroxybenzotriazole
HPLC=High Performance Liquid Chromatography
HRMS=high resolution mass spectrum
i-PrOH=isopropanol
IR=Infrared Spectrum
L=liter
Me=methyl
MeOH=methanol
MPLC=Medium Pressure Liquid Chromatography
Mp=melting point
MTBE=t-butyl methyl ether
NBS=N-bromosuccinimide
NMR=Nuclear Magnetic Resonance
PC-TLC=preparative centrifugal thin layer chromatography
Ph=phenyl
p.o.=oral administration
i-Pr=isopropyl
Rochelle's Salt=potassium sodium tartrate
rt=room temperature
SM=starting material
TBS=tert-butyldimethylsilyl
TEA=triethylamine
Temp.=temperature
TFA=trifluoroacetic acid
THF=tetrahydrofuran
TLC=thin layer chromatography
t-BOC=tert-butoxycarbonyl General Procedure A EDC Coupling Between Amines and N-BOC-(L)-Aminoacids Suspend the starting amino dialkyl ester (a compound of formula ii, Scheme 3) (1.0 equiv.) in dry dichloromethane under nitrogen. Sequentially add the corresponding N-Boc-(L)-aminoacid (1.5-2.0 equiv), EDC (1.5-2.0 equiv), HOBt (1.5-2.0 equiv), and dimethylaminopyridine (DMAP, 0.1-0.2 equiv). Stir the reaction mixture at room temperature until judged complete by TLC unless otherwise noted. Dilute the reaction mixture with ethyl acetate and wash sequentially with saturated aqueous $NaHCO_3$ and/or aqueous $NaHSO_4$, and brine. After drying over sodium sulfate and evaporation in vacuo purify the crude residue (a compound of formula iii) by silica gel chromatography using the appropriate eluent (typically ethyl acetate/hexanes).

General Procedure B

Anhydride Coupling Between Amine and N-BOC-(L)-Aminoacid Isobutyl Anhydrides

To a solution of the corresponding N-Boc-(L)-aminoacid (1.5 equiv) in dry dichloromethane (10 mL) at −20° C. under nitrogen add N-methyl morpholine (NMM, 1.5 equiv, in 1 mL $CH_2Cl_2$) followed by dropwise addition of iso-butyl chloroformate (IBCF, 1.5 equiv, in 5 mL $CH_2Cl_2$) at a rate so the internal reaction temperature does not exceed −15° C. Stir the resulting reaction mixture at −20° C. for 30 minutes then add a −20° C. solution of (1S,2S,4S,5R,6R)-2-(2'-amino-propionylamino)-4-hydroxy-bicyclo[3.1.0]hexane-2,6-dicarboxylic acid diethyl ester hydrochloride (1.0 equiv) in dichloromethane (10 mL) at a rate so the internal reaction temperature does not exceed −15° C. Upon complete addition, remove the cooling bath and stir the reaction mixture at room temperature until judged complete by TLC. Dilute the reaction mixture with ethyl acetate and sequentially wash with saturated aqueous $NaHCO_3$, aqueous $NaHSO_4$, and brine. After drying over magnesium sulfate and evaporation in vacuo purify the crude residue by silica gel chromatography using the appropriate eluent (typically hexanes/ethyl acetate).

General Procedure C

Sequential N-Boc and Ester Protecting Group Removal

Stir the corresponding N-Boc diester peptide derivative (a compound of formula iii, Scheme 2) (1.0 equiv) in a 1:1 mixture of THF/2.5 N LiOH (10-20 equiv) at room temperature for up to 4 hours. Dilute the reaction with $H_2O$ and wash with ethyl acetate. Discard the organic layer. Adjust the aqueous phase to pH 2 with 1 N HCl (NaCl added to aqueous phase to enhance extractability as needed) and exhaustively extract the N-boc dicarboxylic acid product (a compound of formula iv) with ethyl acetate. Combine all organics, wash with brine, dry over $MgSO_4$, and concentrate to dryness in vacuo to afford the desired carboxylate product as a foamy solid. Dissolve in ethyl acetate and chill to 0° C. Purge the reaction mixture with anhydrous HCl gas until saturated with HCl. Stir the resulting reaction mixture at 0° C. for up to 4 hours. Isolate the fully deprotected peptide derivative (a compound of Formula I) as its hydrochloride salt by filtration under $N_2$ or by concentration of the reaction mixture to dryness followed by trituration with ethyl acetate or $Et_2O$ and concentration to a white powder. Optionally, to remove residual solvent and excess HCl, reconstitution of the products in $H_2O$, freezing, and subsequent lyophilization afford the desired hydrochloride products.

Preparation 1

(1R,4S,5S,6S)-4-Amino-2,2-dioxo-2$\lambda^6$-thia-bicyclo [3.1.0]hexane-4,6-dicarboxylic acid diethyl ester

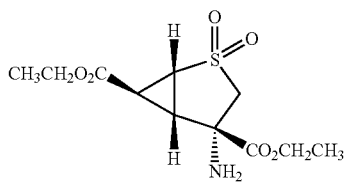

To a slurry of (1R,4S,5S,6S)-4-Amino-2,2-dioxo-2$\lambda^6$-thia-bicyclo[3.1.0]hexane-4,6-dicarboxylic acid (10 g, 42.5 mmol, U.S. Pat. No. 5,688,826) in 100 mL of 2B ethanol at room temperature is added thionyl chloride (15.5 mL, 212.6 mmol) dropwise over 20 minutes followed by rinsing with 40 mL of ethanol. Heat the slurry to reflux and stir overnight. Analysis via 500 MHz $^1$H NMR ($CD_3OD$) of a concentrated aliquot reveals complete consumption of starting material and intermediate monoester. Allow the resultant solution to cool to room temperature, then concentrate to a gelatinous residue.

Add EtOAc (50 mL) to the gelatin that was further concentrated to a solid, then dilute with another 94 mL of EtOAc. Add 15% aqueous sodium carbonate (70 mL) slowly to the mixture with swirling by hand to gradually afford dissolution, giving a final pH of 7.95. Filter the resulting sodium carbonate precipitation before extracting the layers. Back extract the aqueous layer with EtOAc (2×100 mL). Wash the combined organic extracts with brine (1×100 mL), dry ($MgSO_4$), filter, and concentrate it vacuo to provide a faint yellow oil that solidified to give the title compound as an off-white solid (11.71 g, 95% yield).

Recrystallization

A mixture of the title compound (200 mg) in EtOAc (800 μL) is heated to 56° C. at which time dissolution occurs. After stirring for 15 minutes at 56° C., heptane (1 mL) is added dropwise to the solution. The heat is tuned off. Allow the solution to cool to 52° C. at which time precipitation occurs. Upon cooling and further dilution with heptane (600 μL), the slurry forms. Stir the resultant slurry at room temperature for 1 hour before filtering, washing with heptane (2×500 μL), and drying at 45° C. overnight to give 145 mg (73% recovery) of the title compound as a white solid.

mp 80-83° C.

$[\alpha]^{25}_D$ −57.7° (c 1.04, $CH_3OH$).

500 MHz $^1$H NMR ($CD_3Cl_3$) δ 4.31 (q, 2H, J=7.0 Hz), 4.20 (m, 2H), 3.78 (d, 1H, J=15.0 Hz), 3.36 (dd, 1H, J=4.0, 7.0 Hz), 2.93 (dd, 1H, J=4.0, 7.0 Hz), 2.81 (d, 1H, J=15.0 Hz), 2.46 (t, 1H, J=4.0), 1.34 (t, 3H, J=7.0), 1.30 (t, 3H, J=7.0).

$^{13}$C NMR (125 MHz, $CD_3Cl_3$) δ 171.68, 168.57, 63.26, 62.42, 59.96, 56.06, 43.78, 32.25, 22.49, 14.31, 14.25.

FTIR (ATR) 3364.15 (s), 1725.95 (s), 1304.91 (s), 1259.24 (s), 1200.84 (s), 1104.91 (s), 1022.99 (s), 896.45 (s), 851.21 (s) cm$^{-1}$.

Anal. Cald for $C_{11}H_{17}NO_6S$: C, 45.35; H, 5.88; N, 4.81. Found: C, 45.02; H, 5.75; N, 4.82.

Preparation 2

(1R,4S,5S,6S)-4-(2'S-tert-butoxycarbonylaminopropionylamino)-2,2-dioxo-2$\lambda^6$-thia-bicyclo[3.1.0] hexane-4,6-dicarboxylic acid diethyl ester

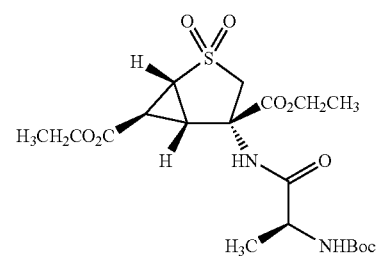

To a solution of N-Boc-L-alanine (43.52 g, 230 mmol) and N-methyl morpholine (25.5 mL, 232 mmol) in 457 mL of methylene chloride at −30° C. under nitrogen add iso-butyl chloroformate (30.4 mL, 234 mmol) dropwise over 10 minutes. Stir the resultant thin slurry at −25 to −30° C. for 30 min at which time a solution of (1R,4S,5S,6S)-4-amino-2,2-dioxo-2$\lambda^6$-thia-bicyclo[3.1.0]hexane-4,6-dicarboxylic acid diethyl ester (63.90 g, 219 mmol, Preparation 1) in 213 mL of methylene chloride is added over 25 minutes such that the reaction temperature does not exceed −25° C. Upon completion of the addition, remove the cooling bath and allow to stir at ambient temperature for 60 minutes at which time the reaction temperature reached 19° C. and the color became faint orange. Treat the reaction with 350 mL of 1 N HCl and separate the layers. Wash the organic layer with saturated aqueous NaHCO$_3$ (1×350 mL) and brine (1×350 mL), dry (Na$_2$SO$_4$), filter, and concentrate in vacuo to a white foam (105.2 g, 104%).

$^1$H NMR (300 MHz, CDCl$_3$) δ: 7.62 (brs, 1H), 4.90 (brd, 1H, J=7.1 Hz), 4.34-4.10 (m, 6H), 3.39 (ddd, 1H, J=7.2, 3.9, 1.0 Hz), 3.00 (dd, 1H, J=7.1, 3.9 Hz), 2.90 (brd, 1H, J=14.9 Hz), 2.43 (t, 1H, J=4.1 Hz), 1.46 (s, 9H), 1.31 (m, 9H).

$^{13}$C NMR (75 MHz, CDCl$_3$) δ: 173.0, 168.6, 167.6, 80.9, 76.5, 63.3, 62.3, 59.9, 55.7, 42.8, 31.5, 28.2, 22.7, 16.6, 14.0, 13.9. MS (ES) m/z 461.0 [M−H]$^-$.

Preparation 3

(1R,4S,5S,6S)-4-(2'S-tert-butoxycarbonylamino-propionylamino)-2,2-dioxo-2λ$^6$-thia-bicyclo[3.1.0]hexane-4,6-dicarboxylic acid

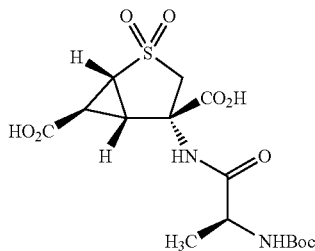

To a solution of (1R,4S,5S,6S)-4-(2'S-tert-butoxycarbonyl-lamino-propionylamino)-2,2-dioxo-2λ$^6$-thia-bicyclo[3.1.0]hexane-4,6-dicarboxylic acid diethyl ester (181.4 g, 392 mmol theoretical, Preparation 2) in 292 mL of THF at room temperature add 490 mL (980 mmol) of 2N sodium hydroxide. Allow the biphasic mixture to stir vigorously at room temperature for 1.25 hours at which time the reaction is homogeneous. Dilute the mixture with 490 mL of ethyl acetate and separate the layers. Dilute the aqueous layer with 490 mL of ethyl acetate, and lower the pH of the mixture to 1.5 with concentrated HCl. Separate the layers and back-extract the aqueous layer with 245 mL of ethyl acetate. Dry the combined organic layers (Na$_2$SO$_4$), filter, and concentrate to provide 167.9 g (105%) of the title compound as a white foam. This material was used without characterization in Examples 1 and 2.

Preparation 4

(1R,4S,5S,6S)-4-Amino-2,2-dioxo-2λ$^6$-thia-bicyclo[3.1.0]hexane-4,6-dicarboxylic acid dimethyl ester

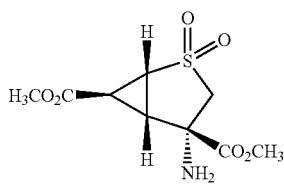

Add thionyl chloride (6.2 mL, 85.0 mmol) dropwise to a rapidly stirred suspension of (1R,4S,5S,6S)-4-Amino-2,2-dioxo-2λ$^6$-thia-bicyclo[3.1.0]hexane-4,6-dicarboxylic acid (10.0 g, 42.5 mmol, U.S. Pat. No. 5,688,826) in MeOH (170 mL, 5° C.). Upon complete addition, allow the reaction mixture to warm slowly to room temperature, then warm under reflux for 48 h. Remove the volatiles under reduced pressure, and partition the residue between a saturated solution of NaHCO$_3$ (200 mL) and ethyl acetate (400 mL). Separate the layers and extract the aqueous one with ethyl acetate (2×400 mL each time). Dry the combined organic layers over K$_2$CO$_3$, and concentrate under reduced pressure to afford 8.10 g (30.8 mmol) of the title compound in 72% yield.

$[\alpha]_D^{23}$=−84° (c=0.5, MeOH).

Anal Calcd for C$_9$H$_{13}$NO$_6$S: C, 41.06; H, 4.98; N, 5.32. Found: C, 40.94; H, 4.93; N, 5.30.

MS (ES) m/z 264.0 [M+H]$^+$.

Preparation 5

(1R,4S,5S,6S)-4-(2'S-tert-Butoxycarbonylamino-3'-phenyl-propionylamino)-2,2-dioxo-2λ$^6$-thia-bicyclo[3.1.0]hexane-4,6-dicarboxylic acid dimethyl ester

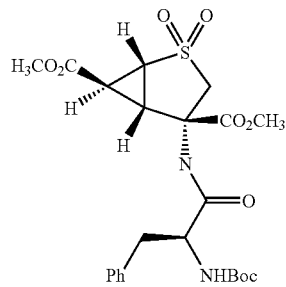

Prepare according to General Procedure A using commercially available N-BOC-(L)-Phenylalanine and (1R,4S,5S,6S)-4-Amino-2,2-dioxo-2λ$^6$-thia-bicyclo[3.1.0]hexane-4,6-dicarboxylic acid dimethyl ester (Preparation 4). Reflux reaction mixture overnight. Purify by PC-TLC, 4 mm SiO$_2$ rotor, (10% ethyl acetate/hexanes to 100% ethyl acetate). Yield 0.85 g (88%, 1.67 mmol) of a white foam.

$[\alpha]_D^{23}$=−35.2° (c=0.45, CHCl$_3$).

$^1$H NMR (300 MHz, CDCl$_3$) δ 1.43 (9H, s), 2.38-2.40 (1H, m), 2.86 (1H, d, J=15.0 Hz), 2.91 (1H, dd, J=4.4, 7.3 Hz), 3.04 (2H, d, J=7.3 Hz), 3.35-3.39 (1H, m), 3.77 (3H, s), 3.84 (3H, s), 4.11 (1H, d, J=14.3), 4.30 (1H, app. q, J=7.3), 4.96 (1H, bd, J=6.6 Hz), 6.96 (1H, bs), 7.22-7.36 (5H, m).

Anal Calcd for C$_{23}$H$_{30}$N$_2$O$_9$S.0.1H$_2$O: C, 53.92; H, 5.94; N, 5.47. Found: C, 53.62; H, 5.90; N, 5.28.

MS (ES) m/z 509.16 [M−H]$^-$; 411.2 [M-Boc]$^+$.

Preparation 6

(1R,4S,5S,6S)-4-(2'S-tert-Butoxycarbonylamino-3'S-methyl-pentanoylamino)-2,2-dioxo-2λ$^6$-thia-bicyclo[3.1.0]hexane-4,6-dicarboxylic acid dimethyl ester

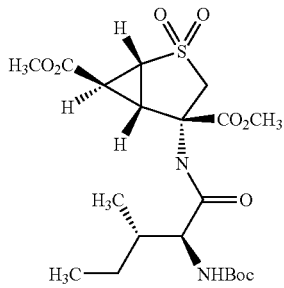

Prepare according to General Procedure A using commercially available N-BOC-(L)-Isoleucine and (1R,4S,5S,6S)-4-Amino-2,2-dioxo-2λ$^6$-thia-bicyclo[3.1.0]hexane-4,6-dicarboxylic acid dimethyl ester (Preparation 4). Reflux reaction mixture overnight. Purify by PC-TLC, 4 mm SiO$_2$ rotor, (10% ethyl acetate/hexanes to 100% ethyl acetate). Yield 0.75 g (83%, 1.57 mmol) of a white foam.

$[\alpha]_D^{23}$=−32.65° (c=0.49, CHCl$_3$).

$^1$H NMR (300 MHz, CDCl$_3$) δ 0.91 (3H, t, J=7.3 Hz), 0.93 (3H, d, J=6.6 Hz), 1.10-1.18 (1H, m), 1.46 (9H, s), 1.42-1.52 (1H, m), 1.81-1.86 (1H, bm), 2.51 (1H, t, J=4.0 Hz), 2.95 (1H, d, J=15.0 Hz), 3.06 (1H, dd, J=4.4, 7.3 Hz), 3.43 (3H, dd, J=3.7, 7.0 Hz), 3.78 (3H, s), 3.85 (3H, s), 3.82-3.90 (1H, m), 4.20 (1H, J=14.7 Hz), 4.94 (1H, d, J=8.4 Hz), 7.19 (1H, bs).

Anal Calcd for C$_{20}$H$_{32}$N$_2$O$_9$S: C, 50.41; H, 6.77; N, 5.88. Found: C, 50.32; H, 6.92; N, 5.76.

MS (ES) m/z 475.1 [M−H]$^-$.

Preparation 7

(1R,4S,5S,6S)-4-(2'S-tert-Butoxycarbonylamino-3'-methyl-butyrylamino)-2,2-dioxo-2λ$^6$-thia-bicyclo[3.1.0]hexane-4,6-dicarboxylic acid dimethyl ester

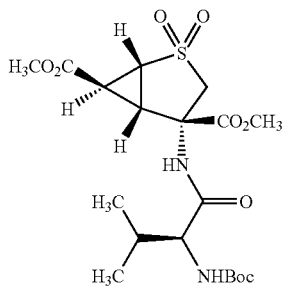

Prepare according to General Procedure A using commercially available N- BOC-(L)-Valine and (1R,4S,5S,6S)-4-Amino-2,2-dioxo-2λ$^6$-thia-bicyclo[3.1.0]hexane-4,6-dicarboxylic acid dimethyl ester (Preparation 4). Reflux reaction mixture overnight. Purify by PC-TLC, 4 mm SiO$_2$ rotor, (10% ethyl acetate/hexanes to 100% ethyl acetate). Yield 0.41 g (47%, 0.89 mmol) of a white foam.

$[\alpha]_D^{23}$=−35.36° (c=0.51, CHCl3).

$^1$H NMR (300 MHz, CDCl$_3$) δ 0.93 (3H, d, J=7.0 Hz), 0.96 (3H, d, J=6.6 Hz), 1.46 (9H, s), 2.06-2.13 (1H, m), 2.50 (1H, t, J=4.0 Hz), 2.94 (1H, d, J=15.0 Hz), 3.04 (1H, dd, J=4.4, 7.3 Hz), 3.43 (1H, dd, J=3.3, 6.6), 3.78 (3H, s), 3.80-3.86 (1H, m), 3.86 (3H, s), 4.24 (1H, d, J=15.0 Hz), 4.94 (1H, d, J=8.1 Hz), 7.15 (1H, bs).

Anal Calcd for C$_{19}$H$_{30}$N$_2$O$_9$S: C, 49.34; H, 6.54; N, 6.06. Found: C, 49.33; H, 6.44; N, 6.05.

MS (ES) m/z 461.2 [M−H]$^-$

Preparation 8

(1R,4S,5S,6S)-4-(2'S-tert-Butoxycarbonylamino-4'-methyl-pentanoylamino)-2,2-dioxo-2λ$^6$-thia-bicyclo[3.1.0]hexane-4,6-dicarboxylic acid dimethyl ester

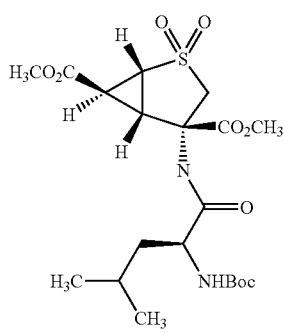

Prepare according to General Procedure A using commercially available N-BOC-(L)-Leucine monohydrate and (1R,4S,5S,6S)-4-Amino-2,2-dioxo-2λ$^6$-thia-bicyclo[3.1.0]hexane-4,6-dicarboxylic acid dimethyl ester (Preparation 4). Reflux the reaction mixture overnight. Purify by PC-TLC, 4 mm SiO$_2$ rotor, (10% ethyl acetate/hexanes to 100% ethyl acetate). Yield 0.85 g (94%, 1.78 mmol) of a white foam.

$[\alpha]_D^{23}$=−46.15° (c=1.04, CHCl$_3$).

$^1$H NMR (300 MHz, CDCl$_3$) δ 0.92 (3H, d, J=6.2 Hz), 0.95 (3H, d, J=6.6 Hz), 1.47 (9H, s), 1.42-1.47 (1H, m), 1.63-1.67 (1H, m), 2.46 (1H, t, J=3.7 Hz), 2.87 (1H, d, J=15.0 Hz), 3.04 (1H, dd, J=4.4, 7.3 Hz), 3.41 (1H, dd, J=3.7, 7.0), 3.78 (3H, s), 3.86 (3H, s), 4.00-4.05 (1H, m), 4.20 (1H, d, J=15.0 Hz), 4.75 (1H, d, J=6.6 Hz), 7.43 (1H, bs).

Anal Calcd for C$_{20}$H$_{32}$N$_2$O$_9$S: C, 50.41; H, 6.77; N, 5.88. Found: C, 50.30; H, 6.82; N, 5.75.

MS (ES) m/z 475.2 [M−H]$^-$.

Preparation 9

(1R,4S,5S,6S)-4-(2'S,6'-bis-tert-butoxycarbonylamino-hexanoylamino)-2,2-dioxo-2λ⁶-thia-bicyclo[3.1.0]hexane-4,6-dicarboxylic acid dimethyl ester

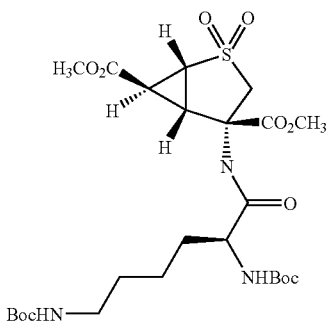

Prepare according to General Procedure A using commercially available N-BOC-Lys(BOC)-OH and (1R,4S,5S,6S)-4-Amino-2,2-dioxo-2λ⁶-thia-bicyclo[3.1.0]hexane-4,6-dicarboxylic acid dimethyl ester (Preparation 4). Reflux the reaction mixture overnight. Purify by PC-TLC, 4 mm SiO₂ rotor, (10% ethyl acetate/hexanes to 100% ethyl acetate). Yield 1.04 g (93%, 1.76 mmol) of a white foam.

$[\alpha]_D^{23}$=−32.0° (c=0.5, CHCl3).

¹H NMR (300 MHz, CDCl₃) δ 1.44 (9H, s), 1.46 (9H, s), 1.39-1.53 (3H, m), 1.56-1.65 (1H, m), 1.77-1.84 (2H, m), 2.50 (1H, t, J=4.4 Hz), 2.98-3.20 (4H, m), 3.42 (1H, dd, J=3.7, 7.0 Hz), 3.76 (3H, s), 3.86 (3H, s), 4.01 (1H, dd, J=7.7, 13.2 Hz), 4.09-4.19 (1H, m), 4.71 (1H, t, J=7.3 Hz), 5.13 (1H, bs), 7.59 (1H, bs).

Anal Calcd for $C_{25}H_{41}N_3O_{11}S$: C, 50.75; H, 6.98; N, 7.10. Found: C, 50.36; H, 6.99; N, 6.87.

MS (ES) m/z 590.2 [M−H]⁻.

Preparation 10

(1R,4S,5S,6S)-4-[2'S-tert-Butoxycarbonylamino-4'-(trityl-carbamoyl)-butyrylamino]-2,2-dioxo-2λ⁶-thia-bicyclo[3.1.0]hexane-4,6-dicarboxylic acid dimethyl ester

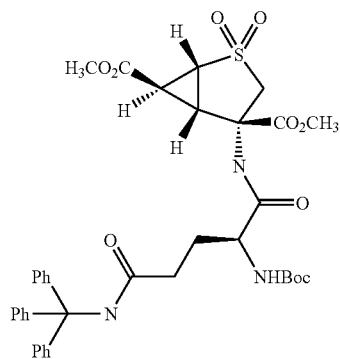

Prepare according to General Procedure A using commercially available N-BOC-(L)-Glutamine (Trt)-OH and (1R,4S,5S,6S)-4-Amino-2,2-dioxo-2λ⁶-thia-bicyclo[3.1.0]hexane-4,6-dicarboxylic acid dimethyl ester (Preparation 4). Reflux the reaction mixture overnight. Purify by PC-TLC, 4 mm SiO₂ rotor, (10% ethyl acetate/hexanes to 100% ethyl acetate). Yield 0.53 g (48%, 0.72 mmol) of a white foam.

$[\alpha]_D^{23}$=−8.0° (c=0.50, MeOH).

¹H NMR (300 MHz, CDCl₃) δ 1.42 (9H, s), 1.83-1.88 (1H, m), 2.03-2.18 (1H, m), 2.16 (1H, t, J=4.0 Hz), 2.57-2.64 (1H, m), 2.60 (1H, d, J=15.0 Hz), 2.64-2.80 (1H, m), 2.88 (1H, dd, J=4.4, 7.3 Hz), 3.26 (1H, dd, J=4.0, 7.0 Hz), 3.47 (3H, s), 3.76-3.90 (1H, m), 3.81 (3H, s), 4.05 (1H, d, J=15.0 Hz), 5.47 (1H, bs), 7.02 (1H, bs), 7.20-7.35 (15H, m), 8.68 (1H, bs).

Anal Calcd for $C_{38}H_{43}N_3O_{10}S$: C, 62.20; H, 5.91; N, 5.73. Found: C, 61.83; H, 6.09; N, 5.57.

MS (ES) m/z 731.9 [M−H]⁻;

HRMS calcd for $C_{38}H_{43}N_3O_{10}S$ [M+Na]⁺, 756.2567. Found, 756.2585.

Preparation 11

(1R,4S,5S,6S)-4-[(1'-tert-Butoxycarbonyl-pyrrolidine-2'S-carbonyl)-amino]-2,2-dioxo-2λ⁶-thia-bicyclo[3.1.0]hexane-4,6-dicarboxylic acid dimethyl ester

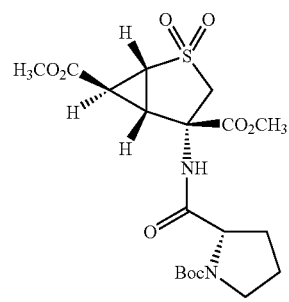

Prepare according to General Procedure A using commercially available Boc-(L)-proline (0.61 g, 2.9 mmol) and (1R,4S,5S,6S)-4-Amino-2,2-dioxo-2λ⁶-thia-bicyclo[3.1.0]hexane-4,6-dicarboxylic acid dimethyl ester (0.5 g, 1.9 mmol, Preparation 4). Purify using PC-TLC (ethyl acetate/hexanes) to yield 0.87 gram (99.2%) of the title compound.

$[\alpha]_D^{23}$=−61.2 (c=0.49, CHCl₃).

¹H NMR (300 MHz, CDCl₃) δ 1.51 (9H, s), 1.75-1.98 (3H, m), 2.35-2.5 (2H, m), 2.84 (1H, d, J=14.7 Hz), 2.9-3.03 (1H, m), 3.25-3.4 (1H, m), 3.3-4.1 (2H, m), 3.76 (3H, s), 3.86 (3H, s), 4.14-4.31 (2H, m), 8.66 (1H, s).

MS (ES) m/z 459.2 [M−1]⁻.

Preparation 12

(1R,4S,5S,6S)-4-(2'S-tert-Butoxycarbonylamino-4-methylsulfanyl-butyrylamino)-2,2-dioxo-2λ⁶-thia-bicyclo[3.1.0]hexane-4,6-dicarboxylic acid dimethyl ester

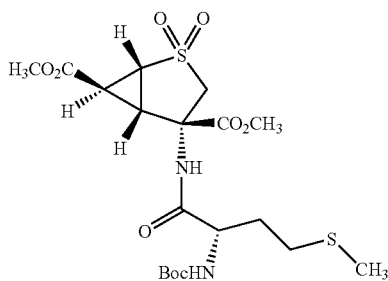

Prepare according to General Procedure A using commercially available Boc-(L)-Methionine (0.71 g, 2.9 mmol) and (1R,4S,5S,6S)-4-Amino-2,2-dioxo-2λ⁶-thia-bicyclo[3.1.0]hexane-4,6-dicarboxylic acid dimethyl ester (0.5 g, 1.9 mmol, Preparation 4). Purify using PC-TLC (ethyl acetate/hexanes) to yield 0.85 gram (90.5%) of the title compound.

$[\alpha]_D^{23}$=–20.4 (c=0.49, CHCl$_3$).

¹H NMR (300 MHz, CDCl$_3$) δ 1.46 (9H, s), 1.69 (1H, s), 1.8-2.05 (2H, m), 1.9-2.0 (1H, m), 1.95-2.3 (3H, bs), 2.0-2.2 (1H, m), 2.4-2.8 (2H, m), 2.48 (1H, t, J=4.0 Hz), 2.58 (1H, bs), 2.92 (1H, d, J=14.7 Hz), 3.01 (1H, dd, J=4.4, 7.0 Hz), 3.42 (1H, dd, J=3.7, 7.3 Hz), 3.78 (3H, s), 3.87 (3H, s), 4.22-4.24 (2H, m), 5.06 (1H, d, J=7.7 Hz), 7.27 (1H, s).

MS (ES) m/z 493.1 [M−1]⁻.

Preparation 13

(1R,4S,5S,6S)-4-[2'S-tert-Butoxycarbonylamino-3'-(1-tert-butoxycarbonyl-1H-indol-3-yl)-propionylamino]-2,2-dioxo-2λ⁶-thia-bicyclo[3.1.0.]hexane-4,6-dicarboxylic acid dimethyl ester

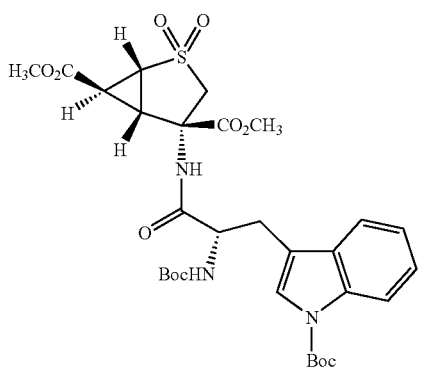

Prepare according to General Procedure A using commercially available Boc-(L)-Tryptophan(Boc) (1.1 g, 2.8 mmol) and (1R,4S,5S,6S)-4-Amino-2,2-dioxo-2λ⁶-thia-bicyclo[3.1.0]hexane-4,6-dicarboxylic acid dimethyl ester (0.5 g, 1.9 mmol, Preparation 4). Purify using PC-TLC (ethyl acetate/hexanes) to yield 0.7 g (56.7%) of the title compound.

¹H NMR (300 MHz, CDCl$_3$) δ 1.44 (9H, s), 1.67 (9H, s), 2.37 (1H, bs), 2.86 (1H, d, J=15.0 Hz), 2.88 (1H, t, J=4.4 Hz), 3.15 (2H, d, J=6.6 Hz), 3.39 (1H, dd, J=3.7, 7.0 Hz), 3.73 (3H, s), 3.83 (3H, s), 4.18 (1H, d, J=14.7 Hz), 4.37-4.44 (1H, m), 5.01 (1H, bd, J=8.1 Hz), 7.11 (1H, bs), 7.25-7.59 (4H, m), 8.14 (1H, bd, J=8.4 Hz).

$[\alpha]_D^{23}$=−19.6 (c=0.51, CHCl$_3$).

Anal. Calcd. For $C_{30}H_{39}N_3O_{11}S.1.0C_4H_8O_2$: C, 55.35; H, 6.42; N, 5.70. Found: C, 54.98; H, 6.09; N, 6.07.

HRMS calcd for $C_{30}H_{39}N_3O_{11}Na_1S$, 672.2203. Found, 672.2180.

Preparation 14

(1R,4S,5S,6S)-4-[2'S-tert-Butoxycarbonylamino-3'-(4-tert-butoxycarbonyloxy-phenyl)-propionylamino]-2,2-dioxo-2λ⁶-thia-bicyclo[3.1.0.]hexane-4,6-dicarboxylic acid dimethyl ester

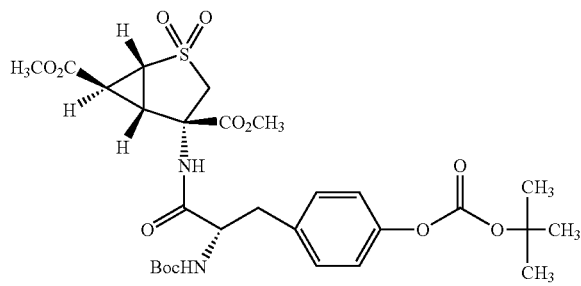

Prepare according to General Procedure A using commercially available 2S-tert-butoxycarbonylamino-3-(4-tert-butoxycarbonyloxy-phenyl)-propionic acid (1.1 g, 2.9 mmol) and (1R,4S,5S,6S)-4-Amino-2,2-dioxo-2λ⁶-thia-bicyclo[3.1.0]hexane-4,6-dicarboxylic acid dimethyl ester (0.5 g, 1.9 mmol, Preparation 4). Purify using PC-TLC (ethyl acetate/hexanes) to yield 0.94 g (79.0%) of the title compound.

$[\alpha]_D^{23}$=+4 (c=1.00, CH$_3$OH).

¹H NMR (300 MHz, CDCl$_3$) δ 1.44 (9H, s), 1.56 (9H, s), 2.44 (1H, t, J=4.0 Hz), 2.88 (1H, d, J=14.7 Hz), 2.98 (1H, dd, J=4.4, 7.3 Hz), 3.04 (2H, d, J=7.3 Hz), 3.38 (1H, dd, J=4.0, 7.3 Hz), 3.77 (3H, s), 3.83 (3H, s), 4.11 (1H, d, J=14.3 Hz), 4.22-4.29 (1H, app q, J=7.3 Hz), 4.92 (1H, bd, J=7.7 Hz), 7.07 (1H, bs), 7.1-7.26 (4H, m).

HRMS calcd for $C_{28}H_{38}N_2O_{12}SNa$, 649.2043. Found, 649.2001.

Preparation 15

(1R,4S,5S,6S)-4-(3'-Acetoxy-2'S-tert-butoxycarbonylamino-propionyl)amino-2,2-dioxo-2λ⁶-thiabicyclo[3.1.0]hexane-4,6-dicarboxylic acid dimethyl ester

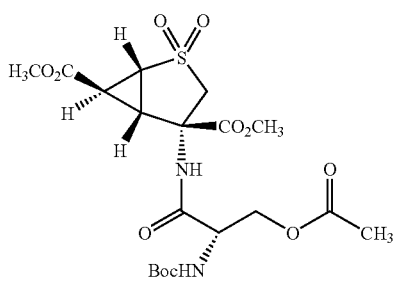

Prepare according to General Procedure A using 3-acetoxy-2S-(tert-butoxycarbonylamino)propionic acid (0.25 g, 1.0 mmol, Preparation 44) and (1R,4S,5S,6S)-4-Amino-2,2-dioxo-2λ⁶-thia-bicyclo[3.1.0]hexane-4,6-dicarboxylic acid dimethyl ester (0.2 g, 0.8 mmol, Preparation 4) with the exception that DMAP is not used. Purify using PC-TLC (ethyl acetate/hexanes) to yield 0.19 g (48.2%) of the title compound.

$[\alpha]_D^{23}$=−24 (c=1.0, CH$_3$OH).

$^1$H NMR (300 MHz, CDCl$_3$) δ 1.47 (9H, s), 2.10 (3H, s), 2.51 (1H, t, J=4.4 Hz), 2.99-3.07 (2H, m), 3.43 (1H, dd, J=4.0, 7.3 Hz), 3.77 (3H, s), 3.86 (3H, s), 4.14-4.40 (4H, m), 5.29 (1H, bd, J=7.3 Hz), 7.64 (1H, bs).

HRMS calcd for C$_{19}$H$_{28}$N$_2$O$_{11}$SNa, 515.1312. Found, 515.1305.

Preparation 16

(1R,2S,4R,5R,6R)-2-Amino-4-fluorobicyclo[3.1.0] hexane-2,6-dicarboxylic acid diethyl ester

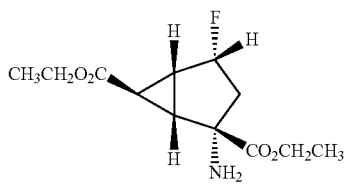

To a slurry of (1R,2S,4R,5R,6R)-2-amino-4-fluorobicyclo[3.1.0]hexane-2,6-dicarboxylic acid (14.45 g, 71.12 mmol, U.S. Pat. No. 5,958,960) in 202 mL of absolute ethanol at room temperature add thionyl chloride (26 mL, 356 mmol) dropwise over 20 minutes. Heat the slurry to reflux and allow to stir for 3 hours. Allow to cool to room temperature and stir overnight. Concentrate the resultant solution in vacuo to a residue then dilute with 136 mL of ethyl acetate and treat with 306 mL of 10% aqueous sodium carbonate over 15 minutes with swirling by hand such that the final pH is 10. Separate the layers and wash the aqueous layer with ethyl acetate (1×136 mL). Wash the combined organic extracts with brine (1×136 mL), dry (MgSO$_4$), filter, and concentrate in vacuo to provide 17.07 g (93%) of the title compound as white solid.

$[\alpha]_D^{23}$=+20.37° (c=1.1, MeOH).

m.p.=64-66° C.

$^1$H NMR (400 MHz, CDCl$_3$) δ 1.28 (3H, t, J=7.3 Hz), 1.31 (3H, t, J=6.8 Hz), 1.34-1.45 (1H, m), 1.85 (2H, bs), 2.17-2.21 (2H, m), 2.32-2.34 (1H, m), 2.49 (1H, dd, J=7.8, 14.1 Hz), 4.24 (2H, dq, J=1.5, 7.3 Hz), 5.33-5.52 (1H, m). Anal. calcd. for C$_{12}$H$_{18}$FNO$_4$: C, 55.59; H, 7.00; N, 5.40. Found: C, 55.29; H, 6.75; N, 5.45.

MS (ES) m/z found 260.3 [M+H]+.

Preparation 17

(1R,2S,4R,5R,6R)-2-[2'S-(tert-butoxycarbonylamino)propionyl]amino-4-fluorobicyclo[3.1.0]hexane-2,6-dicarboxylic acid diethyl ester

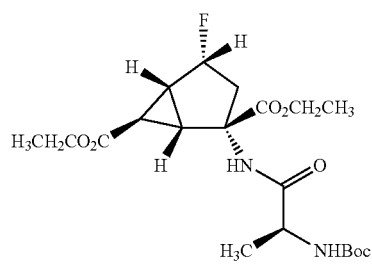

To a solution of N-Boc-L-alanine (38.62 g, 204 mmol) in 396 mL of methylene chloride at −22° C. under nitrogen add N-methyl morpholine (22.44 mL, 204 mmol) followed by iso-butyl chloroformate (26.48 mL, 204 mmol) dropwise over 15 min such that the reaction temperature does not exceed −18° C. Allow the resultant thin slurry to stir at −20° C. for 30 minutes at which time a solution of (1R,2S,4R,5R,6R)-2-amino-4-fluorobicyclo[3.1.0]hexane-2,6-dicarboxylic acid diethyl ester (49.46 g, 191 mmol, Preparation 16) in 247 mL of methylene chloride is added over 40 min such that the reaction temperature does not exceed −16° C. Upon completion of the addition, remove the reaction from the cooling bath and allow to stir at ambient temperature for 70 minutes at which time the reaction temperature reached 15° C. and the color became faint orange. Treat the reaction with 408 mL of 1 N HCl and stir for 5 minutes then separate the layers. Wash the organic layer with saturated aqueous sodium bicarbonate (1×408 mL), dry (Na$_2$SO$_4$), filter, and concentrate in vacuo to a white foam (88.16 g).

Anal. calcd. For C$_{20}$H$_{31}$FN$_2$O$_7$.0.1CH$_2$Cl$_2$: C, 55.00; H, 7.16; N, 6.38. Found: C, 55.18; H, 7.18; N, 6.49.

MS (ES) m/z 431.3 [M+H]+, 331.2 [M+H-Boc]+.

Preparation 18

(1R,2S,4R,5R,6R)-2-[2'S-(tert-butoxycarbonylamino)propionyl]amino-4-fluorobicyclo[3.1.0]hexane-2,6-dicarboxylic acid

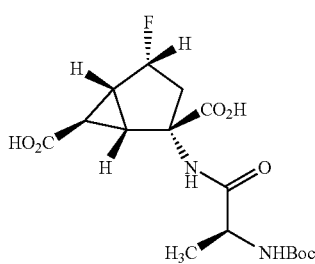

To a solution of (1R,2S,4R,5R,6R)-2-[2'S-(tert-butoxycarbonylamino)propionyl]-amino-4-fluorobicyclo[3.1.0]hexane-2,6-dicarboxylic acid diethyl ester (88.16 g, 191 mmol, Preparation 17) in 238 mL of THF at room temperature add 238 mL (477 mmol) of 2N sodium hydroxide. Allow the biphasic mixture to stir vigorously at room temperature for 2.5 hours at which time the reaction is homogeneous. Dilute the mixture with 238 mL of t-butyl methyl ether followed by mixing and separation of the layers. Further dilute the aqueous layer with 238 mL of water and filter to remove particulate matter. Treat the solution with concentrated HCl (42.9 mL, 515 mmol) over 30 minutes optionally followed by seeding with the title compound and stirring for 1 hour. Filter the resultant slurry, wash with water (2×100 mL), and vacuum dry at 45° C. for 40 hours to provide 72.2 g of the title compound as a white solid. Stir a portion of the solid (69.5 g) with 490 mL of acetone for 1 hour to produce a hazy solution; filter and wash with acetone (2×100 mL). Concentrate the filtrate in vacuo to a white foam which is further dried in vacuo at 45° C. for 16 hours to provide 61.8 g (86%, corrected for 12% wt/wt acetone) of the title compound. This material was used in Examples 14-18 without characterization.

Preparation 19

(1S,2S,4S,5R,6R)-4-Acetyloxy-2-(tert-butoxycarbonyl)aminobicyclo[3.1.0]hexane-2,6-dicarboxylic acid diethyl ester

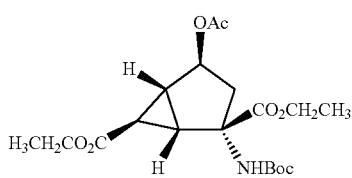

To a solution of (1S,2S,4S,5R,6R)-2-(tert-butoxycarbonyl)amino-4-hydroxybicyclo[3.1.0]hexane-2,6-dicarboxylic acid diethyl ester (1.50 g, 4.20 mmol, U.S. Pat. No. 5,958,960), pyridine (0.365 mL, 4.62 mmol) and DMAP (0.513 g, 4.20 mmol) in dichloromethane (40 mL) under nitrogen add acetic anhydride (0.514 mL, 5.0 mmol). Stir at room temperature for 16 hours, dilute with dichloromethane, and pour into 10% aqueous citric acid solution (50 mL). Wash the organic layer with water (50 mL) and brine (50 mL). Dry over MgSO$_4$, filter and concentrate in vacuo, to produce the title compound as a white solid (1.295 g, 75%).

LCMS: m/z 400 [M+H]$^+$ and m/z 300 [M+H—CO$_2^t$Bu]$^+$ @ R$_T$ 1.39 min.

Preparation 20

(1S,2S,4S,5R,6R)-4-Acetyloxy-2-aminobicyclo[3.1.0]hexane-2,6-dicarboxylic acid diethyl ester

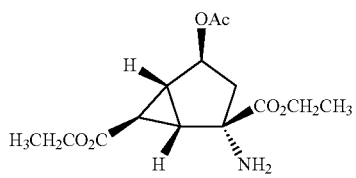

Dissolve (1S,2S,4S,5R,6R)-4-acetyloxy-2-(tert-butoxycarbonyl)aminobicyclo[3.1.0]hexane-2,6-dicarboxylic acid diethyl ester (1.25 g, 3.13 mmol, Preparation 19) in a solution of 95% TFA in dichloromethane (60 mL) and stir under nitrogen at room temperature for 5 minutes. After this time remove the TFA/dichloromethane in vacuo. Dissolve the crude product in a suspension of NaHCO$_3$ (1.00 g) in dichloromethane (50 mL) and stir for 30 minutes. Filter the suspension, wash with dichloromethane (3×25 mL), and concentrate in vacuo to afford 916 mg (98%) of the product as a yellow oil.

LCMS: m/z 300 [M+H]$^+$ @ R$_T$ 0.92 min.

Preparation 21

(1S,2S,4S,5R,6R)-4-Acetyloxy-2-[2'S-(tert-butoxy)carbonylaminopropionyl]-aminobicyclo[3.1.0]hexane-2,6-dicarboxylic acid diethyl ester

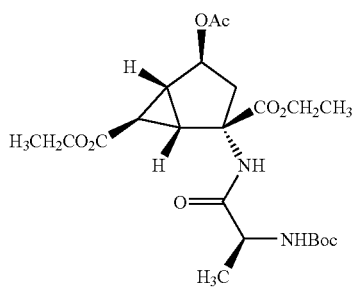

To a suspension of (1S,2S,4S,5R,6R)-4-acetyloxy-2-aminobicyclo[3.1.0]hexane-2,6-dicarboxylic acid diethyl ester (0.80 g, 1.94 mmol, Preparation 20) and Boc-L-Ala (0.477 g, 2.52 mmol) in anhydrous dichloromethane (50 mL) under nitrogen sequentially add EDC (0.519 g, 2.72 mmol), HOBt (0.314 g, 2.32 mmol), catalytic DMAP (0.024 g, 0.19 mmol), and triethylamine (1.08 mL, 7.76 mmol). After stirring at room temperature for ca. 15 minutes, the initial white suspension dissolves completely. Stir the reaction for 16 hours, dilute with dichloromethane, and wash with saturated aqueous NaHCO$_3$ solution (50 mL), 1.0 N aqueous HCl solution (3×20 mL), and saturated brine solution (40 mL). Dry the organic layer over MgSO$_4$ and filter, and concentrate in vacuo. Purify the resulting crude amide by column chromatography using a (4:1) mixture of ethyl acetate and hexanes as eluent to afford 638 mg (75%) of the product as a white solid.

¹H NMR (CD₃OD)*: δ 5.05 (1H, d, 5.7 Hz), 4.09 (2H, q, 7.3 Hz), 4.02 (2H, q, 7.3 Hz), 4.01-3.94 (1H, m), 2.65-2.59 (2H, m), 2.38 (1H, d, 14 Hz), 2.10-2.03 (3H, m), 1.91 (3H, s), 1.78 (1H, dd, 5.9 Hz, 16 Hz), 1.59 (1H, br s), 1.34 (9H, s), 1.16 (6H, 2xt, 7.3 Hz);

*N.B. Exchangeable protons not observed by NMR=2.

LCMS: m/z 471 [M+H]⁺ and m/z 371 [M+H—CO₂ᵗBu]⁺ @ R_T 1.30 min.

R_f 0.50 (80% ethyl acetate:heptane).

Preparation 22

(1S,2S,4S,5R,6R)-2-amino-4-hydroxy-bicyclo[3.1.0.]hexane-2,6-dicarboxylic acid diethyl ester

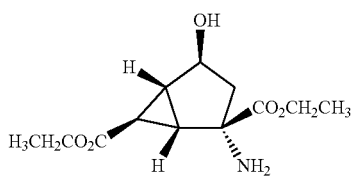

Cool a solution of (1S,2S,4S,5R,6R)-2-tert-butoxycarbonylamino-4-hydroxy-bicyclo[3.1.0]hexane-2,6-dicarboxylic acid diethyl ester (5.0 g, 14.0 mmol, U.S. Pat. No. 5,958,960) in ethyl acetate to 0° C. Bubble anhydrous HCl (g) into the solution until saturated and stir for 0.5 hour. Allow the reaction to warm to room temperature and stir for 1 hour. Concentrate the reaction mixture and partition between ethyl acetate and H₂O. Treat the aqueous layer with NaHCO₃ (aq) and extract with ethyl acetate. Dry the organics with K₂CO₃ and concentrate to yield 2.2 g (59.7%) of white solids.

$[\alpha]_D^{23}$=−30.8 (c=0.52, CH₃OH).

¹H NMR (300 MHz, CDCl₃) δ 1.26 (3H, t, J=7.33 Hz), 1.36 (3H, t, 7.33 Hz), 1.60 (1H, dd, J=5.87, 15.40 Hz), 1.64 (1H, t, J=2.93 Hz), 2.27 (2H, bs), 2.15-2.29 (3H, m), 3.93 (1H, bs), 4.13 (2H, q, J=6.97 Hz), 4.27-4.36 (3H, m).

Anal. Calcd. For C₁₂H₁₉NO₅: C, 56.02; H, 7.44; N, 5.44. Found: C, 55.75; H, 7.36; N, 5.40.

MS (ES) m/z 258.1 [M+H]⁺.

Preparation 23

(1S,2S,4S,5R,6R)-2-(2'-tert-Butoxycarbonylamino-acetylamino)-4-hydroxy-bicyclo[3.1.0]hexane-2,6-dicarboxylic acid diethyl ester

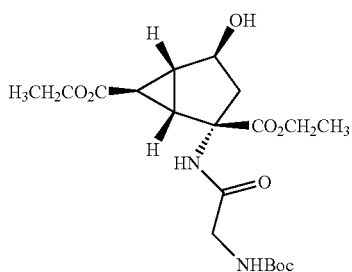

Prepare according to General Procedure A using Boc-Glycine (458 mg, 2.62 mmol, Aldrich) and (1S,2S,4S,5R,6R)-2-amino-4-hydroxy-bicyclo[3.1.0]hexane-2,6-dicarboxylic acid diethyl ester (450 mg, 1.75 mmol, Preparation 22). Purify on 35 g of silica eluting with a gradient from 50/50 to 20/80 hexanes/ethyl acetate. Yield: 560 mg (77%).

¹H NMR (400 MHz, CDCl₃) δ 1.28 (3H, t, J=7.3 Hz), 1.29 (3H, t, J=7.3 Hz), 1.48 (9H, s), 1.57 (2H, m), 2.21 (1H, m), 2.41 (1H, dd, J=2.9, 5.8 Hz), 2.81 (1H, d, J=15.6 Hz), 3.76 (1H, d, J=5.8 Hz), 4.10-4.18 (3H, m), 4.26 (2H, q, J=7.3 Hz), 4.33 (1H, m), 5.10 (1H, bs), 6.86 (1H, bs).

Anal Calcd for C₁₉H₃₀N₂O₈: C, 55.06; H, 7.30; N, 6.76. Found: C, 55.24; H, 7.50; N, 6.76.

MS (ES) m/z 415.2 [M+H]⁺, 437.2 [M+Na]⁺.

Preparation 24

(1S 2S,4S,5R,6R)-2-(2'S-tert-Butoxycarbonylamino-3'-methyl-butyrylamino)-4-hydroxy-bicyclo[3.1.0]hexane-2,6-dicarboxylic acid diethyl ester

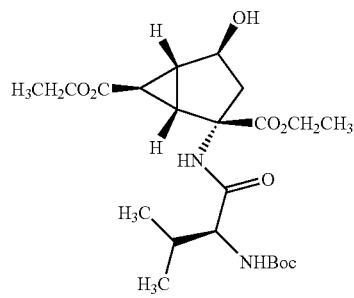

Prepare according to General Procedure A using Boc-L-Valine (569 mg, 2.62 mmol, Sigma) and (1S,2S,4S,5R,6R)-2-amino-4-hydroxy-bicyclo[3.1.0]hexane-2,6-dicarboxylic acid diethyl ester (450 mg, 1.75 mmol, Preparation 22). Purify the crude material on 35 g of silica; elute with a gradient from 70/30 to 20/80 hexanes/ethyl acetate.

Yield: 694 mg (87%) of a white foam.

¹H NMR (400 MHz, CDCl₃) δ 0.95 (3H, d, J=6.8 Hz), 1.00 (3H, d, J=6.8 Hz), 1.29 (6H, t, J=7.3 Hz), 1.45 (9H, s), 1.52-1.60 (2H, m), 2.08 (1H, m), 2.20 (1H, m), 2.42 (1H, m), 2.81 (1H, d, J=15.6 Hz), 3.86 (1H, dd, J=6.3, 8.8 Hz), 4.14 (2H, q, J=7.3 Hz), 4.21-4.32 (4H, m), 5.00 (1H, d, J=8.3 Hz), 6.63 (1H, s).

Anal Calcd for C₂₂H₃₆N₂O₈: C, 57.88; H, 7.95; N, 6.14. Found: C, 57.87; H, 8.03; N, 6.12.

MS (ES) m/z 457.2 [M+H]⁺, 479.2 [M+Na]⁺.

Preparation 25

(1S,2S,4S,5R,6R)-2-(2'S-tert-Butoxycarbonylamino-4'-methyl-pentanoylamino)-4-hydroxy-bicyclo[3.1.0]hexane-2,6-dicarboxylic acid diethyl ester

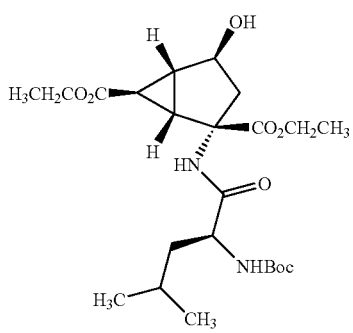

Prepare according to General Procedure A using Boc-L-Leucine (606 mg, 2.62 mmol, Chemlog) and (1S,2S,4S,5R,6R)-2-amino-4-hydroxy-bicyclo[3.1.0]hexane-2,6-dicarboxylic acid diethyl (450 mg, 1.75 mmol, Preparation 22). Purify the crude material on 35 g of silica; elute with a gradient from 70/30 to 20/80 hexanes/ethyl acetate. Yield 689 mg (84%) of a white foam.

$^1$H NMR (400 MHz, CDCl$_3$) δ 0.96 (6H, m), 1.28 (3H, t, J=7.3 Hz), 1.29 (3H, t, J=7.3 Hz), 1.46 (9H, s), 1.45-1.73 (5H, m), 2.20 (1H, m), 2.42 (1H, m), 2.80 (1H, d, J=16.1 Hz), 4.07-4.35 (7H, m), 4.81 (1H, bd), 6.86 (1H, bs).

Anal Calcd for C$_{23}$H$_{38}$N$_2$O$_8$·0.1H$_2$O: C, 58.48; H, 8.15; N, 5.93. Found: C, 58.22; H, 7.94; N, 5.92.

MS (ES) m/z 471.2 [M+H]$^+$, 493.2 [M+Na]$^+$.

Preparation 26

(1S,2S,4S,5R,6R)-2-(2'S-tert-Butoxycarbonylamino-3'S-methyl-pentanoylamino)-4-hydroxy-bicyclo[3.1.0]hexane-2,6-dicarboxylic acid diethyl ester

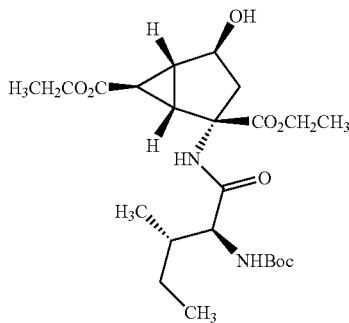

Prepare according to General Procedure A using Boc-L-Isoleucine (606 mg, 2.62 mmol, Aldrich) and (1S,2S,4S,5R,6R)-2-amino-4-hydroxy-bicyclo[3.1.0]hexane-2,6-dicarboxylic acid diethyl ester (450 mg, 1.75 mmol, Preparation 22). Purify the crude material on 35 g of silica eluting with a gradient from 70/30 to 20/80 hexanes/ethyl acetate. Yield: 731 mg (89%).

$^1$H NMR (400 MHz, CDCl$_3$) δ 0.92 (3H, t, J=7.3 Hz), 0.97 (3H, d, J=6.8 Hz), 1.17 (1H, m), 1.29 (6H, t, J=6.8 Hz), 1.46 (9H, s), 1.53 (1H, dd, J=5.8, 15.6 Hz), 1.58 (1H, t, J=2.4 Hz), 1.74 (1H, m), 1.83 (1H, m), 2.20 (1H, m), 2.43 (1H, m), 2.80 (1H, d, J=15.6 Hz), 3.88 (1H, dd, J=7.3, 8.8 Hz), 4.12-4.32 (6H, m), 4.98 (1H, d, J=7.3 Hz), 6.60 (1H, s). Anal Calcd for C$_{23}$H$_{38}$N$_2$O$_8$·0.2H$_2$O: C, 58.25; H, 8.16; N, 5.91. Found: C, 58.17; H, 8.11; N, 5.91.

MS (ES) m/z 471.2 [M+H]$^+$, 493.2 [M+Na]$^+$.

Preparation 27

(1S,2S,4S,5R,6R)-2-[2'-(2-tert-Butoxycarbonylamino-acetylamino)-acetylamino]-4-hydroxy-bicyclo[3.1.0]hexane-2,6-dicarboxylic acid diethyl ester

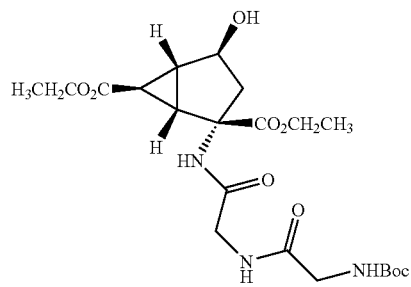

Prepare according to General Procedure A using Boc-Gly-Gly (474 mg, 2.04 mmol) and (1S,2S,4S,5R,6R)-2-amino-4-hydroxy-bicyclo[3.1.0]hexane-2,6-dicarboxylic acid diethyl ester hydrochloride (400 mg, 1.36 mmol, Preparation 22 without basic work-up) with the following exceptions. No DMAP is used. Add one equivalent of triethylamine. Purify the crude material on 35 g of silica; elute with ethyl acetate. Yield: 517 mg (81%).

$[\alpha]_D^{23}$=−18.18 (c=0.55, MeOH).

$^1$H NMR (300 MHz, CDCl$_3$) δ 1.26 (3H, t, J=6.8 Hz), 1.27 (1H, t, J=7.3 Hz), 1.28 (3H, t, J=6.8 Hz), 1.46 (9H, s), 1.59 (1H, t, J=3.4 Hz), 1.62 (1H, dd, J=6.3, 16.1 Hz), 2.21 (1H, dd, J=2.9, 5.8 Hz), 2.46 (1H, dd, J=2.4, 5.8 Hz), 2.73 (1H, d, J=15.6 Hz), 3.78-3.91 (3H, m), 4.01-4.15 (3H, m), 4.24 (2H, q, J=6.8 Hz), 4.32 (1H, d, J=5.8 Hz), 5.28 (1H, b), 6.87 (1H, bt, J=4.9 Hz), 7.39 (1H, bs).

HRMS calcd for C$_{21}$H$_{34}$N$_3$O$_9$, 472.2295. Found, 472.2303.

HPLC: 16.755 min. Column: Symmetry C18, 3.5 um, 4.6×150 mm. λ=230 nM. Flow Rate: 1 mL/min. Gradient: 10% to 50% ACN/water containing 0.1% TFA over 25 min.

Preparation 28

(1S,2S,4S,5R,6R)-2-[2'-(2S-tert-Butoxycarbonylamino-propionylamino)-acetylamino]-4-hydroxy-bicyclo[3.1.0]hexane-2,6-dicarboxylic acid diethyl ester

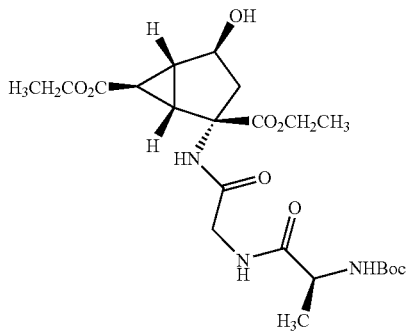

Prepare according to General Procedure A using Boc-Ala-Gly (502 mg, 2.04 mmol) and (1S,2S,4S,5R,6R)-2-amino-4-hydroxy-bicyclo[3.1.0]hexane-2,6-dicarboxylic acid diethyl ester hydrochloride (400 mg, 1.36 mmol, Preparation 22 without basic work-up) with the following exceptions. No DMAP is used. Add one equivalent of triethylamine. Purify the crude material on 35 g of silica eluting with ethyl acetate.

Yield: 500 mg (76%).

$[\alpha]_D^{23}$=–31.37 (c=0.55, MeOH).

$^1$H NMR (300 MHz, CDCl$_3$) δ 1.27 (3H, t, J=6.8 Hz), 1.28 (3H, t, J=6.8 Hz), 1.42 (3H, d, J=6.8 Hz), 1.45 (9H, s), 1.58 (1H, t, J=3.4 Hz), 1.64 (1H, dd, J=5.8, 15.6 Hz), 2.23 (1H, dd, J=3.4, 5.8 Hz), 2.50 (1H, dd, J=2.9, 6.3 Hz), 2.69 (1H, d, J=15.6 Hz), ABq of doublets (2H, $v_A$=3.87, $v_B$=3.98 $J_{AB}$=17.1 Hz, $J_d$=6.3 Hz), 3.92 (1H, m), 4.07-4.16 (3H, m), 4.24 (2H, q, J=7.3 Hz), 4.32 (1H, b), 5.08 (1H, b), 6.84 (1H, bt, J=4.88 Hz), 7.14 (1H, bs).

HRMS calcd for C$_{22}$H$_{36}$N$_3$O$_9$, 486.2452. Found, 486.2451.

Preparation 29

(1S,2S,4S,5R,6R)-2-(2'-tert-Butoxycarbonylamino-3'-phenyl-propionylamino)-4-hydroxy-bicyclo[3.1.0]hexane-2,6-dicarboxylic acid diethyl ester

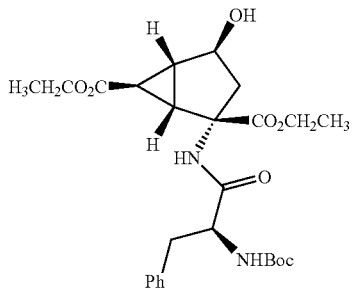

Prepare according to the General Procedure A using Boc-L-phenylalanine (772 mg, 2.91 mmoles) and (1S,2S,4S,5R,6R)-2-amino-4-hydroxy-bicyclo[3.1.0]hexane-2,6-dicarboxylic acid diethyl ester (480 mg, 1.94 mmoles, Preparation 22). Concentrate the crude reaction mixture, dissolve in dichloromethane, flash through a short silica gel plug with ethyl acetate/DCM (1:1), and concentrate in-vacuo to give a yellow oil. Further purify the material by silica gel chromatography eluting with 30% ethyl acetate/hexanes to 80% ethyl acetate/hexanes to afford 852 mg (87%) of the title compound.

$[\alpha]_D^{23}$=–23.66 (c=0.93, MeOH).

$^1$H NMR (400 MHz, CD$_3$OD) δ 1.22-1.30 (6H, m), 1.35 (9H, s), 1.59 (1H, t, J=2.9 Hz), 1.70 (1H, dd, J=5.5, 15.4 Hz), 2.06 (1H, m), 2.40 (1H, d, J=15.4 Hz), 2.63 (1H, dd, J=2.9, 5.9 Hz), 2.76 (1H, dd, J=9.2, 13.9 Hz), 4.08-4.33 (6H, m), 7.20-7.29 (5H, m).

MS found 505.0 [M+H]$^+$.

HRMS calcd for C$_{26}$H$_{36}$N$_2$O$_8$, 505.2550. Found, 505.2559.

Preparation 30

(1S,2S,4S,5R,6R)-2-[2'-tert-Butoxycarbonylamino-4'-(trityl-carbamoyl)-butyrylamino]-4-hydroxy-bicyclo[3.1.0]hexane-2,6-dicarboxylic acid diethyl ester

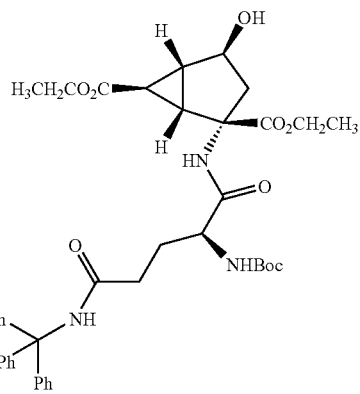

Prepare according to General Procedure A using Boc-L-glutamine(Trityl)-OH (1.40 g, 2.86 mmoles) and (1S,2S,4S,5R,6R)-2-amino-4-hydroxy-bicyclo[3.1.0]hexane-2,6-dicarboxylic acid diethyl ester (490 mg, 1.90 mmoles, Preparation 22), with the exception that DMAP is not used. Concentrate the crude reaction mixture, dissolve in dichloromethane, flash through a short silica gel plug with ethyl acetate, and concentrate in-vacuo to give a yellow oil. Further purify by silica gel chromatography eluting with 30% ethyl acetate/hexanes to 100% ethyl acetate/hexanes to afford 1.3 g (94%) of the title compound.

$[\alpha]_D^{23}$=–21.28 (c=0.94, MeOH).

$^1$H NMR (400 MHz, CD$_3$OD) δ 1.18-1.26 (6H, m), 1.44 (9H, s), 1.62-1.74 (3H, m), 1.91-2.00 (1H, m), 2.05 (1H, m), 2.38-2.48 (3H, m), 2.54 (1H, m), 4.00-4.27 (6H, m), 7.18-7.30 (15H, m).

MS found 728.2 [M+H]$^+$.

HRMS calcd for C$_{41}$H$_{49}$N$_3$O$_9$, 728.3547. Found, 728.3533.

Preparation 31

(1S,2S,4S,5R,6R)-2-(2'S,6'-Bis-tert-butoxycarbonylamino-hexanoylamino)-4-hydroxy-bicyclo[3.1.0]hexane-2,6-dicarboxylic acid diethyl ester

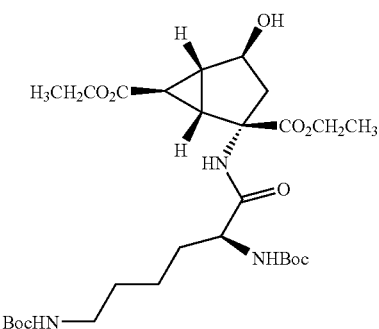

Prepare according to General Procedure A using Boc-L-lysine(Boc)-OH (910 mg, 2.63 mmoles) and (1S,2S,4S,5R,6R)-2-amino-4-hydroxy-bicyclo[3.1.0.]hexane-2,6-dicarboxylic acid diethyl ester (450 mg, 1.75 mmoles, Preparation 22), with the exception that DMAP is not added to the reaction mixture. Concentrate the crude reaction mixture, dissolve in dichloromethane, flash through a short silica gel plug with ethyl acetate, and concentrate in-vacuo to give a yellow oil. Further purify the material by silica gel chromatography eluting with ethyl acetate/hexanes (1:1) to afford 800 mg (78%) of the title compound.

$[\alpha]_D^{23}$=−30.19 (c=0.53, MeOH).

$^1$H NMR (400 MHz, CD$_3$OD) δ 1.21-1.24 (6H, m), 1.26-1.77 (27H, m), 2.07 (1H, m), 2.42 (1H, d, J=15.8 Hz), 2.59 (H, dd, J=2.6, 5.5 Hz), 3.03 (1H, t, J=6.2 Hz), 3.99 (1H, m), 4.07-4.28 (5H, m).

MS found 586.1 [M+H]$^+$.

HRMS calcd for C$_{28}$H$_{47}$N$_3$O$_{10}$, 586.3340. Found, 586.3348.

Preparation 32

(1S,2S,4S,5R,6R)-2-[2'-tert-Butoxycarbonylamino-3'-(trityl-carbamoyl)-propionylamino]-4-hydroxy-bicyclo[3.1.0]hexane-2,6-dicarboxylic acid diethyl ester

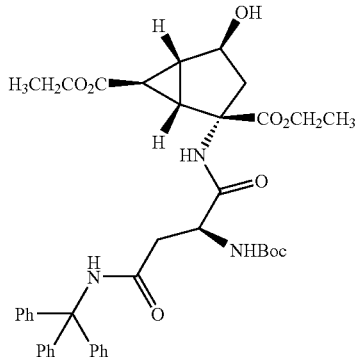

Prepare according to General Procedure A using Boc-L-Asparagine(Trityl)-OH (1.35 g, 2.84 mmoles) and (1S,2S,4S,5R,6R)-2-amino-4-hydroxy-bicyclo[3.1.0]hexane-2,6-dicarboxylic acid diethyl ester (476 mg, 1.85 mmoles, Preparation 22), with the exception that DMAP is not added to the reaction mixture. Concentrate the crude reaction mixture, dissolve in dichloromethane, flash through a short silica gel plug with ethyl acetate, and concentrate in-vacuo to give a yellow oil. Further purify the material by silica gel chromatography eluting with 20% ethyl acetate/hexanes to 50% ethyl acetate/hexanes to afford 1.07 g (81%) of the title compound.

$[\alpha]_D^{23}$=−25.45 (c=0.55, MeOH).

$^1$H NMR (400 MHz, CD$_3$OD) δ 1.19-1.26 (6H, m), 1.45 (9H, s), 1.61-1.69 (2H, m), 2.05 (1H, m), 2.44 (1H, d, J=15.4 Hz), 2.51-2.72 (3H, m), 4.02-4.21 (4H, m), 4.25 (1H, d, J=5.5 Hz), 4.36 (1H, dd, J=4.8, 8.8 Hz), 7.18-7.30 (15H, m).

MS found 714.1 [M+H]$^+$.

HRMS calcd for C$_{40}$H$_{47}$N$_3$O$_9$, 714.3391. Found, 714.3380.

Preparation 33

(1S,2S,4S,5R,6R)-2-[2'-tert-Butoxycarbonylamino-3'-(1'-tert-butoxycarbonyl-1H-indol-3'-yl)-propionylamino]-4-hydroxy-bicyclo[3.1.0]hexane-2,6-dicarboxylic acid diethyl ester

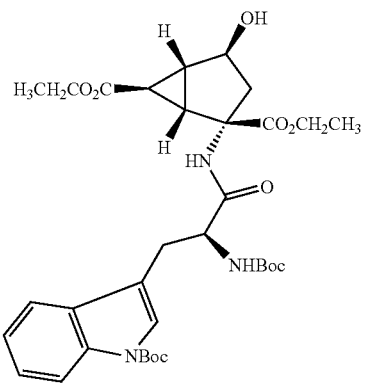

Prepare according to General Procedure A using Boc-L-tryptophan(Boc)-OH (1.18 g, 2.91 mmoles) and (1S,2S,4S,5R,6R)-2-amino-4-hydroxy-bicyclo[3.1.0.]hexane-2,6-dicarboxylic acid diethyl ester (520 mg, 1.90 mmoles, Preparation 22). Concentrate the crude reaction mixture, dissolve in dichloromethane, flash through a short silica gel plug with ethyl acetate, and concentrate in-vacuo to give a yellow oil. Further purify the material by silica gel chromatography eluting with ethyl acetate/DCM (1:1) to afford 1.2 g (92%) of the title compound.

$[\alpha]_D^{23}$=−12.5 (c=0.96, MeOH).

$^1$H NMR (400 MHz, CD$_3$OD) δ 1.18-1.27 (6H, m), 1.34 (9H, s), 1.62 (1H, t, J=2.9 Hz), 1.67 (9H, s), 1.74 (1H, dd, J=5.9, 15.2 Hz), 2.07 (1H, m), 2.46 (1H, d, J=15.7 Hz), 2.60 (1H, d, J=2.9, 5.9 Hz), 2.89 (1H, dd, J=9.3, 15.0 Hz), 3.16 (1H, dd, J=4.9, 15.2 Hz), 4.04-4.12 (2H, m), 4.18-4.24 (2H, m), 4.27 (1H, d, J=5.4 Hz), 4.43 (1H, dd, J=5.4, 9.3 Hz), 7.26 (2H, m), 7.52 (1H, s), 7.64 (1H, d, J=7.3 Hz), 8.10 (1H, d, J=8.3 Hz).

MS found 644.8 [M+H]+, 666.8 [M+Na]+.
HRMS calcd for $C_{33}H_{44}N_3O_{10}$, 666.3002. Found, 666.2988.

Preparation 34

(1S,2S,4S,5R,6R)-2-(1'-tert-Butoxycarbonyl-pyrrolidine-2'S-carbonyl)-4-hydroxy-bicyclo[3.1.0]hexane-2,6-dicarboxylic acid diethyl ester

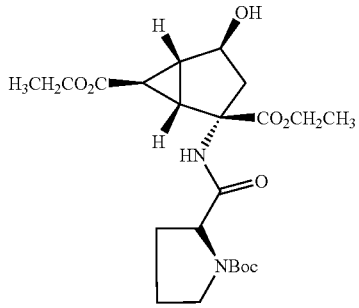

Prepare according to General Procedure A using Boc-L-Proline and (1S,2S,4S,5R,6R)-2-amino-4-hydroxy-bicyclo[3.1.0.]hexane-2,6-dicarboxylic acid diethyl ester (Preparation 22). Purify the crude material on 110 g of silica on an ISCO system eluting with a gradient of 80% ethyl acetate/hexanes to 100% ethyl acetate to afford 699 mg (84%) of the title compound.

$[\alpha]_D^{23}$=−52.53 (c=0.99, MeOH).

1H NMR (400 MHz, CD3OD) δ 1.26 (6H, m), 1.44 (9H, s), 1.62 (1H, m), 1.73 (1H, dd, J=5.4, 15.3 Hz), 1.84 (1H, m), 1.97 (1H, m), 2.07 (4H, m), 2.41 (1H, d, J=15.3 Hz), 2.50 (1H, m), 2.59 (1H, m), 4.12 (2H, m), 4.20 (1H, q, J=7.4 Hz), 4.27 (1H, d, J=5.4 Hz).

MS found 454.9 [M+H]+, 476.8 [M+Na]+.
HRMS calcd $C_{22}H_{34}N_2O_8Na$, 477.2213. Found, 477.2210

Preparation 35

(1S,2S,4S,5R,6R)-2-[2'S-tert-Butoxycarbonylamino-3'-(4-tert-butoxycarbonyloxy-phenyl)-propionylamino]-4-hydroxy-bicyclo[3.1.0]hexane-2,6-dicarboxylic acid diethyl ester

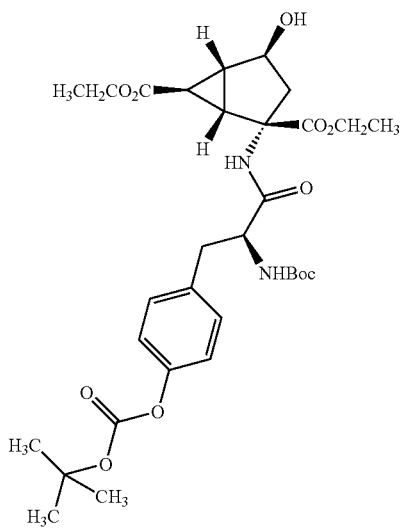

Prepare the title compound according to General Procedure A using 2S-tert-butoxycarbonylamino-3-(4-tert-butoxycarbonyloxy-phenyl)-propionic acid and (1S,2S,4S,5R,6R)-2-amino-4-hydroxy-bicyclo[3.1.0.]hexane-2,6-dicarboxylic acid diethyl ester (Preparation 22). Purify the crude material on 110 g of silica on an Isco system eluting with a gradient of 60% ethyl acetate/hexane to 90% ethyl acetate/hexanes to afford 1.09 g (91%) of the title compound.

$[\alpha]_D^{23}$=−12 (c=1.0, MeOH).

1H NMR (400 MHz, CD3OD) δ 1.25 (6H, m), 1.37 (9H, s), 1.52 (9H, s), 1.68 (1H, dd, J=5.4, 15.3 Hz), 2.06 (1H, m), 2.38 (1H, d, J=15.3 Hz), 2.64 (1H, m), 2.79 (1H, dd, J=8.4, 13.9 Hz), 3.05 (1H, dd, J=5.4, 13.9 Hz), 4.20 (6H, m), 7.04 (2H, d, J=8.4 Hz), 7.26 (2H, d, J=8.4 Hz).

MS found 621.8 [M+H]+, 643.8 [M+Na]+.
HRMS calcd for $C_{31}H_{44}N_2O_{11}Na$, 643.2843. Found, 643.2845.

Preparation 36

(1S,2S,4S,5R,6R)-2-(2'S-tert-Butoxycarbonylamino-4'-methylsulfanyl-butyrylamino)-4-hydroxy-bicyclo[3.1.0]hexane-2,6-dicarboxylic acid diethyl ester

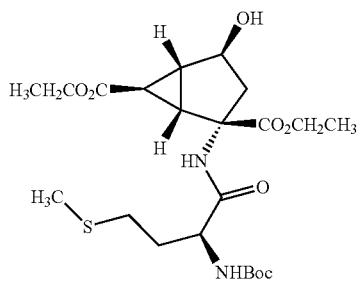

The title compound was prepared according to General Procedure A using (Boc-L-methionine) and (1S,2S,4S,5R,6R)-2-amino-4-hydroxy-bicyclo[3.1.0.]hexane-2,6-dicarboxylic acid diethyl ester (Preparation 22). The crude material was purified on 110 g of silica on an Isco system eluting with a gradient of 80% ethyl acetate/hexanes to 100% ethyl acetate to afford 1.0 g (92%) of the title compound.

$[\alpha]_D^{23}$=−30 (c=1.0, MeOH).

1H NMR (400 MHz, CD3OD) δ 1.26 (6H, m), 1.43 (9H, s), 1.84 (6H, m), 2.06 (1H, m), 2.2 (1H, m), 2.48 (1H, m), 2.61 (1H, m), 3.37 (1H, m), 2.49 (1H, m), 4.2 (6H, m).

MS found 488.8 [M+H]+, 510.8 [M+Na]+.
HRMS calcd for $C_{22}H_{36}N_2O_8SNa$, 511.2090. Found, 511.2071.

Preparation 37

(1S,2S,4S,5R,6R)-2-(2'S-tert-Butoxycarbonylamino-propionylamino)-4-hydroxy-bicyclo[3.1.0]hexane-2,6-dicarboxylic acid diethyl ester

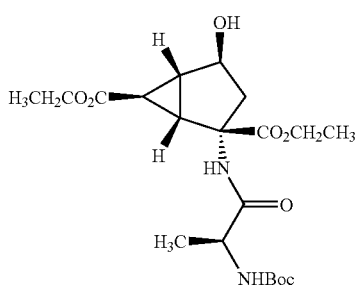

Prepare according to General Procedure A using commercially available N-BOC-(L)-Alanine and (1S,2S,4S,5R,6R)-2-amino-4-hydroxy-bicyclo[3.1.0.]hexane-2,6-dicarboxylic acid diethyl ester (Preparation 22). Reflux reaction mixture overnight. Purify by prep HPLC, 1×500 g $SiO_2$ column, (10% ethyl acetate/hexanes to 100% ethyl acetate). Yield 3.0 g (90%, 7.00 mmol) of a white foam.

$[\alpha]_D^{23}$=−32.31° (c=0.37, $CHCl_3$).

$^1$H NMR (300 MHz, $CDCl_3$) δ 1.28 (6H, t, J=7.3 Hz), 1.34 (3H, d, J=7.3 Hz), 1.46 (9H, s), 1.51-1.58 (2H, m), 1.64 (1H, s), 2.19 (1H, dd, J=3.3, 6.2 Hz), 2.40 (1H, dd, J=2.9, 6.2 Hz), 2.80 (1H, d, J=15.8 Hz), 4.10-4.36 (6H, m), 4.92 (1H, bs), 6.94 (1H, bs).

Anal Calcd for $C_{20}H_{32}N_2O_8 \cdot 0.1H_2O$: C, 55.83; H, 7.54; N, 6.51. Found: C, 55.57; H, 7.64; N, 6.44.

MS (ES) m/z 429.2 $[M+H]^+$, 329.1 $[M-Boc]^+$.

Preparation 38

(1S,2S,4S,5R,6R)-2-(2'S-amino-propionylamino)-4-hydroxy-bicyclo[3.1.0]hexane-2,6-dicarboxylic acid diethyl ester hydrochloride

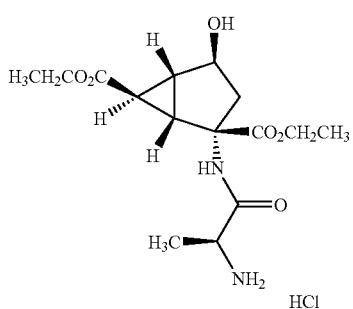

Purge a solution of (1S,2S,4S,5R,6R)-2-(2'S-tert-Butoxycarbonylamino-propionylamino)-4-hydroxy-bicyclo[3.1.0]hexane-2,6-dicarboxylic acid diethyl ester (2.95 g, 6.88 mmol, Preparation 37) in ethyl acetate (30 mL) at 0° C. with anhydrous HCl gas until the solution is saturated with HCl. Stir the resulting reaction mixture at 0° C. until the reaction is judged complete by TLC. Purge the reaction mixture for 30 minutes with $N_2$ to remove excess HCl gas. Concentrate the resulting suspension to dryness in vacuo to afford 2.47 g (98%, 6.78 mmol) of the desired amino hydrochloride salt. No further purification is necessary.

$[\alpha]_D^{23}$=−28.0° (c=0.50, MeOH).

$^1$H NMR (300 MHz, $CDCl_3$) δ 1.24 (3H, t, J=7.0 Hz), 1.28 (3H, t, J=7.3 Hz), 1.50 (3H, d, J=7.3 Hz), 1.61 (1H, t, J=2.9 Hz), 1.76 (1H, dd, J=5.9, 15.8 Hz), 2.10 (1H, dd, J=3.3, 5.9 Hz), 2.43 (1H, d, J=15.4 Hz), 2.60 (1H, dd, J=2.9, 6.2 Hz), 3.90 (1H, q, J=7.0, 13.9 Hz), 4.15 (2H, q, J=7.3 Hz), 4.14-4.31 (3H, m).

Anal Calcd for $C_{15}H_{24}N_2O_6 \cdot HCl \cdot 0.7H_2O$: C, 47.73; H, 7.05; N, 7.42. Found: C, 47.96; H, 6.91; N, 7.04.

MS (ES) m/z 329.1 $[M+H]^+$.

Preparation 39

(1S,2S,4S,5R,6R)-2-[2'S-(2S-tert-Butoxycarbonylamino-propionylamino)propionylamino]-4-hydroxy-bicyclo[3.1.0.]hexane-2,6-dicarboxylic acid diethyl ester

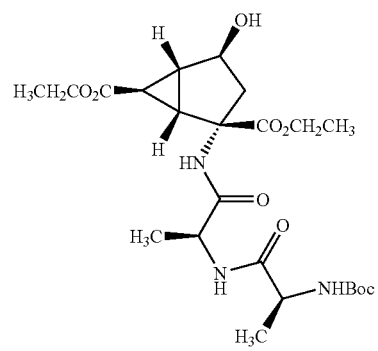

Prepare according to General Procedure A using (1S,2S,4S,5R,6R)-2-(2'S-amino-propionylamino)-4-hydroxy-bicyclo[3.1.0]hexane-2,6-dicarboxylic acid diethyl ester hydrochloride (0.2 g, 0.55 mmol, Preparation 38) and Boc-(L)-alanine (0.16 g, 0.82 mmol) with the exception that no DMAP is used. Purify using PC-TLC (ethyl acetate/hexanes) to yield 0.13 g (47.3%) of the title compound.

$[\alpha]_D^{23}$=−46.2 (c=0.52, $CHCl_3$).

$^1$H NMR (300 MHz, $CDCl_3$) δ 1.27 (3H, t, J=7.0 Hz), 1.28 (3H, t, J=7.0 Hz), 1.36 (3H, d, J=7.0 Hz), 1.37 (3H, d, J=7.0 Hz), 1.44 (9H, s), 1.58-1.65 (2H, m), 2.19 (1H, dd, J=3.0, 5.9 Hz), 2.46 (1H, dd, J=2.6, 5.9 Hz), 2.70 (1H, d, J=15.4 Hz), 4.09-4.33 (7H, m), 4.48 (1H, app p, J=7.0 Hz), 5.05 (1H, bd, J=6.6 Hz), 6.79 (1H, bd, J=7.7 Hz), 7.26 (1H, s).

HRMS calcd for $C_{23}H_{38}N_3O_9$, 500.2608. Found, 500.2598.

Preparation 40

(1S,2S,4S,5R,6R)-2-[2'S-(2-tert-Butoxycarbonylamino-acetylamino)-propionylamino]-4-hydroxy-bicyclo[3.1.0.]hexane-2,6-dicarboxylic acid diethyl ester

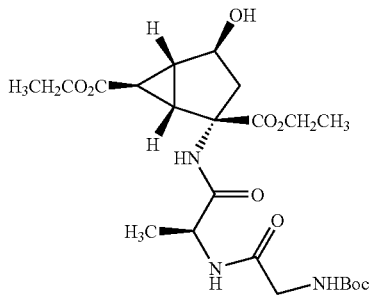

Prepare according to General Procedure A using Boc-glycine (0.29 g, 1.6 mmol) and (1S,2S,4S,5R,6R)-2-(2'S-amino-propionylamino)-4-hydroxy-bicyclo[3.1.0]hexane-2,6-dicarboxylic acid diethyl ester hydrochloride (0.4 g, 1.1 mmol, Preparation 38) with the exception that DMAP is not used. Purify using PC-TLC (ethyl acetate/hexanes) to yield 0.14 g (26.2%) of the title compound.

$[\alpha]_D^{23}$=–14 (c=1.00, CDCl$_3$).

$^1$H NMR (300 MHz, CDCl$_3$) δ 1.27 (3H, t, J=7.3 Hz), 1.29 (3H, t, J=7.3 Hz), 1.38 (3H, d, J=7.0 Hz), 1.45 (9H, s), 1.57-1.65 (2H, m), 2.19 (1H, dd, J=3.3, 5.9 Hz), 2.44 (1H, dd, J=2.9, 5.9 Hz), 2.74 (1H, d, J=15.8 Hz) 3.70-3.86 (2H, m), 4.08-4.34 (6H, m), 4.56 (1H, app p, J=7.0 Hz), 5.31 (1H, bs), 6.88 (1H, bd, J=7.0 Hz), 7.50 (1H, s).

HRMS calcd for C$_{22}$H$_{36}$N$_3$O$_9$, 486.2452. Found, 486.2444.

Preparation 41

(1S,2S,4S,5R,6R)-2-[2'-(2S-tert-Butoxycarbonylamino-4-methyl-pentanoylamino)-propionylamino]-4-hydroxy-bicyclo[3.1.0]hexane-2,6-dicarboxylic acid diethyl ester

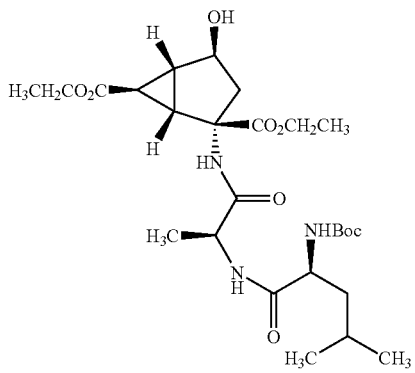

Prepare according to General Procedure B using commercially available N-BOC-(L)-leucine monohydrate and (1S,2S,4S,5R,6R)-2-(2'S-amino-propionylamino)-4-hydroxy-bicyclo[3.1.0]hexane-2,6-dicarboxylic acid diethyl ester hydrochloride (0.2 g, 0.55 mmol, Preparation 38). Purify by PC-TLC, 4 mm SiO$_2$ rotor, (10% ethyl acetate/hexanes to 100% ethyl acetate). Yield 0.54 g (62%, 1.00 mmol) of a white foam.

$[\alpha]_D^{23}$=–61.2° (c=0.49, MeOH).

$^1$H NMR (300 MHz, CDCl$_3$) δ 0.93 (3H, d, J=6.2 Hz), 0.94 (3H, d, J=6.2 Hz), 1.25 (3H, t, J=7.3 Hz), 1.27 (3H, t, J=7.3 Hz), 1.36 (3H, d, J=7.0 Hz), 1.43 (9H, s), 1.53 (1H, d, J=9.5 Hz), 1.55-1.69 (5H, m), 2.18 (1H, dd, J=2.9, 5.9 Hz), 2.44 (1H, dd, J=2.9, 6.2 Hz), 2.70 (1H, d, J=15.8 Hz), 4.06 (1H, bs), 4.13 (413, q, J=7.3 Hz), 4.18-4.28 (2H, m), 4.31 (1H, d, J=5.9 Hz), 4.41-4.45 (1H, m), 4.85 (1H, bs), 6.57 (1H, d, J=7.3 Hz), 6.97 (1H, bs).

Anal Calcd for C$_{26}$H$_{43}$N$_3$O$_9$.0.1H$_2$O: C, 57.46; H, 8.01; N, 7.73. Found: C, 57.18; H, 8.00; N, 7.64.

HRMS calcd for C$_{26}$H$_{13}$N$_3$O$_9$ [M+Na]$^+$, 564.2897. Found, 564.2922.

Preparation 42

(1S,2S,4S,5R,6R)-2-[2'-(2S-tert-Butoxycarbonylamino-3-methyl-butyrylamino)-propionylamino]-4-hydroxy-bicyclo[3.1.0]hexane-2,6-dicarboxylic acid diethyl ester

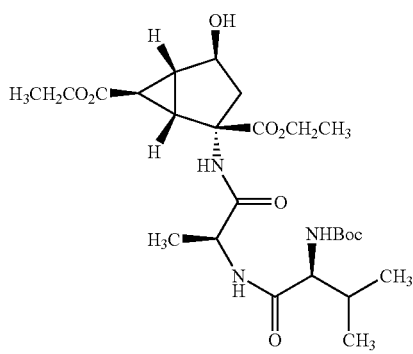

Prepare according to General Procedure B using commercially available N-BOC-(L)-Valine and (1S,2S,4S,5R,6R)-2-(2'S-amino-propionylamino)-4-hydroxy-bicyclo[3.1.0]hexane-2,6-dicarboxylic acid diethyl ester hydrochloride (0.2 g, 0.55 mmol, Preparation 38). Purify by PC-TLC, 4 mm SiO$_2$ rotor, (10% ethyl acetate/hexanes to 67% ethyl acetate). Yield 0.36 g (43%, 0.68 mmol) of a white foam.

$[\alpha]_D^{23}$=–65.5° (c=0.58, MeOH).

$^1$H NMR (300 MHz, CDCl$_3$) δ 0.91 (3H, d, J=7.0 Hz), 0.97 (3H, d, J=6.6 Hz), 1.27 (3H, t, J=7.3 Hz), 1.28 (3H, t, J=7.0 Hz), 1.37 (3H, d, J=17.3 Hz), 1.44 (9H, s), 1.54-1.61 (3H, m), 2.12-2.20 (2H, m), 2.42 (1H, dd, J=2.6, 5.9 Hz), 2.70 (1H, d, J=15.4 Hz), 3.90 (1H, t, J=6.6 Hz), 4.13 (2H, q, J=7.0 Hz), 4.20-4.29 (2H, m), 4.31 (1H, d, J=5.9 Hz), 4.40-4.48 (1H, m), 4.93 (1H, bs), 6.41 (1H, d, J=7.3 Hz), 6.91 (1H, bs).

Anal Calcd for C$_{25}$H$_{41}$N$_3$O$_9$.0.2CH$_2$Cl$_2$: C, 55.58; H, 7.66; N, 7.72. Found: C, 55.76; H, 7.27; N, 7.49.

MS (ES) m/z 528.3 [M+H]$^+$.

Preparation 43

(1S,2S,4S,5R,6R)-2-(2'S-Acetylamino-propionylamino)-4-hydroxy-bicyclo[3.1.0]hexane-2,6-dicarboxylic acid diethyl ester

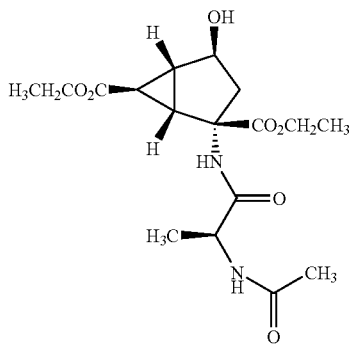

Stir a solution of (1S,2S,4S,5R,6R)-2-(2'S-amino-propionylamino)-4-hydroxy-bicyclo[3.1.0]hexane-2,6-dicarboxylic acid diethyl ester hydrochloride (0.30 g, 0.82 mmol, Preparation 38) in CH$_2$Cl$_2$ (30 mL) at 0° C. as triethylamine (0.16 g, 1.6 mmol) then acetyl chloride (0.10 g, 1.18 mmol) is added sequentially. Allow the reaction mixture to warm as it stirs overnight. Dilute the reaction mixture with ethyl acetate (700 mL) and wash with aqueous NaHSO$_4$ and brine. Dry the organic layer over magnesium sulfate. Purify by PC-TLC, 4 mm SiO$_2$ rotor, (10% ethyl acetate/hexanes to 100% ethyl acetate) to afford 0.24 g (79%, 0.65 mmol) of a white foam.

[α]$_D^{23}$=−48° (c=0.5, MeOH).

$^1$H NMR (300 MHz, CDCl$_3$) δ 1.27 (3H, t, J=7.3 Hz), 1.28 (3H, t, J=7.3 Hz), 1.37 (3H, d, J=7.0 Hz), 1.55-1.62 (2H, m), 1.99 (3H, s), 2.19 (1H, dd, J=3.3, 6.6 Hz), 2.40 (1H, dd, J=2.6, 5.9 Hz), 2.77 (1H, d, J=15.8 Hz), 4.07 (2H, q, J=7.0 Hz), 4.21-4.31 (2H, m), 4.33 (1H, d, J=6.2 Hz), 4.43-4.47 (1H, m), 6.13 (1H, bs), 7.06 (1H, bs).

Anal Calcd for C$_{17}$H$_{26}$N$_2$O$_7$: C, 55.13; H, 7.08; N, 7.56. Found: C, 55.05; H, 7.12; N, 7.29.

HRMS calcd for C$_{17}$H$_{26}$N$_2$O$_7$ [M+Na]$^+$, 393.1638. Found, 393.1644.

Preparation 44

3-acetoxy-2S-(tert-butoxycarbonylamino)propionic acid

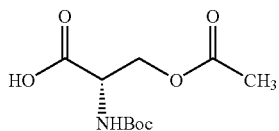

Add N-methyl morpholine (2.8 g, 27.2 mmoles) and di-tert-butyl dicarbonate (5.8 g, 25.2 mmoles) to a solution of O-acetyl-L-serine (3.7 g, 25.2 mmoles) in 1:1 dioxane:water. Stir the reaction for 24 hours then partition between ethyl acetate and water. Extract the aqueous with ethyl acetate and discard the organics. Adjust the pH to 0-1 with aqueous NaHSO$_4$. Extract the aqueous with ethyl acetate, dry over Na$_2$SO$_4$, filter, and concentrate in vacuo. Purify via flash chromatography yielding 2.6 g (41.7%). Material was used in Preparation 15 without characterization.

Preparation 45

(1S,5R)-3-(tert-Butoxycarbonylamino)-3-(tert-butoxycarbonyl)-6-oxabicyclo[3.1.0]hexane

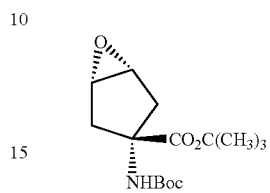

Add a solution of t-butyl methylmalonate (129 g, 0.75 mol) in THF (385 mL) to a slurry of LiH (14.9 g, 1.875 mol) in THF (900 mL) and N,N-dimethylpropylene urea (DMPU, 155 g, 1.2 mol) over 30 minutes while maintaining the temperature at 0-5° C. Heat the reaction mixture to 65° C. and add a solution of cis-1,4-dichloro-2-butene (95%, 100 g, 0.8 mol, 1.08 eq) in THF (100 mL) over 5.5 hours, maintaining the temperature at 63-67° C. Stir the reaction for 4 hours at 65° C. A water/MTBE work-up of the reaction mixture yields 1-(methoxycarbonyl)-1-(tert-butoxycarbonyl)cyclopent-3-ene.

$^1$H NMR (300 MHz, CDCl$_3$) δ 5.57 (s, 2H, CH=CH), 3.71 (s, 3H, CH$_3$), 2.95 (s, 4H, 2CH$_2$), 1.42 (s, 9H, C(CH$_3$)$_3$).

IR (film) 1734 (C=O), 1646, 1268, 1149 cm$^{-1}$.

Cool the reaction solution containing 1-(methoxycarbonyl)-1-(tert-butoxycarbonyl)cyclopent-3-ene to 10-15° C. and add to a cooled solution (10-15° C.) of 1 N NaOH (1.3 L, 1.3 mol) over 30 minutes. Stir the reaction solution at 25° C. for 24 hours and monitored by GC assay. When the hydrolysis reaction is complete, add MTBE (645 mL) to the reaction mixture and stir the solution for 5 minutes. Allow the layers to settle and separate. Discard the organic layer. Add 1.5 M NaHSO$_4$ solution (1470 mL) to make the aqueous layer acidic (pH 2-3). Add MTBE (1.3 L) and separate the layers. Extract the aqueous layer with MTBE (385 mL) and wash the combined organic layers with 5% LiCl solution. Concentrate the organic layer under vacuum and dilute with heptane (780 mL). Concentrate the solution to approximately 500 mL and stir the resulting slurry 1 hour at ambient temperature. Filter the solid, wash with heptane (250 mL), and vacuum dry at 35° C. to give 103.29 g (61% yield) of 1-(carboxylic acid)-1-(tert-butoxycarbonyl)cyclopent-3-ene as a white solid.

mp=119° C.

$^1$H NMR (300 MHz, CDCl$_3$), δ 5.61 (s, 2H, CH=CH), 3.00 (s, 4H, 2CH$_2$), 1.46 (s, 9H, C(CH$_3$)$_3$).

IR: 3800-3000 (br, COOH), 1741 (CO$_2$R), 1705 (CO$_2$H), 1283), 1149 cm$^{-1}$.

Dissolve 1-(carboxylic acid)-1-(tert-butoxycarbonyl)cyclopent-3-ene (50 g, 236 mmol) in 850 mL of 70:30 toluene:MTBE under nitrogen in a 1 L flask with mechanical stirrer. Add thionyl chloride (33.6 g, 283 mmol, 1.2 equiv) to the stirred reaction mixture, maintaining the temperature at 23° C. Cool the reaction solution to 0-5° C. and add triethylamine (32.2 g, 318 mmol, 1.35 equiv) dropwise over 30 minutes. Warm the reaction mixture to 23° C. and stir for 1 hour. Add the reaction mixture rapidly dropwise to deionized water (625 mL), maintaining the temperature at 20-25° C. Separate the layers and wash the organic layer with 500 mL 1 M NaHCO$_3$ solution. Concentration of the organic layer isolates 1-(chlorocarbonyl)-1-(tert-butoxycarbonyl)cyclopent-3-ene as a light yellow liquid.

$^1$H NMR (300 MHz, CDCl$_3$) δ 5.61 (s, 2H, CH=CH), 3.04 (app q, J=15.1 Hz, 4H, 2CH$_2$), 1.49 (s, 9H, C(CH$_3$)$_3$).

IR (film) 1796 (COCl), 1743 (CO$_2$R), 1274, 1233, 1158 cm$^{-1}$.

Add a solution of tetrabutyl ammonium hydrogen sulfate (0.81 g, 2.4 mmol) in deionized water (700 mL) to sodium azide (20.16 g, 310 mmol). Add the solution containing 1-(chlorocarbonyl)-1-(tert-butoxycarbonyl)cyclopent-3-ene in MTBE/toluene to the azide solution over 45 minutes. Stir the reaction mixture for 3 hours at 23° C. until the 1-(chlorocarbonyl)-1-(tert-butoxycarbonyl)cyclopent-3-ene is consumed, as confirmed by GC analysis of the reaction solution. Separate the layers and wash the organic layer with 1 M NaHCO$_3$ (540 mL) and deionized water (540 mL, then 270 mL). Dry the organic layer with Na$_2$SO$_4$ and filter. Concentrate the solution under vacuum to yield 1-(acyl azide)-1-(tert-butoxycarbonyl)cyclopent-3-ene as as an oil.

$^1$H NMR (300 MHz, CDCl$_3$) δ 5.58 (s, 2H, CH=CH), 2.96 (app t, J=2.3 Hz, 4H, 2CH$_2$), 1.46 (s, 9H, C(CH$_3$)$_3$).

IR (film) 2137 (CON$_3$), 1720 (CO$_2$R), 1246 (s, 1185, 1136 cm$^{-1}$.

Add the solution of 1-(acyl azide)-1-(tert-butoxycarbonyl)cyclopent-3-ene over 1 hour to 110 mL of toluene at 95° C. Evolution of nitrogen gas is addition rate controlled under these conditions. Distill MTBE from the reaction during the addition. Stir the reaction for 1 hour at 95° C., and allow to cool to 23° C. overnight. Concentration of the solvent under vacuum yields 1-(isocyanate)-1-(tert-butoxycarbonyl)cyclopent-3-ene as an oil.

$^1$H NMR (300 MHz, CDCl$_3$) δ 5.67 (s, 2H, CH=CH), 3.01 (d, J=15.6 Hz, 2H), 2.61 (d, J=15.6 Hz, 2H), 1.50 (s, 9H, C(CH$_3$)$_3$).

IR (film) 2258 (—NCO), 1732 (—CO$_2$R), 1157 cm$^{-1}$.

Add t-butanol (35 g, 471 mmol) to a solution of potassium t-butoxide (1M in THF, 471 mL, 471 mmol) under nitrogen. Cool the reaction solution was cooled to 0-5° C. and add the toluene solution containing 1-(isocyanate)-1-(tert-butoxycarbonyl)cyclopent-3-ene over 60 minutes, maintaining the temperature at 0-10° C. Warm the reaction to 23° C., stir for 2 hours, and assay by GC for the disappearance of the isocyanate starting material. Add the reaction mixture to a mixture of deionized water (1.2 L) and MTBE (1.2 L) at 15° C. Stir the solution for 20 minutes and separate the layers. Wash the organic layer with a 20% brine solution (250 mL) and separate the layers. Transfer the organic layer concentrated via distillation, to approximately 250 mL. Add heptane (500 mL) and concentrate the solution to a total volume of 250 mL. Cool the resulting slurry solution to 0° C., stir for 2 hours, and filter. Wash the filter cake with cold heptane (2×100 mL) and vacuum dry to give 34.54 g (52% yield from 1-(carboxylic acid)-1-(tert-butoxycarbonyl)cyclopent-3-ene) of 1-(tert-butoxycarbonylamino)-1-(tert-butoxycarbonyl)cyclopent-3-ene as a white solid.

m.p. 87-89° C.

$^1$H NMR (500 MHz, CDCl$_3$) δ 5.63 (s, 2H, CH=CH), 5.1 (bs, $^1$H, NH), 2.99 (d, J=17.2 Hz, 2H), 2.57 (d, J=16.0 Hz, 2H), 1.46 (s, 9H), 1.44 (s, 9H).

$^{13}$C NMR (CDCl$_3$) δ 173.3, 154.9, 127.7, 81.1, 64.5, 44.8, 28.3, 27.8.

IR (KBr): 3451, 2981, 2932, 1712, 1489, 1369, 1154 cm$^{-1}$.

MS (FIA) m/e (% relative intensity) 284.2 (M$^+$+1, 56), 228.2 (73), 172.1 (97), 128.0 (100).

Add a solution of 1-(tert-butoxycarbonylamino)-1-(tert-butoxycarbonyl)cyclopent-3-ene (20.00 g, 71 mmol) in 100 mL of EtOAc to a mixture of tetrabutylammonium hydrogensulfate (4.08 g, 10 mmol, 0.17 equiv), magnesium monoperoxyphthalate hydrate (MMPA, 52.4 g, 4.76% active oxygen=2.1 equiv), and deionized water (100 mL). Stir the reaction was stirred with a mechanical stirrer for 19 hours. Add a solution of sodium sulfite (18 g) in deionized water (100 L) to the reaction mixture over 30 minutes. Dilute the mixture with 100 mL of EtOAc and separate the layers. Wash the organic layer with deionized H$_2$O (100 mL), 2N NaOH (2×100 mL), and deionized H$_2$O (2×100 mL). Distill the organic layer at 75-90° C. at atmospheric pressure until the volume reaches 40 mL. Cool the solution to 75° C. and add hot heptane (120 mL). Cool the solution to 65° C. and optionally seed with the desired product. Allow the resulting slurry to cool to ambient temperature and then cool in an ice bath for 1 hour. Filter the product and wash with 80 mL of cold 4:1 heptane:EtOAc, then vacuum dry at 40° C. to obtain 15.45 g (73% yield) of the title compound as a white solid. The compound may be further purified by recrystallization from 2:1 isopropanol:water.

m.p. 130-133° C.

$^1$H NMR (500 MHz, CDCl$_3$) δ 5.0 (bs, 1H), 3.58 (s, 2H), 2.41 (d, J=15.3 Hz, 2H), 2.20 (d, J=15.2 Hz, 2H), 1.43 (s, 9H), 1.40 (s, 9H).

$^{13}$C NMR (CDCl$_3$) δ 171.3, 154.3, 81.2, 79.5, 62.8, 57.0, 38.6, 28.3, 27.7.

IR (KBr): 3453, 2982, 2932, 1726, 1708, 1489, 1369, 1293, 1156, 840 cm$^{-1}$.

MS (FIA) m/e (% relative intensity) 300.3 (M$^+$+1, 65), 244.4 (68), 188.2 (100) 144.1 (99).

Preparation 46

(1R,3R)-1,3-Di(methylbenzylamino)propane dihydrochloride

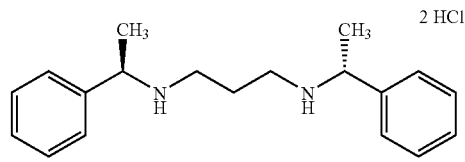

Heat (R)-α-methylbenzylamine (98% ee, 121 g, 1 mol) to 100° C. under nitrogen. Add dibromopropane (25.4 mL, 50.5 g, 250 mmol) dropwise over 70 min. Heat the mixture for another 3 hours and then cool to 80° C. Add concentrated (50%) NaOH solution (30 mL) dropwise over 10 minutes. Add water (30 mL) to dissolve the solids and allow the mixture to cool to room temperature over 30 minutes. Add MTBE (100 mL). Dissolve the precipitate by adding 100 mL of water, and separate the layers. Wash the organic layer with 50 mL of brine, dry (Na$_2$SO$_4$), and concentrate under vacuum to give 126.0 g of light yellow oil. Distill the oil under vacuum at 70° C. (head temperature), using a 12-inch column, to remove excess (R)-α-methylbenzylamine. Dissolve the pot residue (68 g of crude diamine) in 1 L of i-PrOH in a 2 L flask with a mechanical stirrer. Add concentrated HCl (12 M, 45 mL, 540 mmol) dropwise over 10 minutes. Add an additional 100 mL of i-PrOH to ensure thorough mixing of the thick slurry. Stir the mixture for 90 minutes and filter. Wash the cake with i-PrOH and vacuum dry at 40° C. to obtain 64.32 g (72% yield, based on dibromopropane) of the title compound as a white solid.

¹H NMR (500 MHz, DMSO-d₆) δ 9.93 (bs, 2H), 9.47 (bs, 2H), 7.56 (d, J=7.0 Hz, 4H), 7.37 (m, 6H), 4.27 (m, 2H), 2.84 (m, 2H) 2.48 (m, 2H), 2.1 (m, 2H), 1.56 (d, J=6.7 Hz, 6H).

Preparation 47

(1S)-1-(tert-Butoxycarbonylamino)-1-(tert-butoxycarbonyl)-cyclopnt-4-en-3-one

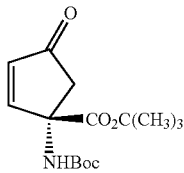

Dissolve (1R,3R)-1,3-di(methylbenzylamino)propane dihydrochloride (24.65 g, 69.3 mmol, Preparation 46) in 150 mL of water with stirring. Add to the solution 35 mL (175 mmol) of 5 N NaOH solution, followed by 150 mL of MTBE. After stirring 15 minutes, separate the layers and extract the aqueous layer with 100 mL of MTBE. Wash the combined organic layers with 100 mL of brine, dry with Na₂SO₄, and concentrate under vacuum to give 18.06 g (92% yield) of 1R,3R-di(methylbenzylamino)propane as a colorless oil.

In a 500 mL four-neck flask with overhead stirrer, dissolve 20.59 g (73.5 mmol) of 1R,3R-di(methylbenzylamino)propane in 30 mL each of dry MTBE and THF, under N₂ flow. Cool the solution to 45° C. and add 59 mL (147 mmol) of n-BuLi solution (2.5 M in hexanes) dropwise over 17 minutes. Stir the light yellow solution for 2 hours at −45° C. Add a solution of (1S,3S,5R)-3-(tert-butoxycarbonylamino)-3-(tert-butoxycarbonyl)-6-oxabicyclo[3.1.0]hexane (10.00 g, 33.4 mmol) in 55 mL of dry THF dropwise over 28 minutes, keeping the temperature below 40° C. Rinse the addition funnel with an additional 5 mL of THF. Stir the reaction mixture for 18 hours at 45° C. and then quench via the dropwise addition of 4 N aqueous sulfuric acid (75 mL). Remove the cooling bath after the acid addition is complete. Separate the layers and extract the aqueous layer with 50 mL of MTBE. Wash the combined organic layers with 50 mL each of water and brine, dry with Na₂SO₄, and concentrate under vacuum to give 9.78 g of crude 578242 as a white solid. Dissolve the solid in 33 mL of hot MTBE and add heptane (66 mL) portionwise. Allow the stirred solution to cool to room temperature, then stir the mixture for 1 hour at 0° C. Filter the solid, wash with 2×10 mL of cold 2:1 heptane:MTBE, and vacuum dry for 4 hours at 35° C. to provide 8.52 g (85% yield) of (1S,3R)-1-(tert-butoxycarbonylamino)-1-(tert-butoxycarbonyl)-3-hydroxycyclopent-4-ene as a white solid.

m.p. 111-112 C.

Chiral HPLC assay: 99.7% ee.

$[\alpha]_D$=+114 (c 1, MeOH).

¹H NMR (500 MHz, CDCl₃) δ 6.1 (bs, 1H), 5.9 (bs, 1H), 5.55 (d, J=5.0 Hz, 1H), 4.8 (m, 1H), 4.44 (d, J=10.5 Hz, 1H), 2.87 (dd, J=14.5, 7.5 Hz, 1H), 2.00 (d, J=14.5 Hz, 1H), 1.45 (s, 9H), 1.42 (s, 9H).

IR (KBr): 3413, 2983, 1703, 1491, 1370, 1309, 1255, 1155, 1055 cm⁻¹.

MS (FIA) m/e (% relative intensity) 300.3 (M⁺+1, 15), 226.2 (29), 170.1 (100), 126.1 (89), 108.3 (20).

Add 2,2,6,6-tetramethyl-1-piperidinyloxy (free radical) (TEMPO) (0.84 g, 5.3 mmol) and KBr (0.63 g, 5.3 mmol, in 2 mL of water) to a solution of (1S,3R)-1-(tert-butoxycarbonylamino)-1-(tert-butoxycarbonyl)-3-hydroxycyclopent-4-ene (20 g, 66.8 mmol) in MTBE (200 mL). Cool the reaction mixture to 0° C. and add a solution of NaOCl (3.14%, 240 g, 100 mmol) containing NaHCO₃ (8.4 g) dropwise, keeping the temperature below 5° C. Stir the reaction 1 hour at 0° C. and allow to warm to room temperature. Separate the layers and extract the aqueous layer with MTBE (2×200 mL). Wash the combined organic layers with 200 mL of 1N HCl solution containing 2.21 g of KI followed by 10% Na₂SO₃ solution (200 mL). Wash the organic layer with water (2×200 mL) and concentrate to dryness under vacuum. Dissolve the crude product in MTBE (60 mL) at 50° C. and crystallize by addition of heptane (200 mL) over 1 h. Cool the mixture was cooled to 0° C. over 2 hours and then filter. Wash the filter cake with 100 mL of cold heptane:MTBE (65:35) and vacuum dry to give 16.99 g (89% yield) of the title compound as a white solid.

m.p. 116-18° C.

$[\alpha]_D$=+123 (c 1, MeOH).

¹H NMR (500 MHz, CDCl₃) δ 7.4 (bs, 1H), 6.32 (d, J=5.5 Hz, 1H), 5.6 (bs, 1H), 2.87 (d, J=18.2 Hz, 1H), 2.9 (d, J=18.2 Hz, 1H), 1.43 (s, 18H). ¹³C NMR (CDCl₃) δ 206.1, 170.2, 160.8, 154.9, 136.1, 84.5, 66.1, 46.6, 28.9, 28.4.

IR (KBr): 3419, 2983, 1722, 1487, 1730, 1300, 1259, 1151, 1012 cm⁻¹.

MS (FIA) m/e (% relative intensity) 254.2 (M⁺+1, 11), 242.3 (18), 228.2 (13), 186.1 (76), 143.2 (11), 242.3 (100).

Preparation 48

1-(2-tert-butoxy-2-oxoethyl)tetrahydrothiophenium bromide

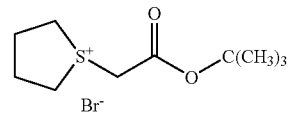

Add t-butyl bromoacetate (2.44 L, 16.52 mole, 1 eq) to a solution of tetrahydrothiophene (2.19 L, 24.8 mole, 1.5 eq) in acetone (11.38 L), in a 22 L flask over 30-60 minutes while maintaining the temperature between 15-25° C. using a water bath. Stir the reaction for 22 hours and assay a sample by ¹H NMR to confirm the completion of the reaction. Filter the precipitate, wash with acetone (2 L), and vacuum dry for 3 days at 28-33° C. to give 4.328 Kg (92.5% yield) of the title compound.

¹H NMR (500 MHz, DMSO d-6) δ 4.40 (s, 1H), 3.51 (m, 2H), 3.48 (m, 2H), 2.23 (m, 2H), 2.13 (M, 2H), 1.42 (s, 9H).

Preparation 49

(1S,2S,5R,6R)-2-(tert-Butoxycarbonylamino)-4-oxo-bicyclo[3.1.0]hexane-2,6-dicarboxylic acid di-tert-butyl ester

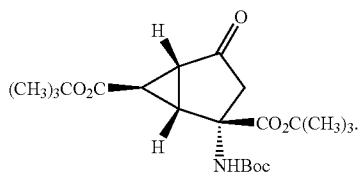

Add KOtBu (42 mL, 42 mmol, 1 M solution in THF, 2.5 equiv) to a 0° C. solution of 1-(2-tert-butoxy-2-oxoethyl)tetrahydrothiophenium bromide (11.9 g, 42 mmol, 2.5 equiv., Preparation 48) in acetonitrile (30 mL) under $N_2$ over 10 minutes keeping the temperature below 5° C. Stir the milky solution cold for 1.5 hours. Add trifluoroethanol (6.9 g, 69 mmol, 4.1 equiv) dropwise. Add a solution of (1S)-1-(tert-butoxycarbonylamino)-1-(tert-butoxycarbonyl)-cyclopent-4-en-3-one (5 g, 16.8 mmol, Preparation 47) and trifluoroethanol (13.3 g, 132 mmol, 7.9 equiv) in acetonitrile (20 mL), over 5 minutes, maintaining the temperature at 3-5° C. Stir the solution for 4.5 hours at 0-5° C. Add MTBE (155 mL) and 120 (80 mL) to the cold reaction mixture. Separate the layers and wash the organic layer with $H_2O$ (50 mL), then 20% brine (50 mL). Concentrate the organic layer via atmospheric pressure distillation to approximately 30 mL. Add heptane (100 mL) and concentrate the solution. Add additional heptane as needed until the vapor temperature of the distillate reaches 93° C. Add THF (65 mL) to yield a solution of the title compound.

Preparation 50

(1S,2S,5R,6R)-2-(tert-Butoxycarbonylamino)-4-oxo-bicyclo[3.1.0]hexane-2,6-dicarboxylic acid di-tert-butyl ester Add 1.7 L of saturated aqueous $K_2CO_3$ solution to a 0° C. solution of 1-(2-tert-butoxy-2-oxoethyl)tetrahydrothiophenium bromide (757 g, 2.67 mol, Preparation 48) in 2.2 L of $CH_2Cl_2$, keeping the temperature below 10° C. After stirring the biphasic mixture 1.5 hours, add 223 mL of 50% NaOH solution portionwise, keeping the temperature below 5° C. Stir the mixture 3 hours and filter. Rinse the salts with $Cl_2Cl_2$. Separate the layers and extract the aqueous layer with 600 mL of $CH_2Cl_2$. Dry the combined organic layers over solid $K_2CO_3$ and concentrate under vacuum to give 533.3 g (98% yield) of (2-tert-butoxy-2-oxoethyl)tetrahydrothiophenium as a pale yellow oil. Upon storage in the freezer, the oil crystallizes giving an off-white solid.

mp 48-50° C.

$^1$H NMR (500 MHz, $CDCl_3$) δ 3.12 (m, 2H), 3.00 (m, 2H), 2.85 (s, 1H), 2.41 (m, 2H), 1.84 (m, 2H), 1.38 (s, 9H).

Add 474 mL (6.5 mol, 10 equiv) of trifluoroethanol to a 0° C. solution of (1S)-1-(tert-butoxycarbonylamino)-1-(tert-butoxycarbonyl)-cyclopent-4-en-3-one (194 g, 653 mmol) in 650 mL of $CH_2Cl_2$. Add a solution of (2-tert-butoxy-2-oxoethyl)tetrahydrothiophenium (396 g, 1.96 mol) in 325 mL $CH_2Cl_2$ dropwise over 40 minutes keeping the temperature below 10° C. Remove the ice bath after 1 hour. Add deionized water (680 mL) and separate the layers. Extract the aqueous layer with 400 mL $CH_2Cl_2$. Wash the combined organic layers with 500 mL of brine, dry with $Na_2SO_4$, and concentrate under vacuum to obtain 587 g of an amber, oily solid. Dissolve the solid in 400 mL of $CH_2Cl_2$ and elute through a 1.6 Kg silica gel plug using 5:1:1 hexanes:methyl t-butylether:$CH_2Cl_2$ as eluent to yield a total of 13.2 L of eluent. Concentrate the eluent to give 398.7 g of white solid. Dissolve the solid in 3 L of refluxing 70:30 hexanes:MTBE. Allow the solution to cool to room temperature overnight, then cool in an ice bath for 1 hour. Filter the solid, rinse with cold solvent (approximately 700 mL), and vacuum dry at 35° C. to obtain 173 g (64% yield) of (1S,2S,5R,6R)-2-(tert-butoxycarbonylamino)-4-oxo-bicyclo[3.1.0]hexane-2,6-dicarboxylic acid di-tert-butyl ester as a white solid.

mp 144-46° C.

$[\alpha]_D$=+30.5 (c 1, $CHCl_3$).

$^1$H NMR (500 MHz, $CDCl_3$) δ 5.36 (d, 1H), 2.88 (m, 1H), 2.64 (dd, J=5.2, 3.2 Hz, 1H), 2.37 (d, J=2.7 Hz, 1H), 2.23 (bs, 1H), 1.45 (s, 9H), 1.43 (s, 18H).

$^{13}$C NMR (125 MHz, $CDCl_3$) δ 206.2, 171.2, 168.5, 155.3, 83.4, 82.7, 80.7, 61.2, 43.2, 36.0, 34.3 28.4, 28.2, 28.0, 25.3.

IR ($CHCl_3$): 2982, 1744, 1719, 1485, 1394, 1309 $cm^{-1}$.

MS (ES+) m/e (% relative intensity) 412.2 ($M^+$+1, 79), 356.2 (50), 300.1 (97), 276.1 (68), 244.1 (100). Anal. Calcd. for $C_{21}H_{33}NO_7$ (411.29): C, 61.30; H, 8.08; N, 3.40. Found: C, 61.32; H, 8.04; N, 3.51.

Preparation 51

(1S,2S,4S,5R,6R)-2-(tert-Butoxycarbonylamino)-4-hydroxy-bicyclo[3.1.0]hexane-2,6-dicarboxylic acid di-tert-butyl ester

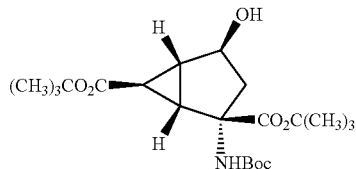

Cool the solution from Preparation 49 to 0° C. under nitrogen and add lithium tri-sec-butylborohydride (L-Selectride™, 1 M in THF, 21 mL, 21 mmol) dropwise. Stir the reaction mixture for 45 minutes at 0° C. Add a solution of 2 M sodium carbonate (31 mL) dropwise, keeping the temperature below 8° C. Add a solution of 30% $H_2O_2$ (7.15 g, 63 mmol) in 20 mL of water, keeping the temperature below 15° C. After stirring 10 min, add MTBE (210 mL) and deionized water (100 mL). Separate the layers were separated and wash the organic layer with saturated $Na_2SO_3$ solution (40 mL) and 1M $NaHSO_4$ solution (40 mL). Concentrate the organic layer by distillation at atmospheric pressure to a volume of approximately 90 mL. Continue the distillation and add heptane to maintain a constant volume. When the vapor temperature of the distillate reaches 93° C., cool the solution to 70° C. and add 7 mL of THF. Cool the solution to 0° C. and stir for 1 hour. Filter the solid, wash with cold heptane (10 mL), and vacuum dry at 50° C. to obtain 4.68 g (67% yield) of (1S,2S,4S,5R,6R)-2-(tert-butoxycarbonylamino)-4-hydroxy-bicyclo[3.1.0]hexane-2,6-dicarboxylic acid di-tert-butyl ester as a white solid.

m.p. 187-88° C.

$^1$H NMR ($CDCl_3$, 500 MHz) δ 5.31 (bs, 1H), 4.38 (d, $J_{AB}$=10.5 Hz, 1H), 4.30 (dd, J=11.0, 6.0 Hz, 1H), 2.68 (d,

J=15.3 Hz, 1H), 2.17 (m, 1H), 2.07 (m, 1H), 1.58 (m, J=15.2 Hz, 1H), 1.45 (s, 9H), 1.44 (s, 9H), 1.43 (s, 9H).

$^{13}$C NMR (75 MHz, CDCl$_3$) δ 175.2, 170.5, 155, 83.2, 81.3, 80.1, 73.7, 66.9, 43.1, 36.0, 34.4, 29.3, 28.3, 28.1, 27.4, 22.1.

IR (CHCl$_3$): 3445, 2982, 1714, 1485, 1361 cm$^{-1}$.

MS (ES+) m/e (% relative intensity) 414.2 (M$^+$+1, 58), 358.1 (75), 302.1 (78), 246.0 (100).

[α]$_D$=−28.6 (c 1, MeOH).

Preparation 52

(1R,2S,4R,5R,6R)-2-(2'S-2'-(tert-Butoxycarbonylamino)propionyl)amino-4-fluoro-bicyclo[3.1.0]hexane-2,6-dicarboxylic acid

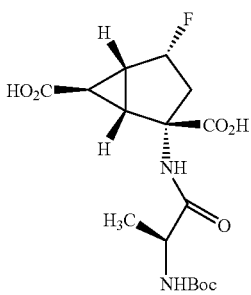

Add a solution of (1S,2S,4S,5R,6R)-2-(tert-butoxycarbonylamino)-4-hydroxy-bicyclo[3.1.0]hexane-2,6-dicarboxylic acid di-tert-butyl ester (25.00 g, 60.5 mmol, Preparation 51) in CH$_2$Cl$_2$ (230 mL) to a −78° C. solution of Deoxofluor™ (16.05 g, 72.6 mmol, 1.2 equiv) in CH$_2$Cl$_2$ (105 mL) over 2 h. Stir the reaction mixture for 1.5 hours, and add an additional 1.66 g of Deoxofluor™. Stir the solution 30 minutes and allow to warm to −10° C. Add a solution of saturated NaHCO$_3$ (105 mL) dropwise over 20 minutes, keeping tire temperature below 5° C. Adjust the pH of the aqueous layer to 7 by adding 160 mL of saturated NaHCO$_3$ solution. Allow the mixture to warm to ambient temperature and separate the layers. Extract the aqueous layer with 100 mL of CH$_2$Cl$_2$. Wash the combined organic layers with 250 mL of brine, then dry with Na$_2$SO$_4$. Remove the solvent under vacuum and add heptane (75 mL) to the crude product. Heat the resulting mixture to 50° C. until all solids are dissolved and stir at ambient temperature for 24 hours. Cool the mixture to 0° C. in an ice bath and filter. Rinse the product with cold heptane and vacuum dry to give 20.23 g (80% yield) of (1R,2S,4R,5R,6R)-2-(tert-butoxycarbonylamino)-4-fluoro-bicyclo[3.1.0]hexane-2,6-dicarboxylic acid di-tert-butyl ester as a white solid.

m.p. 140-143° C.

[α]$_D$=+20.6 (c 1, CHCl$_3$).

$^1$H NMR (CDCl$_3$, 500 MHz) δ 5.45 (dd, J$_{H-F}$=56, J$_{H-H}$=4.8 Hz, 1H), 5.28 (bs, 1H), 3.00 (m, 1H), 2.23 (bs, 1H), 2.11 (m, 1H), 2.08 (m, 1H), 1.46 (s, 9H), 1.45 (s, 9H), 1.43 (s, 9H), 1.37 (m, 1H).

$^{13}$C NMR (CDCl$_3$, 75 MHz) δ 177.7, 170.5, 155.0, 94.4, 92.0, 82.2, 81.5, 80.2, 64.7, 37.7, 33.2, 29.7, 29.3, 28.3, 28.1, 27.8, 20.4.

MS (ES+) m/e (% relative intensity) 416.2 (M$^+$+1, 66), 360.1 (67), 304.1 (100), 248.0 (60).

IR (CHCl$_3$): 3444, 2981, 1715, 1485, 1369 cm$^{-1}$.

Add SOCl$_2$ (21.29 g, 13.05 mL, 0.179 mole, 5 eq) to a solution of (1R,2S,4R,5R,6R)-2-(tert-butoxycarbonylamino)-4-fluoro-bicyclo[3.1.0]hexane-2,6-dicarboxylic acid di-tert-butyl ester (14.87 g, 0.036 mole) in EtOH (abs, 149 mL) dropwise over 10 minutes without cooling to produce a gently refluxing solution. Reflux the solution overnight. Remove the solvent from the reaction under vacuum. Dissolve the residue in EtOAc (150 mL) and add a solution of 10% Na$_2$CO$_3$ (75 mL) dropwise over 5-10 minutes with stirring. Separate the layers and extract the aqueous layer with EtOAc (50 mL). Wash the combined organic extracts with brine (1×50 mL), dry over Na$_2$SO$_4$, filter and concentrate the product, (1R,2S,4R,5R,6R)-2-amino-4-fluoro-bicyclo[3.1.0]hexane-2,6-dicarboxylic acid diethyl ester, in vacuo to a thick liquid which solidifies upon standing (11.02 g).

Add N-methylmorpholine (22.44 mL, 204 mmol) to a solution of N-Boc-L-alanine (38.62 g, 204 mmol) in 396 mL of methylene chloride at −22° C. under nitrogen, followed by the addition of iso-butyl chloroform are (26.48 mL, 204 mmol) dropwise over 15 minutes such that the reaction temperature does not exceed −18° C. Stir the resultant thin slurry at −20° C. for 30 minutes, then add a solution of (1R,2S,4R,5R,6R)-2-amino-4-fluoro-bicyclo[3.1.0]hexane-2,6-dicarboxylic acid diethyl ester (49.46 g, 191 mmol) in 247 mL of methylene chloride over 40 minutes such that the reaction temperature does not exceed −16° C. Remove the reaction from the cooling bath and stir at ambient temperature for 70 minutes. Add 408 mL of 1 N hydrochloric acid, stir for 5 minutes, and separate the layers. Wash the organic layer with saturated aqueous sodium bicarbonate (1×408 mL), dry (Na$_2$SO4), filter, and concentrate the product, (1R,2S,4R,5R,6R)-2-(2'S-2'-(tert-butoxycarbonylamino)propionyl)amino-4-fluoro-bicyclo[3.1.0]hexane-2,6-dicarboxylic acid diethyl ester, in vacuo to a white foam (88.16 g).

Add 46.7 mL (93.4 mmol) of 2N sodium hydroxide to a solution of crude (1R,2S,4R,5R,6R)-2-(2'S-2'-(tert-butoxycarbonylamino)propionyl)amino-4-fluoro-bicyclo[3.1.0]hexane-2,6-dicarboxylic acid diethyl ester (17.5 g, 37.3 mmol theoretical) in 46.6 mL of tetrahydrofuran at room temperature. Stir the biphasic mixture vigorously at room temperature until homogeneous, then stir for another hour (three hours total). Dilute the mixture with 46 mL of 1-butyl methyl ether, then mix for 10 minutes and separate the layers. In a separate flask, add 93 mL of water, then 8.4 mL (101 mmol) of concentrated HCl. Optionally add (1R,2S,4R,5R,6R)-2-(2'S-2'-(tert-butoxycarbonylamino)propionyl)amino-4-fluoro-bicyclo[3.1.0]hexane-2,6-dicarboxylic acid seed crystals to the acid solution, followed by the aqueous layer from above. Add the aqueous layer slowly at first, so that a moderately thick slurry forms. At this time, increase the rate of addition (40 minutes total addition time). Rinse the addition funnel with water (16 mL). Stir the resultant slurry for 2 hours, filter, wash with water (2×32 mL), and vacuum dry at 45° C. to constant weight to provide 13.9 g (99%) of the title compound as a white solid.

Preparation 53

(1R,4S,5S,6S)-4-Amino-2,2-dioxo-2λ²-thia-bicyclo[3.1.0]hexane-4,6-dicarboxylic acid diethyl ester

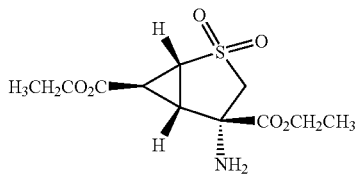

Add thionyl chloride to a slurry of (1R,4S,5S,6S)-4-Amino-2,2-dioxo-2λ⁶-thia-bicyclo[3.1.0]hexane-4,6-dicarboxylic acid (10 g, 42.5 mmol, U.S. Pat. No. 5,688,826) in 100 mL of 2B ethanol at room temperature (15.5 mL, 212.6 mmol) dropwise over 20 minutes followed by rinsing with 40 mL of ethanol. Beat the slurry to reflux and stir overnight. Cool the resultant solution to room temperature and concentrate to a gelatinous residue. Add ethyl acetate (50 mL) to the residue, followed by dilution with another 94 mL of ethyl acetate. Slowly add 15% aqueous sodium carbonate (70 mL) to the mixture with swirling by hand to gradually afford dissolution giving a final pH of 7.95. Filter and separate the layers. Extract the aqueous layer with ethyl acetate (2×100 mL). Wash the combined organic extracts with brine (1×100 mL), dried (MgSO₄), filter, and concentrate in vacuo to provide the title compound as a faint yellow oil that solidifies to an off-white solid (11.71 g, 95% yield).

m.p. 80-83° C.

$[\alpha]^{25}_D$ -57.7 (c 1.04, CH₃OH).

500 MHz ¹H NMR (CDCl₃) δ 4.31 (q, 2H, J=7.0 Hz), 4.20 (m, 2H), 3.78 (d, 1H, J=15.0 Hz), 3.36 (dd, 1H, J=4.0, 7.0 Hz), 2.93 (dd, 1H, J=4.0, 7.0 Hz), 2.81 (d, 1H, J=15.0 Hz), 2.46 (t, 1H, J=4.0), 1.34 (t, 3H, J=7.0), 1.30 (t, 3H, J=7.0).

¹³C NMR (125 MHz, CD₃Cl₃) δ 171.68, 168.57, 63.26, 62.42, 59.96, 56.06, 43.78, 32.25, 22.49, 14.31, 14.25.

FTIR (ATR) 3364.15 (s), 1725.95 (s), 1304.91 (s), 1259.24 (s), 1200.84 (s), 1104.91 (s), 1022.99 (s), 896.45 (s), 851.21 (s) cm⁻¹.

Anal. Cald for C₁₁H₁₇NO₆S: C, 45.35; H, 5.88; N, 4.81. Found: C, 45.02; H, 5.75; N, 4.82.

Preparation 54

(1R,4S,5S,6S)-4-(2'S-4'-methylthio-2'-(tert-butoxycarbonyl)aminobutanonyl)amino-2,2-dioxo-2λ⁶-thia-bicyclo[3.1.0]hexane-4,6-dicarboxylic acid diethyl ester

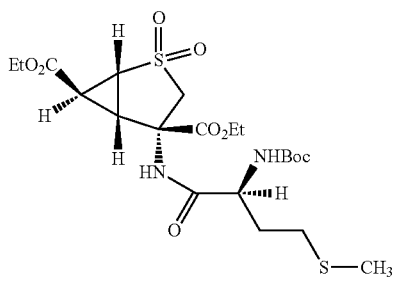

Add N-methyl morpholine (14.4 mL, 130.9 mmol) to a clear solution of N-Boc-L-methionine (32.64 g, 130.9 mmol) in 110 mL of methylene chloride at −22° C. under nitrogen, followed by addition of iso-butyl chloroformate (17 mL, 130.9 mmol) dropwise over 7 minutes to maintain the reaction temperature at −22° C. Upon completion of the addition, a resultant thin slurry was forms. Stir at −22 to −26° C. for 30 minutes. Add a solution of (1R,4S,5S,6S)-4-amino-2,2-dioxo-2λ⁶-thia-bicyclo[3.1.0]hexane-4,6-dicarboxylic acid diethyl ester (35.65 g, 122.4 mmol, Preparation 53) in 107 mL of methylene chloride during 15 minutes, followed by a rinse of 36 mL of methylene chloride. Remove the reaction from the cooling bath and stir at room temperature for 70 minutes Add 51 mL of 5 N hydrochloric acid to the solution, then separate the layers. Back extract the aqueous layer with methylene chloride (2×107 mL). Wash the combined organic layers with saturated aqueous sodium bicarbonate (1×107 mL), dried (MgSO₄), filter, and concentrate in vacuo to furnish 65.82 g (103% weight yield) of the title compound as a white foam.

$[\alpha]^{25}_D$ −12.7 (c 1.2, CH₃OH).

500 MHz ¹H NMR (CDCl₃) δ 7.53 (s, 1H), 5.06 (d, 1H, J=8.0 Hz), 4.34-4.20 (m, 6H), 3.41 (dd, 1H, J=4.0, 7.0), 2.97-2.89 (m, 2H), 2.64-2.59 (m, 2H, J=4.0), 2.12-1.89 (m, 5H), 1.47 (s, 9H), 1.32 (t, 6H, J=7.0).

¹³C NMR (125 MHz, CD₃OD) δ 172.53, 169.03, 167.88, 156.00, 80.62, 63.45, 62.56, 60.20, 55.33, 52.78, 42.81, 31.52, 31.38, 30.12, 28.49, 22.69, 15.44, 14.23, 14.143.

FTIR (ATR) 3341.88 (w), 2979.38 (s), 1733.03 (s), 1674.92 (s), 1514.58 (s), 1315.80 (s), 1255.15 (s), 1161.47 (s), 1142.63 (s), 1025.68 (s), 854.85 (s), 763.53 (s) cm⁻¹.

Preparation 55

(1R,4S,5S,6S)-4-(2'S-4'-methylthio-2'-(tert-butoxycarbonyl)aminobutanonyl)amino-2,2-dioxo-2λ⁶-thia-bicyclo[3.1.0]hexane-4,6-dicarboxylic acid monosodium salt Add 141 mL (282 mmol) of 2N sodium hydroxide to a solution of (1R,4S,5S,6S)-4-(2'S-4'-methylthio-2'-(tert-butoxycarbonyl)aminobutanonyl)amino-2,2-dioxo-2λ⁶-thia-bicyclo[3.1.0]hexane-4,6-dicarboxylic acid diethyl ester (58.95 g, 112.8 mmol theoretical, Preparation 54) in 141 mL of tetrahydrofuran at room temperature. Stir the mixture vigorously at room temperature for two minutes. Dilute the solution with 141 mL of tert-butyl methyl ether, then separate the layers. Further dilute the aqueous layer with 141 mL of water and add concentrated hydrochloric acid dropwise to lower the pH to 4.46. Stir for 10 minutes to obtain a thin slurry. Add more concentrated hydrochloric acid to the slurry to drop the pH to 1.4 (total use of 17 mL of conc. HCl, 204 mmol). After stirring for 2 hours, filter the slurry. Wash the cake with water (2×118 mL) and dry in vacuo at 45° C. for 1 hour before transferring to a weighing pan. Dry the cake again in vacuo at 45° C. for 16 hours and at 58° C. for 5 hours to provide 52.96 g (96% weight yield) of the title compound as a white solid.

mp (decomposed) 258° C.

$[\alpha]^{25}_D$ −25.2 (c 1.03, 120).

500 MHz ¹H NMR (D₂O) δ 4.07-4.01 (m, 2H), 3.45-3.43 (m, 1H), 3.11 (d, 1H, J=15.0 Hz), 2.85 (m, 1H), 2.71 (s, 3H), 2.47-2.35 (m, 3H), 1.96-1.90 (m, 4H), 1.78-1.72 (m, 1H), 1.28 (s, 9H).

¹³C NMR (125 MHz, CD₃OD) δ 174.45, 173.58, 172.80, 157.46, 81.71, 61.41, 55.04, 53.24, 42.29, 31.71, 30.85, 29.41, 27.79, 23.65, 14.41.

FTIR (ATR) 3287.62 (s), 1698.00 (s), 1528.91 (s), 1327.36 (s), 1283.74 (s), 1245.90 (s), 1174.81 (s), 1109.06 (s), 1053.05 (s), 874.27 (s), 808.95 (s) cm$^{-1}$.

Preparation 56

(1R,4S,5S,6S)-4-(2'S-4'-methylthio-2'-(tert-butoxycarbonyl)aminobutanonyl)amino-2,2-dioxo-2λ$^6$-thiabicyclo[3.1.0]hexane-4,6-dicarboxylic acid

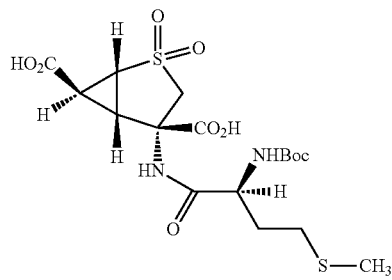

Add 397 mL (795 mmol) of 2N sodium hydroxide to a solution of (1R,4S,5S,6S)-4-(2'S-4'-methylthio-2'-(tert-butoxycarbonyl)aminobutanonyl)amino-2,2-dioxo-2λ$^6$-thiabicyclo[3.1.0]hexane-4,6-dicarboxylic acid diethyl ester (166.15 g, 318 mmol, Preparation 54) in 480 mL of tetrahydrofuran at room temperature. Stir the mixture vigorously at room temperature for two minutes, at which time the reaction becomes homogeneous to form a clear faint yellow/green solution. Stir for an additional two hours at room temperature. Dilute the solution with 480 mL of tert-butyl methyl ether, then separate the layers. Add the aqueous layer dropwise to a solution of concentrated hydrochloric acid (71.5 mL, 858 mmol) in water (960 mL). Add ethyl acetate (500 mL) followed by the rest of the aqueous layer to result an emulsion, and further dilute with ethyl acetate (460 mL). Stir the emulsion for 40 minutes, filter, and wash with water (2×250 mL). Separate the layers of the filtrate and back extract the aqueous layer with ethyl acetate (500 mL). Wash the combined organic layers with brine (75 mL), dry (MgSO$_4$), filter, and concentrate in vacuo to provide 125.26 g (84% corrected yield) of the title compound as a white foam.

Preparation 57

Ethyl 2-Bromo-2-fluoro-2-(3-oxocyclopentyl)acetate

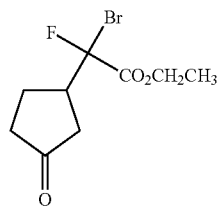

Add 8.45 mL (50.4 mmol) of triethylsilyl chloride to a suspension of 2.99 g of activated Zn (45.8 mmol) in anhydrous acetonitrile (100 mL) at −20° C. and stir the mixture for 5 minutes. Add 8.0 mL (57.3 mmol) of ethyl 2,2-dibromo-2-fluoracetate and stir the mixture for 90 minutes at −20° C. Add 1.86 mL (22.9 mmol) of 2-cyclopenten-1-one, and stir the reaction mixture overnight, allowing the temperature to rise slowly to room temperature. Add HCl 1N (125 mL) and EtOAc (100 mL). Wash the organic layer with saturated NaHCO$_3$ (2×150 mL), water (2×150 mL) and brine (2×150 mL), dry over anhydrous MgSO$_4$, filter and concentrate under reduced pressure. Purify the residue by column chromatography using EtOAc/hexane (1:8) as eluent to give the title compound (5.36 g, 88% overall yield) as a colorless oil as a mixture of diastereoisomers.

$^1$H-NMR (300 MHz, CDCl$_3$): 1.34-1.41 (m, 6H), 1.91-1.95 (m, 1H), 2.04-2.68 (m, 11H), 3.12-3.31 (m, 2H), 4.33-4.43 (m, 4H).

Zn activation: Add 10 mL of concentrated HCl to a suspension of 100 g of Zn dust in water (900 mL). Stir the mixture for 20 minutes at room temperature. Decant the water, and wash the residue with water (3×250 mL), acetone (3×150 mL), and ether (2×100 mL). Dry the residue under reduced pressure at 35° C. overnight.

Preparation 58

Ethyl (1RS,5RS,6RS)-6-fluoro-2-oxobicyclo[3.1.0]hexane-6-carboxylate

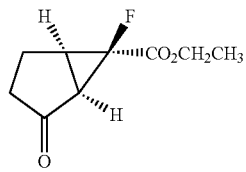

Add 13.0 mL (75.0 mmol) of ethyldiisopropylamine to a solution of 2.0 g (7.5 mmol) of ethyl 2-bromo-2-fluoro-2-(3-oxocyclopentyl)acetate (Preparation 57) in DMF (8 mL), at 0° C., and stir the mixture overnight at room temperature. Add a solution of HCl 1N (20 mL), water (15 mL), and EtOAc (75 mL). Extract the organic layer, wash with saturated NaHCO$_3$ (2×100 mL), water (2×100 mL), and brine (2×100 mL), dry over anhydrous MgSO$_4$, filter and concentrate under reduced pressure. Purify the residue by column chromatography using EtOAc/hexane (1:4) as eluent to give the title compound (1.17 g, 84% yield) as a mixture trans:cis 5:1 of isomers as a colorless oil.

$^1$H-NMR (300 MHz, CDCl$_3$): 1.33 (t, 3H, J=7.1 Hz), 2.19-2.34 (m, 3H), 2.41-2.49 (m, 1H), 2.59 (d, 1H, J=6.6 Hz), 2.71-2.76 (m, 1H), 4.29 (q, 2H, J=7.1 Hz).

Preparation 59

(1RS,2SR,5RS,6RS)-2-Spiro-5'-hydantoin-6-fluorobicyclo[3.1.0]hexane-6-carboxylic acid

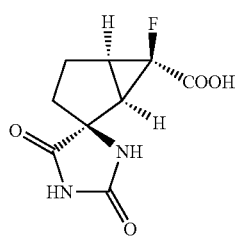

Stir a mixture of ethyl (1RS,5RS,6RS)-6-fluoro-2-oxobicyclo[3.1.0]hexane-6-carboxylate (0.1 g, 0.54 mmol, Preparation 58) and 1N NaOH (0.55 mL, 0.55 mmol) in EtOH (1 mL) for 10 min with ice cooling. Add 1 N HCl to the mixture dropwise until pH 1, and partition the resulting mixture between EtOAc and brine. Extract the aqueous phase with EtOAc twice, and dry the combined organic layers over MgSO$_4$ and then concentrated under reduced pressure. Stir a mixture of the residue, (NH$_4$)$_2$CO$_3$ (0.31 g, 3.2 mmol), and KCN (0.11 g, 1.62 mmol) in EtOH and water (1:1) (2 mL) at 60° C. overnight. Cool in an ice bath and acidify the mixture by treatment with 1 N KHSO$_4$. Remove the solvent under reduced pressure and redissolve the residue in MeOH, filter and concentrate in vacuo. The crude may be used without further purification.

Preparation 60

(1R,2S,5R,6R)-Diethyl-2-(2'R-tert-butoxycarbonylamino-propionylamino)-6-fluoro-bicyclo[3.1.0]hexane-2,6-dicarboxylate and (1S,2R,5S,6S)-Diethyl-2-(2'R-tert-butoxycarbonylamino-propionylamino)-6-fluoro-bicyclo[3.1.0]hexane-2,6-dicarboxylate

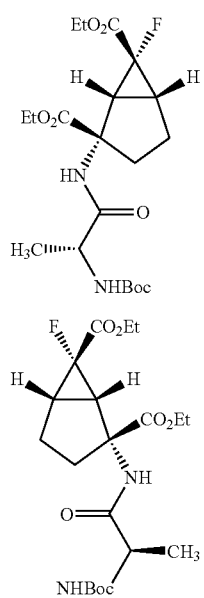

Isomer A

Isomer B

Add 1.59 g (5.0 mmol) of Ba(OH)$_2$ to a solution of 0.32 g (1.5 mmol) of (1R*,2S*,5R*,6R*)-2-spiro-5'-hydantoin-6-fluoro-bicyclo[3.1.0]hexane-6-carboxylic acid (Preparation 59) in water (10 mL), and stir the mixture at 105° C. overnight. Acidify the solution to pH 1 with 1N HCl at 0° C., then concentrate under reduced pressure. Redissolve the residue and concentrate under reduced pressure with absolute EtOH several times until the solid is perfectly dried. Add 0.37 mL (5.0 mmol) of SOCl$_2$ to the residue dissolved in absolute EtOH (20 mL) at 0° C., then stir the mixture at reflux for 5 hours. Basify the solution with saturated NaHCO$_3$ and add EtOAc (25 mL). Separate the organic layer, and extract the aqueous layer with more EtOAc (2×25 mL). Dry the combined organic layers over anhydrous MgSO$_4$, filter and concentrate at reduced pressure. Dissolve the residue in 20 mL of a mixture of DCM-DMF (4:1), 0.73 g (1.9 mmol) of HATU, 0.26 g (1.9 mmol) of HoAt, 0.35 g (1.8 mmol) of L-Ala. Add 2.7 mL (15.3 mmol) of diisopropylethylamine and stir the mixture under Ar overnight. Add DCM (15 mL), separate and wash with saturated NaHCO$_3$ (2×25 mL), water (2×25 mL), and brine (2×25 mL). Wash the organic layer over anhydrous MgSO$_4$, filter, and concentrate at reduced pressure. Purify the residue by column chromatography using EtOAc/hexane (1:2) as eluent to give the title compound (0.33 g, 51% overall yield) as a mixture of 1:1 of diastereomers as colorless oil.

The mixture of diastereomers were separated by chiral HPLC using the following analytical method: Chiralpak AD 10 m, 4.6×250 mm; Eluent: 10% IPA in Hexane; Flow: 1.0 mL/min; UV: 215 nm. Isomer A retention time=5.9 min. Isomer B retention time=9.2 min.

Isomer A: (1R,2S,5R,6R,2'R)-Diethyl-2-(2'-tert-butoxycarbonylamino-propionylamino)-6-fluoro-bicyclo[3.1.0]hexane-2,6-dicarboxylate $^1$H-NMR (300 MHz, CDCl$_3$): 1.18 (t, 3H, J=7.1 Hz), 1.23 (t, 1H, J=7.1 Hz), 1.36 (s, 9H), 1.56-1.68 (m, 1H), 2.03-2.11 (m, 2H), 2.21-2.31 (m, 1H), 2.37-2.45 (m, 1H), 2.61-2.63 (m, 1H), 4.09-4.16 (m, 5H), 5.10 (bd, 1H, J=6.6 Hz), 7.11 (bs, 1H).
$^{13}$C-NMR (75 MHz, CDCl$_3$): 13.9, 14.0, 17.7, 24.9 (d, J=1.0 Hz), 28.1, 31.5 (d, J=10.9 Hz), 34.9 (d, J=9.4 Hz), 36.4 (d, J=8.8 Hz), 49.1, 61.5, 61.8, 67.4, 77.2, 81.5 (d, J=242.6 Hz), 155.4, 168.6 (d, J=25.1 Hz), 171.8 and 172.7 ppm.

Isomer B: (1S,2R,5S,6S,2'R)-Diethyl-2-(2'-tert-butoxycarbonylamino-propionylamino)-6-fluoro-bicyclo[3.1.0]hexane-2,6-dicarboxylate $^1$H-NMR (300 MHz, CDCl$_3$): 1.13 (t, 3H, J=7.1 Hz), 1.18 (t, 1H, J=7.1 Hz), 1.31 (s, 9H), 1.51-1.60 (m, 1H), 1.98-2.07 (m, 2H), 2.15-2.22 (m, 1H), 2.26-2.39 (m, 1H), 2.55-2.60 (m, 1H), 4.07-4.12 (m, 5H), 5.20 (sd, 1H), 7.22 (bs, 1H).
$^{13}$C-NMR (75 MHz, CDCl$_3$): 13.7, 13.8, 18.0, 24.7, 28.0, 31.4 (d, J=10.9 Hz), 34.5 (d, J=8.9 Hz), 36.3 (d, J=9.4 Hz), 49.1, 61.4, 61.7, 67.3, 77.2, 81.4 (d, J=242.6 Hz), 155.2, 168.5 (d, J=25.1 Hz), 171.7 and 172.8 ppm.

Preparation 61

(1R,2S,5R,6R)-2-Amino-6-fluoro-bicyclo[3.1.0]hexane-2,6-dicarboxylic acid

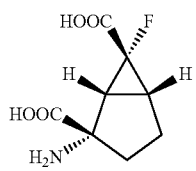

Reflux a solution of 30 mg (0.07 mmol) of Isomer A of Preparation 60 in 6N HCl (2 mL) overnight. Remove the solvent under reduced pressure, wash the residue with ether, dissolve in MeOH (1 mL), and add propilene oxide (2 mL). Stir the mixture at room temperature overnight. Decant the solvent, wash the residue with ether, and dry with an Ar stream to give the title compound (12 mg, 85%) as a white solid.

[α]$_D$=−25.0 (c=0.80 mg/mL, H$_2$O).

Preparation 62

(1S,2R,5S,6S)-2-Amino-6-fluoro-bicyclo[3.1.0]hexane-2,6-dicarboxylic acid

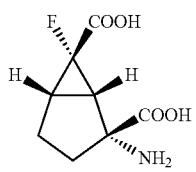

Beginning with a solution Isomer B of Preparation 60, the title compound is prepared essentially as Preparation 61. [α]$_D$=21.7 (c=0.46 mg/mL, H$_2$O).

Preparation 63

Ethyl (6S)-4-thiabicyclo[3.1.0]hex-2-ene-6-carboxylate

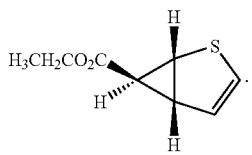

A 3-neck, 5 liter flask is fitted with a stirrer, a thermocouple, and a teflon addition tube, and a N$_2$ inlet is charged 2000 ml of thiophene (d=1.05 g/mL, 25.0 mol at beginning and increasing to 45 mol with addition of ethyl diazoacetate solution in thiophene, 17.1 equiv based upon total addition of ethyl diazoacetate and not corrected for potency of EDA, 19.0 equiv based upon potency corrected ethyl diazoacetate). To this is added, under N$_2$, 0.968 g of Rh$_2$(octanoate)$_4$ (1.24 mmoles, 0.0472 mol % based upon g of ethyl diazoacetate not corrected for potency, 0.052 mole % based upon moles of pure ethyl diazoacetate, Johnson Mathey: Lot No. 059255001). The suspension is heated to 46° C. and stirred at 46° C. for 10 minutes to affect dissolution to a green solution. To the solution is added, by a positive displacement pump, a solution of 300 g of ethyl diazoacetate (90% pure, 2.63 moles, 2.37 moles pura, 1.00 equiv, Aldrich: Lot No. 17603PI) dissolved in 1600 mL of thiophene. The rate of addition is such that the total addition time is 8 hours; the slow rate of addition suppresses formation of the maleate and fumarate ethyl esters. When no ethyl diazoacetate remains (approximately thirty minutes), the dark amber reaction (3,985 g) is cooled to 23° C. The reaction mixture is split into portions and the larger portion (3,240 g of 3,985 g total=81.3%) is directly concentrated to an oil. The crude product is passed through the wiped film distillation apparatus at 1.5 torr and 23° C. to degas the product and to remove residual amount of thiophene. The product is then distilled at 120° C. and 1.3 torr. The title compound (faint yellow) is collected in two fractions, 155.0 g and 32.2 g. Analysis by HPLC determines a potency of 78% and 76% for the two lots respectively. Crystallization of the distillate from above is accomplished by dissolution in methanol (2 mL per 1 g of distillate) and cooling to −10° C., at which time the solution is optionally seeded if crystal growth is not observed. Once crystal growth has commenced, the mixture is further cooled to −45° C. and stirred for 2-3 hours, filtered, and washed with cold (−45° C.) methanol (1×1 mL per 1 g of distillate). The material is dried in vacuo at 24° C. to provide the title compound as a white to off-white solid in 80-85% recovery and >98% potency.

Preparation 64

Ethyl (4S,6S)-4-hydroxy-2-thiabicyclo[3.1.0]hexane-6-carboxylate

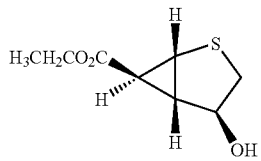

To a solution of ethyl (6S)-4-thiabicyclo[3.1.0]hex-2-ene-6-carboxylate (22.2 g, 131 mmol) in 136 mL of tetrahydrofuran under nitrogen at 0° C. is added borane-THF complex (98 mL, 98 mmol) over 15-20 minutes. After stirring at 0° C. for 30 minutes, the reaction is allowed to warm to 15° C. and stir until complete by HPLC (1.5-2 hours). The reaction is cooled to 0° C. and transferred over 10-15 minutes to 111 mL of a pre-cooled (0° C.) 1 N pH 7 buffer solution while maintaining the temperature at 0° C. To the mixture is added sodium perborate monohydrate (15.6 g, 157 mmol) as a solid in five portions such that the temperature is maintained below 20° C. The solution is allowed to warm to room temperature and stir for 1 hour followed by the addition of 222 mL of water. After stirring for 2 hours, the peroxides are quenched by adding sodium thiosulfate pentahydrate (9.7 g) dissolved in 24 mL of water followed by stirring for 10 minutes. The mixture is extracted with ethyl acetate (2×222 mL). The combined organic extracts are washed with saturated aqueous sodium bicarbonate (1×222 mL) followed by brine (1×222 mL) and concentration in vacuo to dryness. The crude product is dissolved in 1,2-dichloroethane (1 mL per 1 g of crude oil) and loaded onto a silica gel column (4 g of silica gel per 1 g of crude oil slurried and packed in 15% ethyl acetate-heptane). The column is eluted with 15% ethyl acetate-heptane until product is visible by TLC, at which time the solvent is switched to 50% ethyl acetate-heptane. All fractions containing the title product are combined and concentrated in vacuo to an oil. Overall yield is in the 55-65% range.

Preparation 65

Ethyl (6S)-4-oxo-2-thiabicyclo[3.1.0]hexane-6-carboxylate

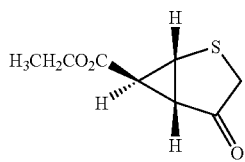

To a solution of dimethylsulfoxide (33.4 mL, 471 mmol) in 194 mL of methylene chloride at −70° C. is slowly added a solution of trifluoroacetic anhydride (33.2 mL, 235 mmol) in 73 mL of methylene chloride over 30 minutes (temperature maintained below −66° C.). After stirring for 20 min, a solution of ethyl (4S,6S)-4-hydroxy-2-thiabicyclo[3.1.0]hexane-6-carboxylate (34.1 g, 181 mmol) in 194 mL of methylene chloride is added over 60 minutes such that the temperature is maintained below 60° C. After stirring for 1 hour, the reaction is treated with triethylamine (75.7 mL, 543 mmol) over 35 minutes such that the temperature remains below −50° C. The reaction is allowed to stir an additional 1 hour, at which time the cooling bath is removed and 400 mL of 2 N hydrochloric acid is added. Upon warming to 0° C., the layers are separated and the organic layer is washed with 2N hydrochloric acid (1×300 mL), 1N aqueous sodium bicarbonate (1×670 mL), and water (1×300 mL) followed by drying over sodium sulfate, filtering, and concentrating in vacuo to a red oil which solidifies upon standing. The crude product is applied to a pad of silica gel (2 g per 1 g of starting alcohol packed with methylene chloride) and eluted with methylene chloride (200-300 mL). All fractions containing product are collected and concentrated to provide the title compound as an orange/brown solid. Typical corrected yields are in the 85-90% range.

Preparation 66

(6S,11S)-8,10-dioxo-2-thiaspiro[bicyclo[3.1.0]hexane-4,5'-imidazolidine]-6-carboxylic acid

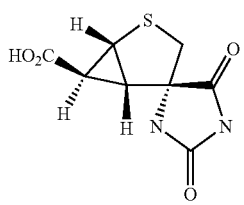

Ammonium carbonate (2.46 g, 25.6 mmol) and potassium cyanide (0.817 mg, 12.5 mmol) are combined in 19.9 mL of methanol and allowed to stir for 30 minutes. The mixture is treated with a solution of ethyl (6S)-4-oxo-2-thiabicyclo[3.1.0]hexane-6-carboxylate (2.39 g, 12.8 mmol) in 19.9 mL of methanol and the reaction is heated to 30° C. and stirred for 23 hours. The volatiles are evaporated and the residue is dissolved in 2.75N sodium hydroxide (13.1 mL) and stirred for 1 hour. After dilution with 13.1 mL of water, the pH is lowered to 3.1 with concentrated hydrochloric acid and optionally seeded with (6S,11R)-8,10-dioxo-2-thiaspiro[bicyclo[3.1.0]hexane-4,5'-imidazolidine]-6-carboxylic acid. The pH is lowered to 1.0 and the suspension is cooled to 0° C. and stirred for 1.25 hours. The tan solid is collected, washed with cold water (2.3 mL and 0.8 mL), and dried overnight in vacuo at 40° C. giving 2.00 g (55% corrected for purity) of (6S,11R)-8,10-dioxo-2-thiaspiro[bicyclo[3.1.0]hexane-4,5'-imidazolidine]-6-carboxylic acid. The filtrate is diluted with 50 mL of ethyl acetate and treated with 18 g of sodium chloride. After stirring for 15 minutes, the layers are separated and the aqueous layer is further washed with ethyl acetate (2×50 mL). The combined organic extracts are dried with sodium sulfate, filtered, and concentrated in vacuo to a slurry (ca. 5 mL) to which is added tert-butyl methyl ether (25 mL) followed by stirring overnight. The solid is collected, washed with tert-butyl methyl ether, and dried in vacuo at 40° C. for 2 hours to provide 0.64 g (10% corrected for purity) of the title compound as a 1:1 mixture of diastereomeric hydantoins. This second crop of hydantoins is combined with the first crop and subjected to the next step.

Resolution

To a slurry of racemic acid (15 g, 65.7 mmol, ca. 6:1 ratio of diastereomeric hydantoins) in 300 mL of ethanol and 75 mL of water is added (R)-phenylglycinol (9.0 g, 65.7 mmol). The mixture is heated to ca. 80° C. to effect dissolution. The dark solution is allowed to cool slowly and precipitation was observed at 40-45° C. The slurry is further cooled 0° C. and held for 1-1.5 hours. The solid is collected, washed (with stirring) with 4:1 ethanol:water (1×60 mL, pre-chilled to 0° C.), and dried in vacuo at 65° C. for 12-24 hours. Typical yields of the resolved salt are in the 37-45% range with >98% de and >98% ee observed. The resolved salt is dissolved in 6 volumes (mL per g) of water followed by treatment with 1.1 equivs. of conc HCl. The slurry is cooled to 0° C. and allowed to stir for 1 hour followed by filtration, rinsing with 1 volume of cold water, and drying in vacuo at 60° C. Typical yields of the title compound are >90% with % de and % ee >99%.

Preparation 67

(6S,11S)-2,2,8,10-Tetraoxo-2-thiaspiro[bicyclo[3.1.0]hexane-4,5'-imidazolidine]-6-carboxylic acid

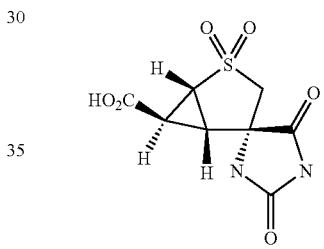

To a mixture of 6.8 mL of water, 0.7 mL of 50% aqueous sodium hydroxide, and 186 mg (0.74 mmol) of tungstic acid is added (6S,11S)-8,10-dioxo-2-thiaspiro[bicyclo[3.1.0]hexane-4,5'-imidazolidine]-6-carboxylic acid (3.4 g, 14.9 mmol). The resulting solution is heated to 50° C. and treated with 35% hydrogen peroxide (7.7 mL, 74.5 mmol) slowly over 66 minutes. The reaction is allowed to stir thereafter at 47-48° C. for 5 hours, followed by cooling to 0° C., filtering over a thin pad of Celite, and rinsing with cold water (1×2 mL). The filtrate is heated to 50° C. and treated with concentrated hydrochloric acid to pH=1.5. The slurry is allowed to cool to room temperature and stir over night. Upon cooling to 0° C., the slurry is filtered, washed with cold water (2×2 mL), and vacuum dried at 55° C. to a constant weight, providing 3.19 g (82%) of the title compound as a white solid:

$[\alpha]^{25}_D$ −48.6 (c, 1.19, 1 N NaOH).

mp 275° C. (gray), 295° C. (brown).

500 MHz $^1$H NMR (DMSO-$d_6$) δ 13.15 (br s, 1H), 10.99 (s, 1H), 8.13 (s, 1H), 3.85 (d, 1H, J=15.0 Hz), 3.74 (dd, 1H, J=7.0, 4.0 Hz), 3.03 (d, 1H, J=15.5 Hz), 2.80 (dd, 1H, 7.0, 4.0 Hz), 2.39 (t, 1H, J=4.0 Hz).

$^{13}$C NMR (125 MHz, DMSO-$d_6$) δ 174.39, 169.87, 156.35, 62.67, 52.59, 44.16, 31.69, 21.92; FTIR (KBr) 3317 (s), 3250 (s), 3211 (s), 3086 (w), 1791 (s), 1742 (s), 1713 (s), 1327 (s), 1192 (s), 1140 (s) cm$^{-1}$.

Preparation 68

(1R,4S,5S,6S)-4-Amino-(2-sulfonylbicyclo[3.1.0] hexane)-4,6-dicarboxylic acid

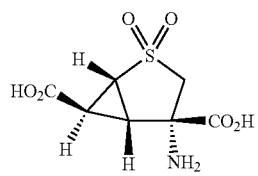

To a stainless steel Parr reactor is added (6S,11S)-2,2,8,10-Tetraoxo-2-thiaspiro[bicyclo[3.1.0]hexane-4,5'-imidazolidine]-6-carboxylic acid (2.50 g, 9.60 mmol) and 2N sodium hydroxide (24.0 mL, 48.0 mmol). After the mixture is heated to 95° C. and stirred for 21 hours, the mixture is cooled to room temperature and treated with activated charcoal (1.25 g). The mixture is filtered through Celite and the filtrate is concentrated to 17 g and diluted with $H_2O$ to afford a weight of 24 g. The pH is lowered to 6.5 using conc. HCl and the mixture heated to 62° C. After the pH is lowered to 2.5 using conc. HCl, crystallization occurred. The suspension is allowed to cool to 30° C. before the pH is adjusted to 1.7 and its temperature lowered to 5° C. After the suspension is held at this temperature for 18 hours, the solid is collected and washed with cold $H_2O$ (2×2.9 mL). The white solid is dried in vacuo at 45° C. to afford the title compound (1.81 g, 80%). The title compound is slurried in 10 volumes of water and heated to 85° C. for 3-4 hours, cooled to room temperature, stirred for 2-3 hours, filtered, and washed with water (1×1 volume). Recovery is >95%.

Preparation 69

Ethyl (6S)-2-oxobicyclo[3.1.0]hexane-6-carboxylate

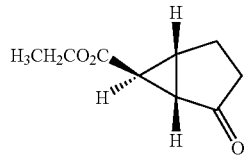

To a suspension of (ethoxycarbonylmethyl)dimethyl sulfonium bromide (134 g, 585 mmol) in 486 mL of acetonitrile at room temperature is added 87.4 mL (585 mmol) of 1,8-diazabicyclo[5.4.0]undec-7-ene dropwise over 15 minutes. After stirring for 1 hour, the yellow mixture is treated with 40 g (487 mmol) of 2-cyclopenten-1-one over 10 minutes. The mixture is allowed to stir over night at which time 480 mL of tert-butyl methyl ether is added, followed by washing with 1N hydrochloric acid (1×240 mL). The aqueous layer was washed with tert-butyl methyl ether (1×240 mL). The combined organic extracts were washed with brine (1×400 mL), dried ($MgSO_4$), filtered, and concentrated in vacuo to provide crude ethyl (6S)-2-oxobicyclo[3.1.0]hexane-6-carboxylate as an orange solid (84.8 g). The crude material may be purified through distillation (~138° C., 10 mm Hg), followed by slurrying the solidified distillate in heptane, filtering, and drying.

Preparation 70

(±)(6S)-2-Oxobicyclo[3.1.0]hexane-6-carboxylic acid

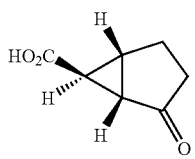

To a solution of crude ethyl (6S)-2-oxobicyclo[3.1.0]hexane-6-carboxylate (30.2 g, 180 mmol, uncorrected) in 30 mL of ethanol at room temperature is added 89 mL (178 mmol) of 2N sodium hydroxide. Upon stirring for 80 minutes, the reaction mixture is washed with tert-butyl methyl ether (1×90 mL) and the aqueous layer is treated with conc. hydrochloric acid (18 mL) to reach a pH=1.0. The mixture is treated with 15 g of sodium chloride followed by washing with ethyl acetate (3×90 mL). The combined organic extracts are dried ($Na_2SO_4$), filtered, and concentrated in vacuo to give 23.8 g (94%, uncorrected) of the title compound as an off-white solid.

Preparation 71

(+)(6S)-2-Oxobicyclo[3.1.0]hexane-6-carboxylic acid N-benzyl-α-methylbenzylamine salt

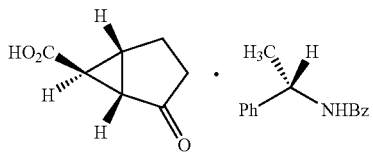

To a solution of crude (±)(6S)-2-oxobicyclo[3.1.0]hexane-6-carboxylic acid (11.9 g, 84.9 mmol, assume 100% potency) in 119 mL of 6:1 ethyl acetate:ethanol at reflux is added 18 g (85.1 mmol) of (S)-N-benzyl-α-methylbenzyl-amine. Upon dissolution, the mixture is allowed to cool optionally followed by seeding at 52° C. Upon cooling to room temperature and stirring an additional 13.5 h, the crystals are collected and washed with 6:1 ethyl acetate:ethanol (2×48 mL). Drying in vacuo gave 10.8 g (36%, 77% de) of the resolved salt as a solid.

The de of the salt is determined by chiral GC analysis of the derived methyl ester prepared as follows: 150 mg of the resolved salt is dissolved in 5 mL of methylene chloride and is washed with 1N sulfuric acid (2×1 mL). The organic layer is dried, filtered, diluted with 2 mL of methanol, and treated with 1 mL of 2 M trimethylsilyl diazomethane in hexanes. After stirring at room temperature for 15 minutes, the mixture is concentrated in vacuo to provide the methyl ester suitable for chiral GC analysis. GC conditions: 30 m×0.25 mm×0.25μ β-DEX 325 column, 140° C. oven temperature, helium car-

Preparation 72

Ethyl (6S)-2-oxobicyclo[3.1.0]hexane-6-carboxylate

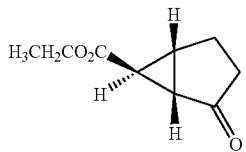

To a suspension of 46.3 g (132 mmol) of (6S)-2-oxobicyclo[3.1.0]hexane-6-carboxylic acid N-benzyl-α-methylbenzylamine salt in 200 mL of ethyl acetate is added 198 mL (198 mmol) of 2N sodium hydroxide. After mixing well, the layers are separated and the aqueous layer is washed with ethyl acetate (1×200 mL). The aqueous layer is treated with 18 mL (211 mmol) of conc. hydrochloric acid and 100 g of sodium chloride. The mixture is allowed to stir for 30 minutes followed by washing with ethyl acetate (2×200 mL). The combined organics are dried (MgSO$_4$), filtered, and concentrated in vacuo to provide 18.3 g (99%) of the resolved acid [(+)(6S)-2-oxobicyclo[3.1.0]hexane-6-carboxylic acid] as a white solid.

Next, 10 g (71 mmol) of crude resolved acid product from above is dissolved in 42 mL of ethanol and treated with 4 mL (71 mmol) of conc. sulfuric acid dropwise. The mixture is heated to 45° C. and is allowed to stir for 75 minutes. Upon cooling to room temperature, 42 mL of water is added along with 20 mL of ethyl acetate and 12 g of sodium bicarbonate. Upon stirring for several minutes, the mixture is washed with ethyl acetate (2×50 mL). The combined organics are dried (MgSO$_4$), filtered, and concentrated in vacuo to provide 11 g (92%) of crude ethyl (6S)-2-oxobicyclo[3.1.0]hexane-6-carboxylate as a white solid. Crystallization from 6:1/heptane:tert-butyl methyl ether (3.5 mL per g of substrate) provided this title compound in approximately 80% yield and >98% ee as determined by chiral GC analysis.

Preparation 73

(6S)-6-(Ethoxycarbonyl)bicyclo[3.1.0]hex-2-en-2-yl acetate

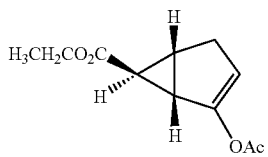

A mixture of ethyl (6S)-2-oxobicyclo[3.1.0]hexane-6-carboxylate (380.1 g, 2.26 mol) and sulfuric acid (18 M, 6.3 mL, 0.11 mol) in isopropenyl acetate (2.26 L) is heated at reflux using a Dean-Stark apparatus for 2.5 hours, at which time GC analysis revealed a 9:1 mixture of the title compound versus ethyl (6S)-2-oxobicyclo[3.1.0]hexane-6-carboxylate. After the removal of 950 mL of solvent by distillation over 1 hour, GC shows that the product/starting material ratio is 17:1. Additional isopropenyl acetate (900 mL) and conc. H$_2$SO$_4$ (3.15 mL) are added, and the mixture is stirred at reflux for another 15 hours, at which time GC shows 27:1 product/starting material. After another 1.35 L of solvent is distilled off, the mixture is cooled to room temperature before it is diluted with MTBE (2 L), H$_2$O (250 mL), and aqueous saturated NaHCO$_3$ (600 mL). The layers are separated and the organic layer is washed with brine (400 mL). The combined aqueous layers are extracted with MTBE (400 mL), and the combined organic layers are dried (Na$_2$SO$_4$), filtered, and concentrated to a dark red/brown oil (540 g). The crude oil is split into two equal portions and filtered through a pad of flash SiO$_2$ (713 g for each batch), eluting with 10:1/heptane:ethyl acetate. The product-containing fractions from both plugs are combined and concentrated to afford the title compound as a yellow oil (460 g, 97%; 90% corrected for solvent by NMR). Column chromatography on silica gel eluting with ethyl acetate/hexanes (1:5) provides an analytically pure sample of the title compound as a colorless oil.

[α]$^{25}_D$ +185 (c 1.48, CHCl$_3$).

500 MHz $^1$H NMR (CDCl$_3$) δ 5.19-5.18 (m, 1H), 4.12 (q, 1H, J=7.0 Hz), 4.11 (q, 1H, J=7.0 Hz), 2.74-2.69 (m, 1H), 2.48-2.43 (m, 2H), 2.22-2.19 (m, 1H), 2.16 (s, 3H), 1.39 (dd, 1H, J=2.5, 2.5 Hz), 1.25 (t, 3H, J=7.0 Hz).

$^{13}$C NMR (125 MHz, CDCl$_3$) δ 173.37, 169.01, 152.26, 111.56, 61.28, 32.47, 32.40, 29.72, 24.97, 21.67, 14.95.

FTIR (CHCl$_3$) 3026 (m), 2985 (m), 1724 (s), 1272 (s), 1187 (s) cm$^{-1}$.

ES HRMS calcd for C$_{11}$H$_{18}$NO$_4$ [M+NH$_4$]$^+$ 228.1236, found 228.1252.

Preparation 74

Ethyl(3S,1R,6R)-7-oxa-5-oxotricyclo[4.1.0.0<2,4>]heptane-3-carboxylate

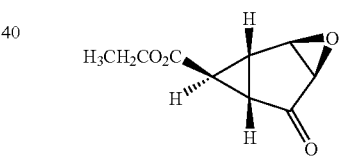

A mixture of (6S)-6-(ethoxycarbonyl)bicyclo[3.1.0]hex-2-en-2-yl acetate (212.2 g, 1.01 mol) and 2,3-dichloro-5,6-dicyano-1,4-benzoquinone (252.0 g, 1.11 mol) in 2.02 L of 1,4-dioxane is heated to reflux and stirred for 17 hours, at which time GC analysis shows complete conversion to ethyl (6S)-4-oxobicyclo[3.1.0]hex-2-ene-6-carboxylate. The mixture is cooled to room temperature and diluted with THF (564 mL). After the mixture is cooled to 8° C., 1,8-diazabicyclo[5.4.0]undec-7-ene (377 mL, 2.52 mol) is added over 30 minutes such that the reaction temperature is maintained below 10° C. The mixture is then cooled to 5° C., and tert-butyl hydroperoxide (70 wt % in water, 210 mL, 1.51 mol) is added over 50 minutes, maintaining the reaction temperature below 9° C. After the mixture stirred another 50 minutes, the reaction is filtered and the brown cake is washed with MTBE (2×800 mL). To the filtrate is added 1.20 L of 1N HCl and, after mixing well, the layers are separated. The organic layer is washed sequentially with aqueous saturated NaHCO$_3$ (1.20 L), aqueous saturated Na$_2$S$_2$O$_3$ (1.20 L), and brine (600 mL). After the solution is dried (Na$_2$SO$_4$), it is concentrated to an orange sludge which is diluted with 200 mL of heptane. The volatiles are evaporated to produce an orange solid that is triturated with 350 mL of heptane and filtered, washing the cake with additional heptane (2×175 mL). The collected solid is dried in vacuo at room temperature for 17 hours to provide 138.7 g (75%) of the title compound as a brown-yellow solid. Crystallization from MTBE provides an analytically pure sample of the title compound as a white solid.

$[\alpha]^{25}_D$ +2.3 (c 1.20, CHCl$_3$), +8.4° (c 1.28, acetone); mp 129-130° C.

500 MHz $^1$H NMR (CDCl$_3$) δ 4.16 (q, 2H, J=7.0 Hz), 3.99 (t, 1H, J=2.5 Hz), 3.24-3.23 (m, 1H), 2.96-2.94 (m, 1H), 2.21-2.19, (m, 1H), 2.08 (t, 1H, J=3.0 Hz), 1.26 (t, 3H, J=7.0 Hz).

$^{13}$C NMR (125 MHz, CDCl$_3$) δ 201.19, 168.84, 62.42, 57.04, 51.25, 31.16, 30.54, 29.60, 14.79.

FTIR (KBr) 3087 (w), 3059 (w), 3051 (w), 3007 (w), 2993 (w), 2963 (w), 1753 (s), 1719 (s), 1273 9s), 1191 (s), 1009 (m), 848 (m) cm$^{-1}$.

Anal. Cald for C$_9$H$_{10}$O$_4$: C, 59.34; H, 5.53. Found: C, 59.32; H, 5.43.

Preparation 75

Ethyl (6S)-4-oxobicyclo[3.1.0]hex-2-ene-6-carboxylate

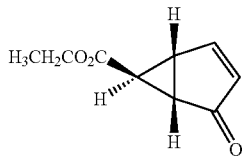

Although the title compound is typically used in situ in the preparation of ethyl (3S,1R,6R)-7-oxa-5-oxotricyclo[4.1.0.0<2.4>]heptane-3-carboxylate, an analytically pure sample of the title compound is obtained by filtering the reaction mixture containing this compound and evaporating the filtrate to give a brown solid. The solid is resuspended in ethyl acetate, the suspension filtered, and the filtrate concentrated. Chromatography of the residue on silica gel with ethyl acetate/hexanes (1:5 to 1:2) gives the title compound, which is recrystallized from hot ethyl acetate and chromatographed again using the previous conditions to give the title compound as a white solid.

$[\alpha]^{25}_D$ −268 (c 1.17, CHCl$_3$).

mp 97-98° C.

500 MHz $^1$H NMR (CDCl$_3$) δ 7.60 (ddd, 1H, J=5.5, 2.5, 0.75 Hz), 5.73 (dd, 1H, J=5.0, 0.5 Hz), 4.15 (q, 2H, J=7.0 Hz), 2.96-2.94 (m, 1H), 2.63-2.61 (m, 1H), 2.60 (t, 1H, J=2.5 Hz), 1.26 (t, 3H, J=7.0 Hz).

$^{13}$C NMR (125 MHz, CDCl$_3$) δ 203.96, 168.61, 160.33, 130.29, 62.03, 46.53, 30.72, 29.62, 14.82.

FTIR (KBr) 3080 (m), 2996 (m), 1717 (s), 1695 (s), 1266 (s), 1291 (m), 1191 (s), 179 (s) cm$^{-1}$.

Anal. Cald for C$_9$H$_{10}$O$_3$: C, 65.05; H, 6.07. Found: C, 64.97; H, 6.01.

Preparation 76

Ethyl (4S,6S)-4-hydroxy-2-oxobicyclo[3.1.0]hexane-6-carboxylate

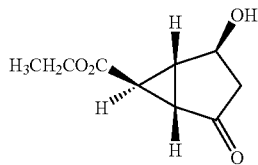

A stirred solution of ethyl (3S,1R,6R)-7-oxa-5-oxotricyclo[4.1.0.0<2,4>]heptane-3-carboxylate (36.3 g, 0.20 mol) in 667 mL of acetone is treated sequentially with sodium acetate (36.1 g, 0.44 mol), sodium iodide (65.8 g, 0.44 mol), and acetic acid (27.5 mL, 0.48 mol). The mixture is allowed to stir at 30° C. for 15 hours before the acetone is removed in vacuo leaving behind a brown solid that is partitioned between ethyl acetate (323 mL) and H$_2$O (323 mL). The layers are separated and the aqueous layer is washed with ethyl acetate (3×323 mL). The combined organics are washed sequentially with aqueous saturated Na$_2$S$_2$O$_3$ (364 mL) and aqueous saturated NaHCO$_3$ (364 mL). Each aqueous wash is back-extracted with ethyl acetate (323 mL). The combined organics are dried (Na$_2$SO$_4$), filtered, and concentrated to a red-brown oil which was dissolved in 300 mL of ethanol. Evaporation of the volatiles affords the title product as a red-brown oil (41.8 g, 114%). Column chromatography on silica gel using ethyl acetate/hexanes (1:2 to 2:1) followed by crystallization from hot MTBE provides an analytically pure sample of the title compound as a white solid.

$[\alpha]^{25}_D$ +3.9 (c 1.39, CHCl$_3$), +6.0° (c 1.69, MeOH).

mp 81-82° C.

500 MHz $^1$H NMR (CDCl$_3$) δ 4.60 (br s, 1H), 4.16 (q, 2H, J=7.0 Hz), 2.66 (dd, 1H, J=5.0, 4.0 Hz), 2.42-2.40 (m, 1H), 2.34 (dd, 1H, J=19.0, 5.5 Hz), 2.24, (br d, 1H, J=3.0 Hz), 2.07 (d, 1H, J=19.0 Hz), 1.91 (t, 1H, J=3.0 Hz), 1.27 (t, 3H, J=7.0 Hz).

$^{13}$C NMR (125 MHz, CDCl$_3$) δ 209.74, 170.07, 69.04, 62.32, 43.47, 36.89, 34.95, 26.14, 14.83.

FTIR (CHCl$_3$) 3607 (w), 3447 (w), 3025 (m), 2985 (w), 1739 (s), 1728 (s), 1270 (s), 1187 (s) cm$^{-1}$.

Anal. Cald for C$_9$H$_{12}$O$_4$: C, 58.69; H, 6.57. Found: C, 58.48; H, 6.63.

Preparation 77

Ethyl 2-[((1R)-1-phenylethyl)amino](2S,4S,6R)-2-cyano-4-hydroxybicyclo[3.1.0]hexane-6-carboxylate

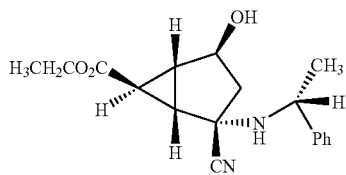

To a solution of ethyl (4S,6S)-4-hydroxy-2-oxobicyclo[3.1.0]hexane-6-carboxylate (68.2 g corrected to 60.0 g due to ethanol contamination, 0.326 mol) in ethanol (332 mL) and H₂O (332 mL) is added (R)-methylbenzylamine (46.3 mL, 0.359 mol) and NaCN (20.8 g, 0.424 mol), maintaining the temperature between 20 and 25° C. Conc. HCl (35.3 mL, 0.424 mol) is then added over 10 min while maintaining the above reaction temperature. The dark brown mixture is stirred for 1 hour before it is optionally seeded with the title compound to initiate crystallization. The suspension is stirred for 1 hour before H₂O (664 mL) is added. After the suspension stirs another 1.75 hours, the title compound is collected as a tan solid which is washed with H₂O (332 mL). Air is pulled through the wetcake on the filter for 25 minutes before the material is used directly in the nitrile hydrolysis (wetcake weight 145 g). Although the title compound quickly decomposes during in vacuo drying at temperatures greater than 25° C., it is possible to dry small samples in vacuo at room temperature without decomposition.

$[\alpha]^{25}_D$ +81.6 (c 1.18, CHCl₃).

mp 70-72° C. (decomp).

500 MHz ¹H NMR (CDCl₃) δ 7.39 (d, 2H, J=7.0 Hz), 7.26-7.16 (m, 3H), 4.31 (d, 1H, J=5.0 Hz), 4.22 (q, 1H, J=6.5 Hz), 3.93-3.85 (m, 2H), 2.33 (d, 1H, J=15.0 Hz), 2.01 (br t, 1H, J=4.5 Hz), 1.64 (dd, 1H, J=15.0, 5.0 Hz), 1.55-1.54 (m, 1H), 1.40-1.39 (m, 4H), 1.17 (t, 3H, J=7.0 Hz).

¹³C NMR (125 MHz, CDCl₃) δ 170.54, 144.85, 128.61, 127.45, 127.38, 121.88, 72.17, 61.02, 60.66, 56.57, 45.82, 36.70, 34.45, 25.83, 21.75, 14.22.

FTIR (KBr) 3568 (m), 3489 (m), 3285 (m), 2923 (m), 2228 (w), 1712 (s), 1298 (m), 1197 (m) cm⁻¹.

FAB HRMS calcd for C₁₈H₂₃N₂O₃ [M+H]⁺ 315.1709, found 315.1704.

Preparation 78

2-[((1R)-1-Phenylethyl)amino](2S,4S,6R)-4-hydroxybicyclo[3.1.0]hexane-2,6-dicarboxylic acid

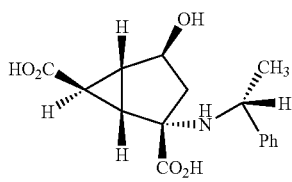

To a solution of ethyl 2-[((1R)-1-phenylethyl)amino](2S,4S,6R)-2-cyano-4-hydroxybicyclo[3.1.0]hexane-6-carboxylate wetcake (0.326 mmol theory) in DMSO (220 mL) is slowly added 30% H₂O₂ (44.5 mL, 0.426 mol), maintaining the temperature below 27° C. The temperature is lowered to 19° C. and 5N NaOH (52.3 mL, 0.262 mol) is carefully and slowly added at first over 15 minutes, maintaining the temperature between 22 and 27° C. An ice bath of appropriate capacity is required to handle the exotherm of this reaction. After the brown, heterogeneous mixture is stirred for 20 minutes at the above temperature range, HPLC showed that the starting material had been consumed to give an amide intermediate. After the reaction is stirred another 1.5 hours, Na₂SO₃ (13.7 g, 0.109 mol) is added and the mixture stirs for 15 minutes, at which time the mixture tests negatively for peroxides by starch-iodide paper. Following the addition of 3N NaOH (291 mL, 0.873 mol), the mixture is heated to 85° C. and stirred for 18 hours. The homogeneous brown mixture is cooled to 30° C. and conc. HCl is added to lower the pH to 3.6 while maintaining the temperature between 30 and 35° C. After crystallization begins at pH 3.6, the suspension is stirred for 15 minutes before the pH is lowered to 2.5. After the mixture is stirred for 10 additional minutes, it is cooled to 2° C. and stirred for 2 hours before the gray solid is collected and washed with cold H₂O (400 mL) and EtOH (300 mL). The collected solid is dried in vacuo at 45° C. for 17 hours to provide 42.9 g (43% from the start of Preparation 18) of the title compound. In order to forward process all of the title compound produced in the reaction, it is recovered from the mother liquor in the following manner. The ethanol portion of the mother liquor is evaporated and the residue is combined with the aqueous portion of the mother liquor. Following the distillation of H₂O (485 mL) under reduced pressure, the pH of the mother liquor is adjusted to 12.9 with 70 mL of 5N NaOH and 5 mL of 50% NaOH. After the solution is washed with n-BuOH (3×800 mL), its pH is adjusted to 2.5 with conc. HCl and the solution is concentrated. The residue is diluted with EtOH (100 mL) and the volatiles evaporated (2×). The residue is diluted with EtOH (150 mL) and the tan solid containing additional title compound and salts is washed with EtOH (75 mL) and dried at 50° C. in vacuo to a weight of 102 g. Both crops of the title compound were used in the subsequent esterification.

$[\alpha]^{25}_D$ +4.5 (c 1.41, 1 N NaOH).

mp 220° C. (gray from off-white), 280° C. (brown).

500 MHz ¹H NMR (D₂O, KOD) δ 7.39 (d, 2H, J=7.0 Hz), 7.19-7.04 (m, 5H), 3.92 (d, 1H, J=5.0 Hz), 3.67 (q, 1H, J=7.0 Hz), 1.76 (d, 1H, J=15.0 Hz), 1.54-152 (m, 1H), 1.37 (dd, 1H, J=15.0, 5.0 Hz), 1.15 (d, 3H, J=6.5 Hz), 1.12 (dd, 1H, J=6.0, 3.0 Hz), 0.92 (t, 1H, J=3.3 Hz).

¹³C NMR (125 MHz, D₂O, KOD) δ 185.82, 182.96, 148.01, 131.31, 129.97, 129.78, 74.99, 73.84, 58.78, 46.91, 38.05, 35.02, 27.34, 27.15.

FTIR (KBr) 3366 (m), 3072 (s), 2886 (s), 1696 (m), 1611 (m), 1560 (m), 1455 (m), 1377 (m), 1278 (m), 1202 (m), 1188 (m) cm⁻¹.

Anal. Cald for C₁₆H₁₉NO₅: C, 62.94; H, 6.27; N, 4.59. Found: C, 62.70; H, 6.21; N, 4.67.

Preparation 79

Ethyl 2-[((1R)-1-phenylethyl)amino](2S,4S,6R)-2-carbamoyl-4-hydroxybicyclo[3.1.0]hexane-6-carboxylate

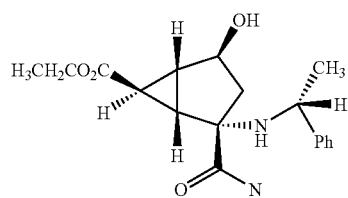

Although the title compound is typically used in situ in the preparation of 2-[((1R)-1-phenylethyl)amino](2S,4S,6R)-4-hydroxybicyclo[3.1.0]hexane-2,6-dicarboxylic acid, the compound could be isolated albeit with some yield loss due to accompanying ester hydrolysis during the nitrile hydrolysis. In the isolation, the nitrile hydrolysis reaction mixture is partitioned between CH₂Cl₂ and H₂O as soon as ethyl 2-[((1R)-1-phenylethyl)amino](2S,4S,6R)-2-cyano-4-hydroxybicyclo[3.1.0]hexane-6-carboxylate is consumed. After the organic layer is dried (MgSO₄) and concentrated, the residue is purified by silica gel column chromatography using EtOAc/hexanes (2:1) to EtOAc to afford the title compound as a white foam.

$[\alpha]^{25}_D$ +61.3 (c 1.20, CHCl$_3$).

500 MHz $^1$H NMR (CDCl$_3$) δ 7.32-7.20 (m, 5H), 7.19 (br d, 1H, J=4.0 Hz), 5.49 (br d, 1H, J=4.0 Hz), 4.88 (d, 1H, J=11.5 Hz), 4.24 (dd, 1H, J=11.5, 6.0 Hz), 4.06-4.00 (m, 2H), 3.77 (q, 1H, J=7.0 Hz), 2.21 (d, 1H, J=15.0 Hz), 2.18-2.15 (m, 2H), 1.71 (br s, 1H), 1.54 (dd, 1H, J=14.5, 6.0 Hz), 1.38, (d, 3H, J=6.5 Hz), 1.32 (t, 1H, J=3.3 Hz), 1.24 (t, 3H, J=7.0 Hz).

$^{13}$C NMR (125 MHz, CDCl$_3$) δ 180.42, 171.47, 146.05, 128.97, 127.43, 126.48, 73.16, 70.76, 61.08, 56.00, 42.82, 35.97, 35.67, 26.13, 21.53, 14.34.

FTIR (CHCl$_3$) 3441 (m), 3345 (m), 2975 (w), 1725 (s), 1665 (s), 1288, 1186 (m) cm$^{-1}$.

Anal. Calcd for C$_{18}$H$_{24}$N$_2$O$_4$: C, 65.04; H, 7.28; N, 8.43. Found: C, 65.41; H, 7.58; N, 8.32.

Preparation 80

Ethyl 2-[((1R)-1-phenylethyl)amino](2S,4S,6R)-2-(ethoxycarbonyl)-4-hydroxybicyclo[3.1.0]hexane-6-carboxylate

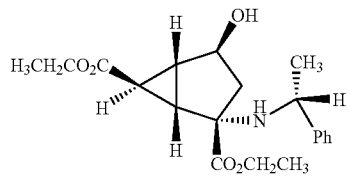

To a suspension of 2-[((1R)-1-phenylethyl)amino](2S,4S,6R)-4-hydroxybicyclo[3.1.0]hexane-2,6-dicarboxylic acid (4 g, 13 mmol) in 48 mL of ethanol at room temperature is added acetyl chloride (11.2 mL, 157 mmol) via an addition funnel such that a gentle reflux is maintained. The resulting mixture is allowed to stir another 16 hours at reflux and upon cooling to room temperature is concentrated in vacuo to a solid residue. The solid is treated slowly with a solution of sodium bicarbonate (6.6 g) in 100 mL of water followed by washing with ethyl acetate (2×100 mL). The combined organics are dried (MgSO$_4$), filtered, and concentrated in vacuo to give 4.7 g (99%) of the title compound as a solid. Column chromatography on silica gel eluting with CH$_2$Cl$_2$/MeOH (95:5) followed by crystallization from Et$_2$O provides an analytically pure sample of the title compound as a white solid.

$[\alpha]^{25}_D$ +52.5 (c 1.30, CHCl$_3$).

mp 73-74° C.

500 MHz $^1$H NMR (CDCl$_3$) δ 7.29-7.14 (m, 5H), 4.25 (dq, 1H, 11.0, 7.0 Hz), 4.18 (dd, 1H, J=9.5, 5.5 Hz), 4.10 (dq, 1H, J=11.0, 7.0 Hz), 3.92 (dq, 1H, J=11.0, 7.0 Hz) 3.82 (dq, 1H, J=11.0 Hz, 7.0 Hz), 3.67 (q, 1H, J=7.0 Hz), 2.73 (d, 1H, J=9.5 Hz), 2.15-2.12 (m, 2H), 2.01-1.99 (m, 1H), 1.89 (dd, 1H, J=6.0, 3.0 Hz), 1.61 (dd, 1H, J=15.0, 6.0 Hz), 1.36 (t, 1H, J=3.5 Hz), 1.33-1.30 (m, 6H), 1.18 (t, 3H, J=7.0 Hz).

$^{13}$C NMR (125 MHz, CDCl$_3$) δ 178.11, 171.59, 146.32, 128.41, 127.07, 126.85, 73.33, 70.15, 62.07, 60.75, 56.66, 44.72, 36.78, 33.61, 26.24, 20.07, 14.37, 14.23.

FTIR (KBr) 3492 (s), 3303 (m), 3055 (w), 2981 (w), 2896 (w), 1722 (s), 1705 (s), 1289 (m), 1251 (m), 1177 (m) cm$^{-1}$.

Anal. Calcd for C$_{20}$H$_{27}$NO$_5$: C, 66.46; H, 7.52; N, 3.88. Found: C, 66.42; H, 7.44; N, 3.92.

Preparation 81

Ethyl 2-[((1R)-1-phenylethyl)amino](2S,4R,6R)-2-(ethoxycarbonyl)-4-fluorobicyclo[3.1.0]hexane-6-carboxylate

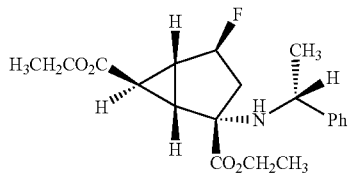

To a solution of ethyl 2-[((1R)-1-phenylethyl)amino](2S,4S,6R)-2-(ethoxycarbonyl)-4-hydroxybicyclo[3.1.0]hexane-6-carboxylate (59.0 g crude, 0.163 mol) in CH$_2$Cl$_2$ (690 mL) at −20° C. is added Deoxo-Fluor® (45.1 mL, 0.245 mol) over 15 minutes, maintaining the temperature between −15 and −20° C. The mixture is stirred for 20 minutes at this temperature and at 0° C. for 15 minutes before aqueous 15% Na$_2$CO$_3$ (650 ml) is slowly added while maintaining the temperature below 10° C. The layers are separated and the aqueous layer back extracted with CH$_2$Cl$_2$ (150 mL). The combined organic layers are dried (Na$_2$SO$_4$) and concentrated to a brown oil (73 g). The oil is purified on a pad of silica gel (400 g) eluting with EtOAc/heptane (1:6) to afford the title compound as a yellow oil (49.7 g, 84%).

$[\alpha]^{25}_D$ +36.2 (c 1.30, CHCl$_3$).

500 MHz $^1$H NMR (CDCl$_3$) δ 7.29-7.14 (m, 5H), 5.22 (ddt, 1H, J=8.0, 4.5 Hz, J$_{HF}$=56.0 Hz), 4.16 (dq, 1H, J=11.0, 7.0 Hz), 4.05 (dq, 1H, 11.0, 7.0 Hz), 3.96 (dq, 1H, 10.5, 7.0 Hz), 3.85 (dq, 10.5, 7.0 Hz), 3.66 (q, 1H, 6.5 Hz), 2.45 (dd, 1H, J=14.0, 8.0 Hz), 2.16-2.12 (m, 1H), 1.95 (t, 1H, J=3.5 Hz), 1.81 (dt, 1H, J=3.5 Hz, J$_{HF}$=3.5 Hz), 1.51 (ddd, 1H, J=14.0, 8.0 Hz, J$_{HF}$=22.0 Hz), 1.32 (d, 3H, J=6.5 Hz), 1.27 (t, 3H, J=7.0 Hz), 1.21 (t, 3H, J=7.0 Hz).

$^{13}$C NMR (125 MHz, CDCl$_3$) δ 175.29, 171.66, 146.21, 128.45, 127.03, 126.90, 92.65 (d, J$_{CF}$=182 Hz), 68.68 (d, J$_{CF}$=4.9 Hz), 61.70, 60.92, 56.13, 38.60 (d, J$_{CF}$=23.0 Hz), 33.07 (d, J$_{CF}$=7.6 Hz), 32.23 (d, J$_{CF}$=22.0 Hz), 26.26, 20.22 (d, J$_{CF}$=3.9 Hz), 14.41, 14.24.

FTIR (CHCl3) 3028 (w), 2983 (w), 1724 (s), 1705 (s), 1293 (m), 1242 (m), 1190 (m), 1037 (m), 1013 (m) cm$^{-1}$.

Anal. Calcd for C$_{20}$H$_{26}$FNO$_4$: C, 66.10; H, 7.21; N, 3.85. Found: C, 66.02; H, 7.00; N, 3.95.

Preparation 82

1R,2S,4R,5R,6R-2-amino-4-fluorobicyclo[3.1.0]hexane-2,6-dicarboxylic acid hydrochloride

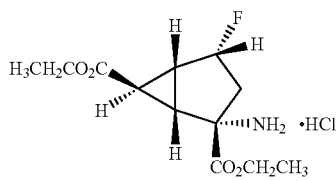

A mixture of ethyl 2-[((1R)-1-phenylethyl)amino](2S,4R,6R)-2-(ethoxycarbonyl)-4-fluorobicyclo[3.1.0]hexane-6-carboxylate (68.4 g, 0.188 mol), conc. HCl (15.7 mL, 0.188 mol), and 10% Pd/C (dry, 13.7 g) in EtOH (400 mL) is placed under hydrogen (50 psi) for 18 hours. The catalyst is filtered off and the filtrate is evaporated to give the title compound as an off-white foam (59.2 g, 106% corrected to 97% due to EtOH contamination). Crystallization from EtOAc/MTBE provides an analytically pure sample of the title compound as a white solid.

$[\alpha]^{25}_D$ +55.6 (c 1.17, CHCl$_3$).

mp 86-88° C.

500 MHz $^1$H NMR (CDCl$_3$) δ 9.20 (br s, 2H), 5.50 (ddt, 1H, J=8.0, 4.5 Hz, $J_{HF}$=56.0 Hz), 4.31 (q, 1H, J=7.0 Hz), 4.20-4.07 (m, 3H), 2.88 (t, 1H, J=3.0 Hz), 2.71 (dd, 1H, J=14.5, 8.0 Hz), 2.48-2.43 (m, 2H), 2.16 (ddd, 1H, J=14.5, 7.5 Hz, $J_{HF}$=22.0 Hz), 1.34 (t, 3H, J=7.0 Hz), 1.25 (t, 3H, J=7.0 Hz)

$^{13}$C NMR (125 MHz, CDCl$_3$) δ 171.12, 169.41, 91.94 (d, $J_{CF}$=189 Hz), 63.85, 63.66 (d, $J_{CF}$=3.8 Hz), 61.73, 34.55 (d, $J_{CF}$=26.4 Hz), 31.58 (d, $J_{CF}$=7.8 Hz), 30.80 (d, $J_{CF}$=24.1 Hz), 20.22, 14.31, 14.21.

FTIR (KBr) 3353 (m), 3173 (w), 2745 (m), 1729 (s), 1547 (m), 1294 (m), 1269 (m), 1195 (m), 1011 (m) cm$^{-1}$.

Anal. Calcd for C$_{12}$H$_{18}$FNO$_4$: C, 48.74; H, 6.48; N, 4.74. Found: C, 48.80; H, 6.41; N, 4.76.

Preparation 83

1R,2S,4R,5R,6R-2-amino-4-fluorobicyclo[3.1.0] hexane-2,6-dicarboxylic acid

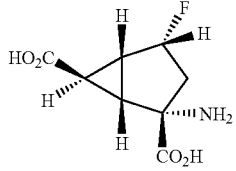

A solution of 3N NaOH (251 mL, 0.753 mol) is slowly added to 1R,2S,4R,5R,6R-2-amino-4-fluorobicyclo[3.1.0] hexane-2,6-dicarboxylic acid hydrochloride (59.2 g crude, 0.188 mol theory), maintaining the temperature below 26° C. After the mixture is stirred for 10 minutes, it is homogeneous. The mixture is stirred for 1.25 hours at room temperature before the pH is slowly lowered to pH 2.8 using conc. HCl while maintaining the temperature between 20 and 26° C. At pH 2.8, the mixture begins crystallizing, and the suspension is stirred at this pH for 10 minutes before the pH is lowered to 2.1 with conc. HCl. After another 15 minutes of stirring, i-PrOH (67 mL) is added and the suspension is cooled to 0° C. and stirred for 2 hours. The solid is collected and washed with 37 mL of cold H$_2$O/i-PrOH (4:1). The collected solid is dried in vacuo at 40° C. for 18 hours, affording the title compound as a white solid (33.1 g, 87% from the start of Preparation 23).

Preparation 84

Reslurry of 1R,2S,4R,5R,6R-2-amino-4-fluorobicyclo[3.1.0]hexane-2,6-dicarboxylic acid A stirred suspension of 1R,2S,4R,5R,6R-2-amino-4-fluorobicyclo[3.1.0]hexane-2,6-dicarboxylic acid (33.0 g, 0.162 mmol) in H$_2$O (165 mL) is warmed to 89° C. over 1 hour, and i-PrOH (41 mL) is added. The mixture is then stirred for 5 minutes at reflux (83° C.) before it is allowed to cool to room temperature and stir for 4 hours. The product is collected, washed with i-PrOH/H$_2$O (1:4, 40 mL) and i-PrOH (25 mL), and dried in vacuo at 40° C. for 18 hours to afford the title compound as a white solid (30.6 g, 93%).

Preparation 85

1R,2S,4R,5R,6R-2-Amino-4-fluorobicyclo[3.1.0] hexane-2,6-dicarboxylic acid ethyl ester

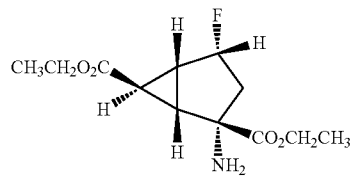

To a slurry of 1R,2S,4R,5R,6R-2-amino-4-fluorobicyclo[3.1.0]hexane-2,6-dicarboxylic acid (14.45 g, 71.12 mmol) in 202 mL of absolute ethanol at room temperature is added thionyl chloride (26 mL, 356 mmol) dropwise over 20 minutes. The slurry is heated to reflux and allowed to stir for 3 hours followed by cooling to room temperature overnight. The resultant solution is concentrated in vacuo to a residue that is diluted with 136 mL of ethyl acetate and treated with 306 mL of 10% aqueous sodium carbonate over 15 minutes with swirling by hand such that the final pH is 10. The layers are separated and the aqueous layer is washed with ethyl acetate (1×136 mL). The combined organic extracts are washed with brine (1×136 mL), dried (MgSO$_4$), filtered, and concentrated in vacuo to provide 17.07 g (93%) of the title compound as white solid.

FDMS: M$^+$+1=260.

Anal. calcd. For C$_{12}$H$_{18}$FNO$_4$.0.1H$_2$O: C, 55.21; H, 7.03; N, 5.37. Found: C, 55.10; H, 6.96; N, 5.22.

m.p.=64-66° C.

$[\alpha]_D^{25}$=+20 (c=0.96, MeOH), $[\alpha]_D^{25}$=+15 (c=1.21, DMSO)

Preparation 86

1R,2S,4R,5R,6R-2-[2'S-2'-(tert-butoxycarbonylamino)propionyl]amino-4-fluorobicyclo[3.1.0]hexane-2,6-dicarboxylic acid ethyl ester

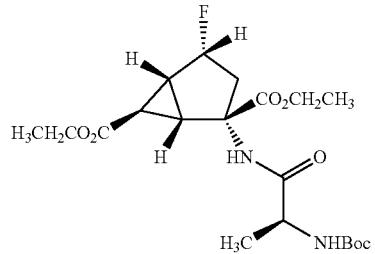

To a solution of N-Boc-L-alanine (38.62 g, 204 mmol) in 396 mL of methylene chloride at −22° C. under nitrogen is added N-methyl morpholine (22.44 mL, 204 mmol) followed by iso-butyl chloroformate (26.48 mL, 204 mmol) dropwise over 15 min such that the reaction temperature did not exceed −18° C. The resultant thin slurry is allowed to stir at −20° C. for 30 minutes at which time a solution of 1R,2S,4R,5R,6R-

2-amino-4-fluorobicyclo[3.1.0]hexane-2,6-dicarboxylic acid ethyl ester (49.46 g, 191 mmol) in 247 mL of methylene chloride is added over 40 min such that the reaction temperature did not exceed −16° C. Upon completion of the addition, the reaction is removed from the cooling bath and is allowed to stir at ambient temperature for 70 minutes at which time the reaction temperature had reached 15° C. and the color became faint orange. The reaction is treated with 408 mL of 1 N hydrochloric acid followed by stirring for 5 minutes and separation of the layers. The organic layer is washed with saturated aqueous sodium bicarbonate (1×408 mL), dried ($Na_2SO_4$), filtered, and concentrated in vacuo to a white foam (88.16 g).

FDMS: $M^++1=260$.

Anal. calcd. For $C_{12}H_{18}FNO_4 \cdot 0.1H_2O$: C, 55.21; H, 7.03; N, 5.37. Found: C, 55.10; H, 6.96; N, 5.22.

m.p.=64-66° C.

$[\alpha]_D^{25}=+20$ (c=0.96, MeOH), $[\alpha]_D^{25}=+15$ (c=1.21, DMSO).

Preparation 87

1R,2S,4R,5R,6R-2-[2'S-2'-(tert-butoxycarbonylamino)propionyl]amino-4-fluorobicyclo[3.1.0]hexane-2,6-dicarboxylic acid

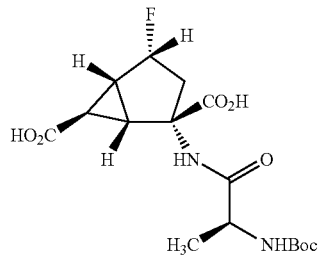

To a solution of 1R,2S,4R,5R,6R-2-[2'S-2'-(tert-butoxycarbonylamino)propionyl]amino-4-fluorobicyclo[3.1.0]hexane-2,6-dicarboxylic acid ethyl ester (88.16 g, 191 mmol) in 238 mL of tetrahydrofuran at room temperature is added 238 mL (477 mmol) of 2N sodium hydroxide. The biphasic mixture is allowed to stir vigorously at room temperature for 2.5 hours at which time the reaction is homogeneous. The mixture is diluted with 238 mL of t-butyl methyl ether followed by mixing and separation of the layers. The aqueous layer is further diluted with 238 mL of water and filtered to remove particulate matter. The solution is treated with concentrated HCl (42.9 mL, 515 mmol) over 30 minutes optionally followed by seeding with the title compound and stirring for 1 hour. The resultant slurry is filtered, washed with water (2×100 mL), and vacuum dried at 45° C. for 40 hours to provide 72.2 g of the title compound as a white solid. A portion of the solid (69.5 g) is allowed to stir with 490 mL of acetone for 1 hour to produce a hazy solution that is filtered, washing with acetone (2×100 mL). The filtrate is concentrated in vacuo to a white foam which is further dried in vacuo at 45° C. for 16 hours to provide 61.8 g (corrected for 12% wt/wt acetone) of the title compound.

EXAMPLE 1

(1R,4S,5S,6S)-4-(2'S-Aminopropionyl)amino-]-2,2-dioxo-2$\lambda^6$-thia-bicyclo[3.1.0]hexane-4,6-dicarboxylic acid hydrochloride

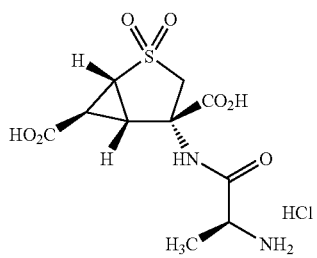

To a suspension of (1R,4S,5S,6S)-4-(2'S-tert-butoxycarbonylamino-propionylamino)-2,2-dioxo-2$\lambda^6$-thia-bicyclo[3.1.0]hexane-4,6-dicarboxylic acid (110.0 g, 271 mmol, Preparation 3) in 563 mL of ethyl acetate added a solution of hydrogen chloride in ethyl acetate (3.7 M, 514 mL) over 20 minutes. After the suspension stirs for 2.5 h, filter and wash the cake with ethyl acetate (1×200 mL, 1×115 mL). After vacuum drying at 46° C. for 18 hours, the title compound is collected as a white solid (85.77 g, 92%).

$^1$H NMR (300 MHz, Methanol-$d_4$) δ: 4.12 (brd, 1H, J=14.6 Hz), 3.94 (q, 1H, J=7.1 Hz), 3.52 (ddd, 1H, J=7.0, 3.9, 0.9 Hz), 3.16 (d, 1H, J=14.6 Hz), 3.02 (dd, 1H, J=7.0, 4.4 Hz), 2.49 (t, 1H, J=4.1 Hz), 1.52 (d, 3H, J=7.1 Hz).

EXAMPLE 2

(1R,4S,5S,6S)-4-(2'S-2'-Aminopropionyl)amino-2,2-dioxo-2$\lambda^6$-thia-bicyclo[3.1.0.]hexane-4,6-dicarboxylic acid tosylate

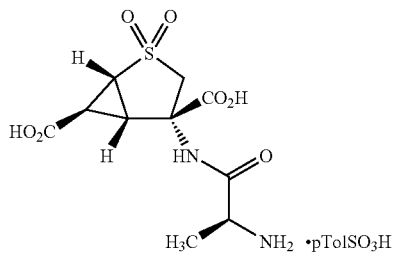

A suspension of (1R,4S,5S,6S)-4-(2'S-tert-butoxycarbonylamino-propionylamino)-2,2-dioxo-2$\lambda^6$-thia-bicyclo[3.1.0]hexane-4,6-dicarboxylic acid (300 mg, 0.738 mmol, Preparation 3) and toluenesulfonic acid monohydrate (140 mg, 0.738 mmol) in toluene (3 mL) is heated to 75° C. and stirred for 45 min before it is allowed to cool to room temperature and stir for 16 hours. Filter the suspension and wash the cake with toluene (2×1 mL). After vacuum drying at 45° C. for 1 hour, 307 mg (87%) of the title compound is collected as a white solid.

mp (DSC) 233° C.

$^1$H NMR (500 MHz, $CD_3OD$) δ 7.70 (d, 2H, J=8.5 Hz), 7.24 (d, 2H, J=8.0 Hz), 4.11 (d, 1H, J=15 Hz), 3.94 (q, 1H, J=7.0 Hz), 3.53 (dd, 1H, J=7.0, 4.0 Hz), 3.13 (dd, 1H, J=14, 1.0 Hz), 3.02 (dd, 1H, J=7.0, 4.5 Hz), 2.48 (t, 1H, J=4.5 Hz), 2.37 (s, 3H), 1.52 (d, 3H, J=7.5 Hz).
$^{13}$C NMR (125 MHz, CD$_3$OD) δ 170.70, 170.32, 169.80, 142.04, 140.78, 128.79, 125.79, 60.20, 54.73, 48.77, 42.44, 30.84, 22.22, 20.20, 16.09.

EXAMPLE 3

(1R,4S,5S,6S)-4-(2'S-Amino-3'-hydroxy-propionyl)-amino-2,2-dixoxo-2λ$^6$-thia-bicyclo[3.1.0]hexane-4,6-dicarboxylic acid hydrochloric acid

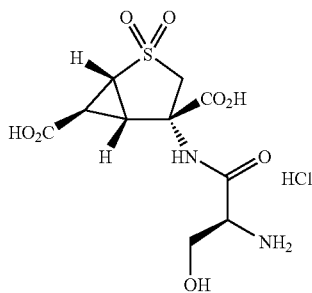

Prepare according to General Procedure C using (1R,4S,5S,6S)-4-(3'-acetoxy-2'S-tert-butoxycarbonylamino-propionyl)-amino-2,2-dioxo-2λ$^6$-thiabicyclo[3.1.0]hexane-4,6-dicarboxylic acid dimethyl ester (380 mg, 0.77 mmoles, Preparation 15).
$[α]_D^{23}$=−19.23 (c=0.52, MeOH).
$^1$H NMR (400 MHz, CD$_3$OD) δ 2.48 (1H, t, J=4.0 Hz), 3.04 (1H, dd, J=4.4, 7.3 Hz), 3.17 (1H, d, J=14.7 Hz), 3.51 (1H, dd, J=4.4, 7.0 Hz), 3.77 (1H, dd, J=7.0, 10.6 Hz), 3.94-4.12 (3H, m).
Anal Calcd for C$_{10}$H$_{14}$N$_2$O$_8$S.HCl.H$_2$O: C, 31.88; H, 4.55; N, 7.44; Cl, 9.41. Found: C, 31.53; H, 4.40; N, 7.32; Cl, 9.24.
HRMS calcd for C$_{10}$H$_{15}$N$_2$O$_8$S, 323.0549. Found, 323.0533.

EXAMPLE 4

(1R,4S,5S,6S)-4-[(Pyrrolidine-2'S-carbonyl)-amino]-2,2-dioxo-2λ$^6$-thia-bicyclo[3.1.0.]hexane-4,6-dicarboxylic acid hydrochloride

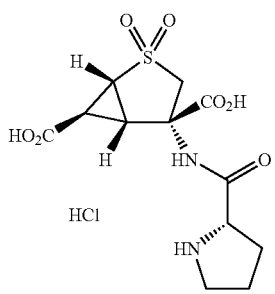

Prepare according to General Procedure C employing (1R,4S,5S,6S)-4-[(1'-tert-butoxycarbonyl-pyrrolidine-2'S-carbonyl)-amino]-2,2-dioxo-2λ$^6$-thia-bicyclo[3.1.0.]hexane-4,6-dicarboxylic acid dimethyl ester (0.8 g, 1.7 mmol, Preparation 11) to yield 0.42 g (67.0%) of the title compound.

$[α]_D^{23}$=−32 (c=1.00, CH$_3$OH).
$^1$H NMR (300 MHz, CD$_3$OD) δ 1.98-2.12 (3H, m), 2.40-2.50 (1H, m), 2.52 (1H, t, J=4.4 Hz), 2.99 (1H, dd, J=4.4, 7.0 Hz), 3.2 (1H, d, J=14.7 Hz), 3.29-3.42 (3H, m), 3.54 (1H, m), 4.13 (1H, d, J=15.8 Hz), 4.30 (1H, dd, J=6.2, 9.2 Hz).
HRMS calcd for C$_{12}$H$_{17}$N$_2$O$_7$S, 333.0756. Found, 333.0740.

EXAMPLE 5

(1R,4S,5S,6S)-4-(2'S-Amino-4'-methylsulfanyl-butyrylamino)-2,2-dioxo-2λ$^6$-thia-bicyclo[3.1.0.]hexane-4,6-dicarboxylic acid hydrochloride

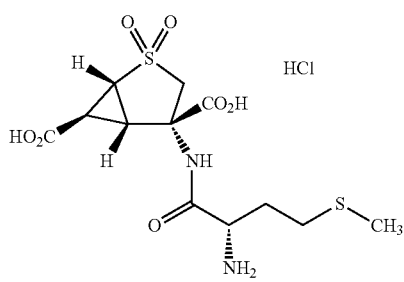

Prepare according to General Procedure C employing (1R,4S,5S,6S)-4-(2'S-tert-butoxycarbonylamino-4'-methylsulfanyl-butyrylamino)-2,2-dioxo-2λ$^6$-thia-bicyclo[3.1.0.]hexane-4,6-dicarboxylic acid dimethyl ester (0.77 g, 1.6 mmol, Preparation 12) to yield 0.41 g (54.9%) of the title compound.
$[α]_D^{23}$=+4 (c=1.00, MeOH).
$^1$H NMR (300 MHz, CD$_3$OD) δ 2.1-2.2 (2H, m), 2.13 (3H, s), 2.47 (1H, t, J=4.4 Hz), 2.58-2.63 (2H, m), 3.02 (1H, dd, J=4.0, 7.0 Hz), 3.12 (1H, d, J=14.7 Hz), 3.52 (1H, dd, J=3.3, 6.6 Hz), 3.98 (1H, t, J=6.2 Hz), 4.14 (1H, d, J=14.7 Hz).
HRMS calcd for C$_{12}$H$_{19}$N$_2$O$_7$S$_2$, 367.0634. Found, 367.0634.

EXAMPLE 6

(1R,4S,5S,6S)-4-[2'S-Amino-3'-(1H-indol-3-yl)-propionylamino]-2,2-dioxo-2λ$^6$-thia-bicyclo[3.1.0]hexane-4,6-dicarboxylic acid hydrochloride

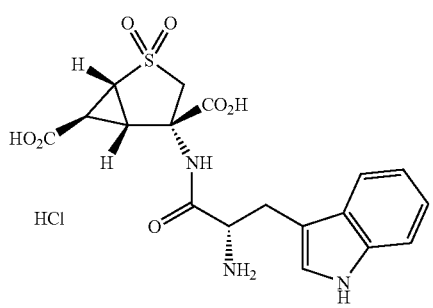

Prepare according to General Procedure C employing (1R,4S,5S,6S)-4-[2'S-tert-butoxycarbonylamino-3'-(1-tert-butoxycarbonyl-1H-indol-3-yl)-propionylamino]-2,2-dioxo-2λ$^6$-thia-bicyclo[3.1.0.]hexane-4,6-dicarboxylic acid dimethyl ester (0.54 g, 0.83 mmol, Preparation 13) to yield 0.28 g (73.6%) of the title compound.

[α]$_D^{23}$=+7.8 (c=1.02, CH$_3$OH).

$^1$H NMR (300 MHz, CD$_3$OD) δ 2.47-2.53 (1H, m), 3.05-3.18 (3H, m), 3.44-3.57 (2H, m), 4.13-4.23 (2H, m), 7.07-7.41 (3H, m), 7.71-7.78 (2H, m), 8.22 (1H, app d, J=7.7 Hz).

Anal Calcd for C$_{18}$H$_{19}$N$_3$O$_7$S.HCl: C, 47.22; H, 4.40: N, 9.18. Found: C, 46.51; H, 3.96; N, 8.54.

MS (ES) m/z 420.1 [M−1]$^−$.

EXAMPLE 7

(1R,4S,5S,6S)-4-[2'S-Amino-3'-(4-hydroxy-phenyl)-propionylamino]-2,2-dioxo-2λ$^6$-thia-bicyclo[3.1.0.]hexane-4,6-dicarboxylic acid hydrochloride

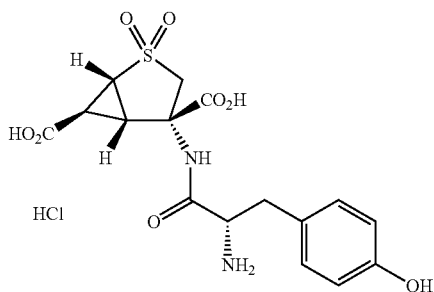

Prepare according to General Procedure C employing (1R,4S,5S,6S)-4-[2'S-tert-butoxycarbonylamino-3'-(4-tert-butoxycarbonyloxy-phenyl)-propionylamino]-2,2-dioxo-2λ$^6$-thia-bicyclo[3.1.0.]hexane-4,6-dicarboxylic acid dimethyl ester (0.33 g, 0.53 mmol, Preparation 14) to yield 0.13 g (56.4%) of the title compound.

[α]$_D^{23}$=−6 (c=1.00, H$_2$O).

$^1$H NMR (300 MHz, CD$_3$OD) δ 2.47 (1H, t, J=4.0 Hz), 2.87 (1H, dd, J=9.2, 14.7 Hz), 3.05-3.12 (2H, m), 3.23 (1H, dd, J=5.1, 14.7 Hz), 3.55 (1H, dd, J=4.0, 7.0 Hz), 4.00 (1H, dd, J=4.8, 9.2 Hz), 4.13 (1H, d, J=14.7 Hz), 6.80 (2H, d, J=8.4 Hz), 7.13 (2H, d, 8.8 Hz).

HRMS calcd for C$_{16}$H$_{19}$N$_2$O$_8$S, 399.0862. Found, 399.0844.

EXAMPLE 8

(1R,4S,5S,6S)-4-(2'S-Amino-3'-phenyl-propionylamino)-2,2-dioxo-2λ$^6$-thia-bicyclo[3.1.0]hexane-4,6-dicarboxylic acid hydrochloride

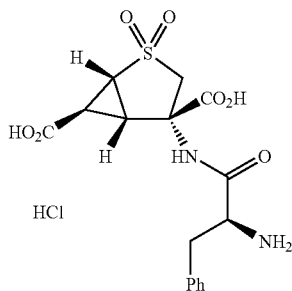

Prepare according to General Procedure C using (1R,4S,5S,6S)-4-(2'S-tert-butoxycarbonylamino-3'-phenyl-propionylamino)-2,2-dioxo-2λ$^6$-thia-bicyclo[3.1.0]hexane-4,6-dicarboxylic acid dimethyl ester (Preparation 5). Yield 0.55 g (85%, 1.31 mmol) of a white solid.

[α]$_D^{23}$=+4.17 (c=0.48, MeOH).

$^1$H NMR (300 MHz, CD$_3$OD) δ 2.45 (1H, t, J=4.0 Hz), 2.98 (1H, dd, J=9.2, 4.7 Hz), 3.06 (1H, dd, J=4.4, 7.0 Hz), 3.10 (1H, d, J=14.6 Hz), 3.33 (1H, dd, J=4.8, 13.6 Hz), 3.52 (1H, dd, J=3.3, 7.3 Hz), 4.08 (1H, dd, J=5.1, 8.8 Hz), 4.10 (1H, d, J=15.4 Hz), 7.31-7.42 (5H, m).

$^{13}$C NMR (300 MHz, D$_2$O w/1,4-dioxane): δ 172.55, 171.94, 170.01, 134.31, 130.39, 130.27, 130.01, 129.00, 61.38, 54.76, 54.37, 43.07, 37.36, 31.57, 23.18.

Anal Calcd for C$_{16}$H$_{18}$N$_2$O$_7$S.1.5HCl: C, 43.97; H, 4.50; N, 6.41. Found: C, 43.59; H, 4.17; N, 6.46.

MS (ES) m/z found 383.1 [M+H]$^+$.

HRMS calcd for C$_{16}$H$_{19}$N$_2$O$_7$S [M+H]$^+$: 383.0913. Found: 383.0923.

EXAMPLE 9

(1R,4S,5S,6S)-4-(2'S-Amino-3'S-methyl-pentanonylamino)-2,2-dioxo-2λ$^6$-thia-bicyclo[3.1.0]hexane-4,6-dicarboxylic acid hydrochloride

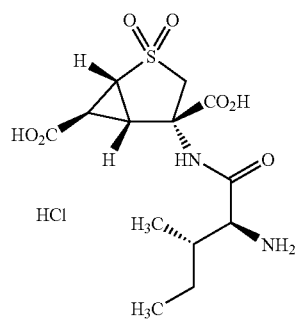

Prepare according to General Procedure C using (1R,4S,5S,6S)-4-(2'S-tert-butoxycarbonylamino-3'S-methyl-pentanoylamino)-2,2-dioxo-2λ$^6$-thia-bicyclo[3.1.0]hexane-4,6-dicarboxylic acid dimethyl ester (Preparation 6). Yield 0.43 g (80%, 1.12 mmol) of a white solid.

[α]$_D^{23}$=+4.08 (c=0.49, MeOH).

$^1$H NMR (300 MHz, CD$_3$OD) δ 0.98 (3H, t, J=7.3 Hz), 1.07 (3H, d, J=7.0 Hz), 1.15-1.24 (1H, m), 1.53-1.62 (1H, m), 1.95-2.04 (1H, m), 2.44 (1H, t, J=4.0 Hz), 3.06 (1H, dd, J=4.4, 7.0 Hz), 3.14 (1H, d, J=15.0 Hz), 3.52 (1H, dd, J=3.7, 7.0 Hz), 3.73 (1H, d, J=5.1 Hz), 4.10 (1H, d, J=14.7 Hz).

Anal Calcd for C$_{13}$H$_{20}$N$_2$O$_7$S.HCl.0.5H$_2$O: C, 39.64; H, 5.63; N, 7.11. Found: C, 39.38; H, 5.39; N, 7.04.

MS (ES) m/z found 349.1 [M+H]$^+$.

HRMS (ES) calcd for C$_{13}$H$_{21}$N$_2$O$_7$S [M+H]$^+$, 349.1069. Found, 349.1086.

EXAMPLE 10

(1R,4S,5S,6S)-4-(2'S-Amino-3'-methyl-butyrylamino)-2,2-dioxo-2λ⁶-thia-bicyclo[3.1.0]hexane-4,6-dicarboxylic acid hydrochloride

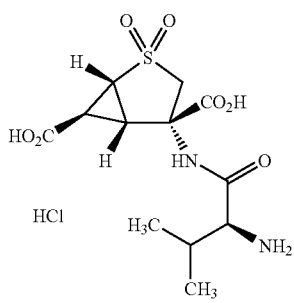

Prepare according to General Procedure C using (1R,4S,5S,6S)-4-(2'S-tert-butoxycarbonylamino-3'-methyl-butyrylamino)-2,2-dioxo-2λ⁶-thia-bicyclo[3.1.0]hexane-4,6-dicarboxylic acid dimethyl ester (Preparation 7). Yield 0.18 g (88%, 0.49 mmol) of a white solid as the HCl salt.

$[α]_D^{23}$=+7.84 (c=0.51, MeOH).

¹H NMR (300 MHz, CD₃OD) δ 1.04 (3H, d, J=6.6 Hz), 1.09 (3H, d, J=7.0 Hz), 2.22-2.29 (1H, m), 2.44 (1H, t, J=4.0 Hz), 3.05 (1H, dd, J=4.4, 7.0 Hz), 3.10 (1H, d, J=14.7 Hz), 3.52 (1H, dd, J=4.0, 7.3 Hz), 3.67 (1H, d, J=5.5 Hz), 4.10 (1H, d, J=14.7 Hz).

Anal Calcd for $C_{12}H_{18}N_2O_7S.HCl.0.4H_2O$: C, 38.12; H, 5.20; N, 7.41. Found: C, 37.78; H, 4.90; N, 7.15.

MS (ES) m/z found 335.1 [M+H]⁺.

EXAMPLE 11

(1R,4S,5S,6S)-4-(2'S-Amino-4'-methyl-pentanoylamino)-2,2-dioxo-2λ⁶-thia-bicyclo[3.1.0]hexane-4,6-dicarboxylic acid hydrochloride

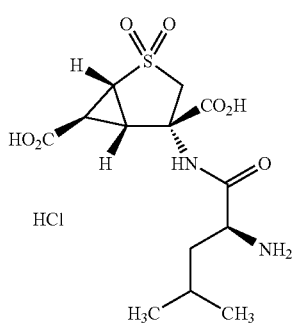

Prepare according to General Procedure C using (1R,4S,5S,6S)-4-(2'S-tert-butoxycarbonylamino-4'-methyl-pentanoylamino)-2,2-dioxo-2λ⁶-thia-bicyclo[3.1.0]hexane-4,6-dicarboxylic acid dimethyl ester (Preparation 8). Yield 0.50 g (76%, 1.30 mmol) of a white solid as the HCl salt.

$[α]_D^{23}$=-4.0 (c=0.50, MeOH).

¹H NMR (300 MHz, CD₃OD) δ 1.00 (3H, d, J=5.5 Hz), 1.02 (3H, d, J=5.9 Hz), 1.62-1.79 (3H, m), 2.42 (1H, t, J=4.0 Hz), 3.04 (1H, dd, J=4.4, 7.3 Hz), 3.13 (1H, d, J=15.0 Hz), 3.52 (1H, dd, J=3.3, 7.0 Hz), 3.84-3.89 (1H, m), 4.10 (1H, d, J=15.0 Hz).

Anal Calcd for $C_{13}H_{20}N_2O_7S.HCl.0.3H_2O$: C, 40.01; H, 5.58; N, 7.18. Found: C, 39.66; H, 5.57; N, 6.99.

MS (ES) m/z found 349.1 [M+H]⁺.

EXAMPLE 12

(1R,4S,5S,6S)-4-(2'S,6'-Diamino-hexanoylamino)-2,2-dioxo-2λ⁶-thia-bicyclo[3.1.0]hexane-4,6-dicarboxylic acid bis hydrochloride

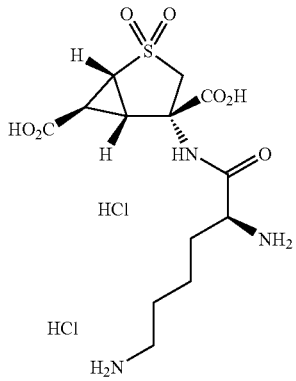

Prepare according to General Procedure C using (1R,4S,5S,6S)-4-(2'S,6'-bis-tert-butoxycarbonylamino-hexanoylamino)-2,2-dioxo-2λ⁶-thia-bicyclo[3.1.0]hexane-4,6-dicarboxylic acid dimethyl ester (Preparation 9). Yield 0.56 g (86%, 1.28 mmol) of a white solid as the bis hydrochloride salt.

$[α]_D^{23}$=-4.0 (c=0.50, MeOH).

¹H NMR (300 MHz, CD₃OD) δ 1.48-1.55 (2H, m), 1.67-1.74 (2H, m), 1.89-1.97 (2H, m), 2.47 (1H, t, J=4.0 Hz), 2.97 (2H, app t, J=4.0), 3.08 (1H, dd, J=4.4, 7.0 Hz), 3.20 (1H, d, J=15.0 Hz), 3.53 (1H, dd, J=3.7, 7.0 Hz), 3.93 (1H, app. t, J=6.2 Hz), 4.08 (1H, d, J=14.7 Hz).

Anal Calcd for $C_{13}H_{21}N_3O_7S.2HCl.0.2H_2O$: C, 35.49; H, 5.36; N, 9.55. Found: C, 35.30; H, 5.48; N, 9.42.

MS (ES) m/z found 364.1 [M+H]⁺.

EXAMPLE 13

(1R,4S,5S,6S)-4-(2'S-Amino-4'-carbamoyl-butyrylamino)-2,2-dioxo-2λ$^6$-thia-bicyclo[3.1.0]hexane-4,6-dicarboxylic acid hydrochloride

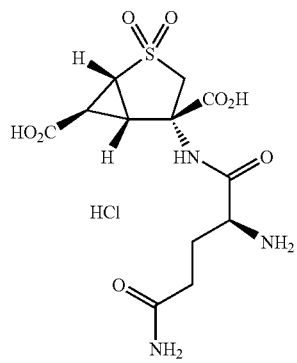

Stir (1R,4S,5S,6S)-4-[2'S-tert-butoxycarbonylamino-4'-(trityl-carbamoyl)-butyrylamino]-2,2-dioxo-2λ$^6$-thia-bicyclo[3.1.0]hexane-4,6-dicarboxylic acid dimethyl ester (0.48 g, 0.65 mmol, Preparation 10) in a 1:1 mixture of 2.5 N LiOH and THF (6 mL total volume) at room temperature for 4 hours. Adjust the reaction mixture to pH=2 with 1N HCl and extract the product with ethyl acetate. Combine all organics, wash with brine, dry over $MgSO_4$ and concentrate to yield 0.46 g of (1R,4S,5S,6S)-4-[2'S-tert-butoxycarbonylamino-4'-(trityl-carbamoyl)-butyrylamino]-2,2-dioxo-2λ$^6$-thia-bicyclo[3.1.0]hexane-4,6-dicarboxylic acid as a white foam. Dissolve the diacid in DCM and stir at room temperature as anisole (0.28 g, 2.6 mmol) and then TFA (3.70 g, 32.5 mmol) are consecutively added. Stir the resulting reaction mixture at room temperature for 2 hours and concentrated in vacuo. Triturate the resulting yellow oil in $Et_2O$ until a freely flowing white precipitate forms. Collect the TFA salt by vacuum filtration under $N_2$ blanket. Dissolve product in 1 mL 1N HCl and subject to lyophilization to afford the desired product as the HCl salt. Yield 0.16 g (62%, 0.40 mmol) of a white solid.

$[\alpha]_D^{23}$=+8.0 (c=1.0, $H_2O$).

$^1$H NMR (300 MHz, $CD_3OD$) δ 2.00-2.08 (2H, m), 2.37-2.41 (3H, m), 2.93 (1H, dd, J=4.4, 7.3 Hz), 3.04 (1H, d, J=14.7 Hz), 3.45 (1H, dd, J=3.7, 7.0 Hz), 3.86 (1H, app. t, J=5.9 Hz), 4.05 (1H, d, J=14.7 Hz).

Anal Calcd for $C_{12}H_{17}N_3O_8S \cdot HCl \cdot 2.0H_2O$: C, 33.07; H, 5.09; N, 9.64. Found: C, 33.37; H, 4.69; N, 9.39.

MS (ES) m/z found 363.9 [M+H]$^+$.

HRMS (ES) calcd for $C_{12}H_{18}N_3O_8S$ [M+H]$^+$: 364.0815. Found: 364.0825.

EXAMPLE 14

1R,2S,4R,5R,6R-2-(2'S-2'-Aminopropionyl)amino-4-fluorobicyclo[3.1.0]hexane-2,6-dicarboxylic acid hydrochloride

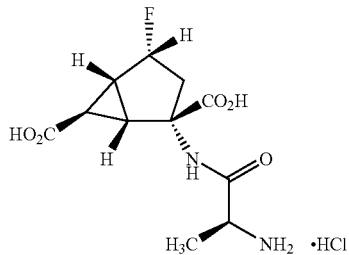

Stir a slurry of (1R,2S,4R,5R,6R)-2-(2'S-2'-(tert-butoxycarbonylamino)propionyl)amino-4-fluoro-bicyclo[3.1.0]hexane-2,6-dicarboxylic acid (53.0 g corrected for acetone, 142 mmol) in 447 mL of acetone at 50° C. for 35 minutes. Filter the hazy solution to clarify the solution, followed by rinsing with 100 mL of acetone. Add 22.1 mL (265 mmol) of concentrated hydrochloric acid dropwise to the clear, off-white filtrate over 5 minutes. Warm the mixture to 45-50° C. and stir for 90 minutes. Optionally seed the mixture with (1R,2S,4R,5R,6R)-2-(2'S-aminopropionyl)amino-4-fluoro-bicyclo[3.1.0]hexane-2,6-dicarboxylic acid hydrochloride, followed by turning off the heat and allowing to gradually cool to room temperature. After 2 hours the temperature reaches 25° C. and acetone (942 mL) is added to the slurry over 90 minutes. Stir the slurry an additional 16 hours, followed by filtration, washing with acetone (2×200 mL), and vacuum drying at 45° C. for 9 hours and at room temperature for another 64 hours to produce 40.2 g (91%) of the title compound as a white solid.

Recrystallization

Dissolve 1.06 g in 0.5 mL of water and 2.12 mL of acetone with heating at 50° C. followed by dilution with another 5.3 mL of acetone and optionally seeding. Add another 4.2 mL of acetone to the faintly cloudy mixture optionally followed again by seeding, turning off the heat, and allowing gradual cooling to room temperature over 1 hour. Dilute the resultant slurry further with another 9.5 mL of acetone over 30 minutes followed by stirring for 15 hours. Upon filtering, washing with acetone (2×5 mL), and vacuum drying at 45° C. for 10 hours and at room temperature for 60 hours, 0.905 g (85% recovery) of the title compound is obtained as a white solid.

mp (DSC) 183° C.

$[\alpha]^{25}_D$ +33° (c 1.06, $CH_3OH$).

500 MHz $^1$H NMR ($CD_3OD$) δ 5.58-5.42 (m, 1H), 3.92 (q, 1H, J=7.0 Hz), 2.96 (dd, 1H, J=14, 8.0 Hz), 2.41-2.39 (m, 1H), 2.35-2.30 (m, 1H), 2.10 (t, 1H, J=3.0 Hz), 1.52 (d, 3H, J=7.5 Hz), 1.51-1.42 (m, 1H).

$^{13}$C NMR (125 MHz, $CD_3OD$) δ 173.74, 173.62, 170.00, 93.48 and 92.04 (C—F splitting), 63.95 and 63.92 (C—F splitting), 48.80, 36.89 and 36.70 (C—F splitting), 32.97 and 32.91 (C—F splitting), 30.05 and 29.87 (C—F splitting), 19.37, 16.28.

FTIR (DRIFT) 3430 (w), 3016 (s), 1721 (s), 1662 (s), 1496 (s), 1190 (m), 1024 (m), 637 (w) cm$^{-1}$.

EXAMPLE 15

1R,2S,4R,5R,6R-2-(2'S-2'-Aminopropionyl)amino-4-fluorobicyclo[3.1.0]hexane-2,6-dicarboxylic acid mesylate

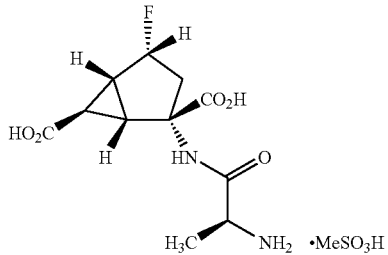

A slurry of (1R,2S,4R,5R,6R)-2-[2'S-(tert-butoxycarbonylamino)propionyl]-amino-4-fluorobicyclo[3.1.0]hexane-2,6-dicarboxylic acid (1.87 g corrected, 4.98 mmol, Preparation 18) in 16.8 mL of acetone is allowed to stir at 50° C. for 15 minutes. The hazy solution is filtered to clarify the solution followed by rinsing with acetone (3×1.25 mL). The clear filtrate is diluted with 0.935 mL of water, placed in a heating bath at 50° C., and treated with 0.647 mL (9.97 mmol) of methanesulfonic acid dropwise (gas evolution observed). A white slurry is produced after 25 minutes. After stirring a total of 2 hours, another 35.5 mL of acetone is added over 5-10 minutes. The heat is turned off and the slurry is allowed to cool gradually to room temperature over 2 hours followed by filtration, washing with acetone (2×8 mL), and vacuum drying at 45° C. for 14 hours to give 1.77 g (95%) of the title compound as a faint pink solid. A sample of this material is recrystallized as follows: 1.65 g is dissolved in 1.16 mL of water and 4.95 mL of acetone with heating at 50° C. followed by dilution with another 1.65 mL of acetone and optionally seeding. The heat is turned off and the mixture is allowed to gradually cool to room temperature. Acetone (26.4 mL) is added simultaneously over 40 min. The resultant slurry is allowed to stir an additional 3 hours. Upon filtering, washing with acetone (2×6 mL), and vacuum drying at 45° C. for 6 h and at room temperature for 60 hours, 1.59 g (96% recovery) of the title compound is obtained as a white solid:

mp (DSC) 206° C.

$[\alpha]^{25}_D$ +30 (c 1.05, CH$_3$OH).

$^1$H NMR (500 MHz, CD$_3$OD) δ 5.58-5.42 (m, 1H), 3.92 (q, 1H, J=7.0 Hz), 2.96 (dd, 1H, J=14, 8.0 Hz), 2.70 (s, 3H), 2.41-2.39 (m, 1H), 2.35-2.30 (m, 1H), 2.10 (t, 1H, J=3.0 Hz), 1.52 (d, 3H, J=7.5 Hz), 1.51-1.42 (m, 1H).

$^{13}$C NMR (125 MHz, CD$_3$OD) δ 173.73, 173.61, 170.02, 93.50 and 92.05 (C—F splitting), 63.91, 48.79, 38.30, 36.89 and 36.70 (C—F splitting), 32.97 and 32.91 (C—F splitting), 30.02 and 29.84 (C—F splitting), 19.37, 16.26.

FTIR (DRIFT) 3472 (w), 3077 (s), 1717 (s), 1691 (s), 1557 (m), 1220 (s), 1019 (m), 781 (m), 563 (m) cm$^{-1}$.

Anal. Cald for C$_{12}$H$_{19}$FN$_2$O$_8$S: C, 38.92; H, 5.17; N, 7.56. Found: C, 38.96; H, 4.97; N, 7.51.

EXAMPLE 16

1R,2S,4R,5R,6R-2-(2'S-2'-Aminopropionyl)amino-4-fluorobicyclo[3.1.0]hexane-2,6-dicarboxylic acid esylate

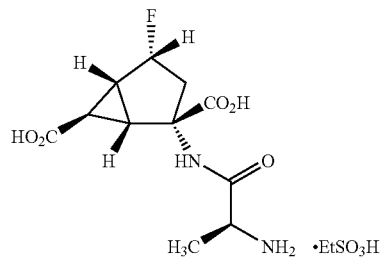

A slurry of (1R,2S,4R,5R,6R)-2-[2'S-(tert-butoxycarbonylamino)propionyl]-amino-4-fluorobicyclo[3.1.0]hexane-2,6-dicarboxylic acid (0.2 g, 0.534 mmol, Preparation 18) in 1.8 mL of acetone is allowed to stir at 50° C. for 5 minutes. The hazy solution is filtered to clarify the solution followed by rinsing with acetone (1×0.4 mL). The clear filtrate is diluted with 0.1 mL of water, placed in a heating bath at 50° C., and treated with 0.124 mL (1.07 mmol) of ethanesulfonic acid dropwise (gas evolution observed). A white slurry is produced after 90 minutes. After stifling a total of 2 hours, another 1.8 mL of acetone is added over 5 min. The heat is turned off and the slurry is allowed to cool gradually to room temperature over 1 hours followed by stirring an additional 2 hours. Filtration, washing with acetone (2×1 mL), and vacuum drying at 45° C. for 4 hours and at room temperature for 60 hours afforded 0.173 g (84%) of the title compound as a white solid.

mp (DSC) 210° C. (decomp).

$^1$H NMR (500 MHz, CD$_3$OD) δ 5.58-5.42 (m, 1H), 3.92 (q, 1H, J=7.0 Hz), 2.96 (dd, 1H, J=14, 8.0 Hz), 2.80 (q, 2H, 7.3 Hz), 2.42-2.37 (m, 1H), 2.35-2.30 (m, 1H), 2.09 (t, 1H, J=3.0 Hz), 1.52 (d, 3H, J=7.5 Hz), 1.51-1.40 (m, 1H), 1.30 (t, 3H, J=7.5 Hz).

EXAMPLE 17

1R,2S,4R,5R,6R-2-(2'S-2'-Aminopropionyl)amino-4-fluorobicyclo[3.1.0]hexane-2,6-dicarboxylic acid besylate

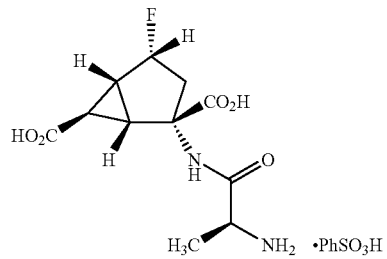

A slurry of (1R,2S,4R,5R,6R)-2-[2'S-(tert-butoxycarbonylamino)propionyl]-amino-4-fluorobicyclo[3.1.0]hexane-2,6-dicarboxylic acid (0.402 g 1.07 mmol, Preparation 18) in 3.6 mL of acetone is allowed to stir at 50° C. for 10 minutes.

The hazy solution is treated with a small scoop of celite and filtered to clarify the solution followed by rinsing with acetone (2×0.4 mL). The clear filtrate is placed in a heating bath at 50° C., and treated with 226 mg (90%, 1.29 mmol) of benzenesulfonic acid as a solution in 0.113 mL of water followed by a rinse with 0.4 mL of acetone (gas evolution observed). After stirring at gentle reflux for 4 hours, the heat is turned off and the reaction is treated with 8 mL of acetone over 10 minutes optionally followed by seeding. A slurry had formed over 1 hour which is diluted with 3.2 mL of acetone followed by stirring at room temperature an additional 15.5 hours. Filtration, washing with acetone (2×10 mL) and drying in vacuo at 45° C. for 24 h provided 313 mg (62% corrected for 10 wt % acetone) of the title compound as a white solid.

mp (DSC) 132° C.

$^1$H NMR (500 MHz, CD$_3$OD) δ 7.86-7.80 (m, 2H), 7.46-7.37 (m, 3H), 5.58-5.42 (m, 1H), 3.92 (q, 1H, J=7.0 Hz), 2.96 (dd, 1H, J=14, 8.0 Hz), 2.42-2.37 (m, 1H), 2.35-2.30 (m, 2H), 2.09 (t, 1H, J=3.0 Hz), 1.52 (d, 3H, J=7.5 Hz), 1.51-1.40 (m, 1H).

EXAMPLE 18

1R,2S,4R,5R,6R-2-(2'S-2'-Aminopropionyl)amino-4-fluorobicyclo[3.1.0]hexane-2,6-dicarboxylic acid tosylate

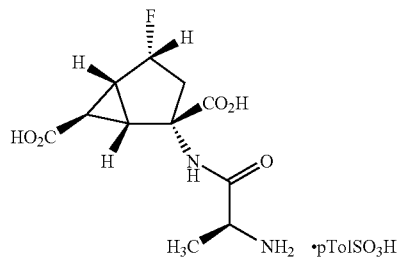

A slurry of (1R,2S,4R,5R,6R)-2-[2'S-(tert-butoxycarbonylamino)propionyl]-amino-4-fluorobicyclo[3.1.0]hexane-2,6-dicarboxylic acid (1.04 g corrected, 2.78 mmol, Preparation 18) in 9.36 mL of acetone is allowed to stir at 50° C. for 15 minutes. The hazy solution is treated with a small scoop of celite and filtered to clarify the solution followed by rinsing with acetone (1×2.08 mL the 1×1.04 mL). The clear filtrate is placed in a heating bath at 50° C., and treated with 634 mg (3.33 mmol) of p-toluenesulfonic acid monohydrate as a solution in 0.317 mL of water followed by a rinse with 0.317 mL of acetone (gas evolution observed). After stirring at gentle reflux for 4 hours, the reaction is removed from the heating bath and treated with 10.4 mL of acetone over 10 minutes. The clear, colorless solution is optionally seeded and a precipitate is observed to form over 30 min at which time another 10.4 mL of acetone is introduced over 20 minutes. The slurry is allowed to stir an additional 4 hours followed by filtration, washing with acetone (2×10 mL) and drying in vacuo at 45° C. for 14 hours to provide 995 mg (78% corrected for 3 wt % acetone) of the title compound as a white solid.

mp (DSC) 155° C.

$^1$H NMR (500 MHz, CD$_3$OD) δ 7.70 (d, 2H, J=7.5 Hz), 7.34 (d, 2H, J=8.5 Hz), 5.58-5.42 (m, 1H), 3.92 (q, 1H, J=7.0 Hz), 2.96 (dd, 1H, J=14, 8.0 Hz), 2.42-2.30 (m, 2H), 2.24 (s, 3H), 2.09 (t, 1H, J=3.0 Hz), 1.52 (d, 3H, J=7.5 Hz), 1.51-1.40 (m, 1H).

EXAMPLE 19

1R,2S,4R,5R,6R-2-(2'S-2'-Aminopropionyl)amino-4-fluorobicyclo[3.1.0]hexane-2,6-dicarboxylic acid

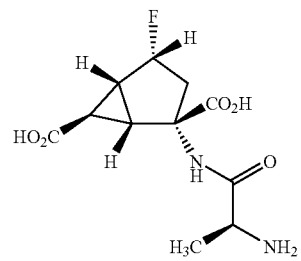

To solution of (1R,2S,4R,5R,6R)-2-(2'S-amino-propionyl)amino-4-fluorobicyclo[3.1.0]hexane-2,6-dicarboxylic acid mesylate (0.5 g, 1.35 mmol, Example 15) in 1 mL of water at 50° C. is added 5 mL of 3A ethanol followed after a few minutes by 0.27 mL (1.35 mmol) of 5 N aqueous sodium hydroxide. The heat is turned off and the clear colorless solution is diluted with 2.5 mL of ethanol, optionally seeded, and diluted further with 7.5 mL of ethanol over 30 min. The resulting slurry is allowed to stir thereafter with cooling to room temperature over 1 h and subsequently at room temperature for 2 hours. The solid is collected and washed with ethanol (1×10 mL) followed by drying in vacuo at 45° C. for 18.5 hours to afford 0.301 g (78% yield corrected for 1.6 wt % sodium methanesulfonate and 3 wt % ethanol) of the title compound as a white solid.

$^1$H NMR (500 MHz, D$_2$O) δ 5.45-5.30 (m, 1H), 3.88 (q, 1H, J=7.0 Hz), 2.58 (dd, 1H, J=14, 8.0 Hz), 2.33-2.30 (m, 1H), 2.27-2.26 (m, 1H), 1.92 (t, 1H, J=3.0 Hz), 1.36 (d, 3H, J=7.1 Hz), 1.41-1.32 (m, 1H).

$^{13}$C NMR (125 MHz, D$_2$O) δ 177.46, 176.92, 170.42, 94.56 and 93.19 (C—F splitting), 65.36, 49.01, 36.75 and 36.57 (C—F splitting), 33.61 and 33.55 (C—F splitting), 30.54 and 30.36 (C—F splitting), 20.27, 16.67.

EXAMPLE 20

(1R,2S,4R,5R,6R)-2-(2'S-Amino-propionyl)amino-4-fluorobicyclo[3.1.0]hexane-2,6-dicarboxylic disodium salt

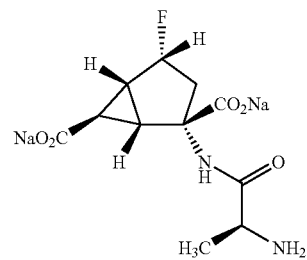

To a solution of (1R,2S,4R,5R,6R)-2-(2'S-amino-propionyl)amino-4-fluorobicyclo[3.1.0]hexane-2,6-dicarboxylic acid mesylate (70 mg, 0.19 mmol, Example 15) in 420 μL of methanol at 60° C. is added a warm solution of sodium acetate (46.5 mg, 0.57 mmol) in 470 μL of methanol with a rinse of 230 μL of methanol. The heat is turned off. The stirring hazy solution is diluted with 280 μL of methanol optionally followed by seeding to aid the crystallization. The resulting slurry is slowly cooled to ambient temperature over 1 hour and stirred for 2 hours at ambient temperature. The product is isolated by filtration, washed with methanol (2×280 μL), and dried in vacuo at 45° C. for 15 hours to furnish 52.5 mg (85% yield corrected for 2.3 wt % sodium methanesulfonate and 0.2 wt % methanol) of the title compound as a white solid.

$^1$H NMR (500 MHz, D$_2$O) δ 5.44-5.29 (m, 1H), 3.89 (q, 1H, J=7.0 Hz), 2.65 (s, 3H), 2.56 (dd, 1H, J=14, 8.0 Hz), 2.16-2.13 (m, 1H), 2.10-2.09 (m, 1H), 1.74 (t, 1H, J=3.1 Hz), 1.38 (d, 3H, J=7.1 Hz), 1.36-1.28 (m, 1H).

$^{13}$C NMR (125 MHz, D$_2$O) δ 180.00, 178.72, 170.13, 95.40 and 93.99 (C—F splitting), 65.97, 49.06, 37.25 and 37.07 (C—F splitting), 33.01 and 32.94 (C—F splitting), 29.64 and 29.46 (C—F splitting), 22.48, 16.68.

EXAMPLE 21

(1S,2S,4S,5R,6R)-2-(2'S-aminopropionyl)amino-4-hydroxy-bicyclo[3.1.0]hexane-2,6-dicarboxylic acid hydrochloride

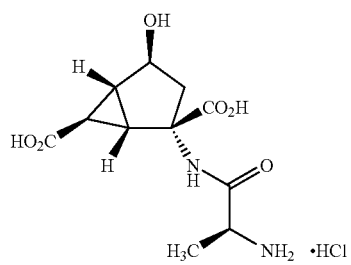

To a solution of (1S,2S,4S,5R,6R)-4-acetyloxy-2-[2'S-(tert-butoxy)carbonylaminopropionyl]-aminobicyclo[3.1.0]hexane-2,6-dicarboxylic acid diethyl ester (0.600 g, 1.28 mmol, Preparation 21) in THF (30 mL) and water (30 mL) is added lithium hydroxide monohydrate (0.535 g, 12.8 mmol). After stirring at room temperature for 3 hours, the reaction is diluted with water and washed with ethyl acetate (2×25 mL). The aqueous layer is acidified to pH 1 with aqueous 1N HCl solution and extracted with ethyl acetate (3×30 mL). The combined organic extracts are concentrated, redissolved in 1N HCl in ethyl acetate (60 mL), then stirred under nitrogen at room temperature for 16 hours. The solvent is removed in vacuo to afford 400 mg (99%) of the product as a white solid.

LCMS: m/z 273 [M+H]$^+$ @ R$_T$ 0.20 min.

$^1$H NMR (CD$_3$OD)*: 4.13 (1H, d, 5.9 Hz), 3.80 (1H, q, 6.7 Hz), 2.41-2.31 (2H, m), 1.93 (1H, dd, 6.0 Hz, 2.7 Hz), 1.62 (1H, dd, 5.9 Hz, 15.5 Hz), 1.44 (1H, t, 3.0 Hz), 1.38 (3H, d, 6.8 Hz); *N.B. Exchangeable protons not observed by NMR=6.

EXAMPLE 22

(1S,2S,4S,5R,6R)-2-(2'-Amino-acetylamino)-4-hydro-oxy-bicyclo[3.1.0]hexane-2,6-dicarboxylic acid hydrochloride

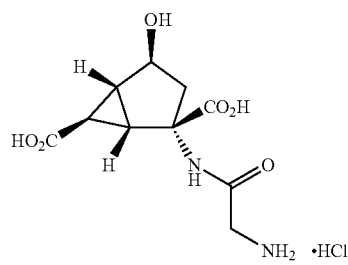

Prepare according to General Procedure C using (1S,2S, 4S,5R,6R)-2-(2'-tert-butoxycarbonylamino-acetylamino)-4-hydroxy-bicyclo[3.1.0]hexane-2,6-dicarboxylic acid diethyl ester (300 mg, 0.84 mmoles, Preparation 23), with the exception that the tert-butoxycarbonyl protecting group is removed by treating with 4M HCl in dioxane. Yield 156 mg (63%).

[α]$_D^{23}$=−36 (c=0.5, MeOH).

$^1$H NMR (400 MHz, CD$_3$OD) δ 1.56 (1H, t, J=2.9 Hz), 1.74 (1H, dd, J=5.8, 15.4 Hz), 2.12 (1H, m), 2.48 (1H, d, J=15.4 Hz), 2.61 (1H, m), 3.62 (2H, s), 4.32 (1H, d, J=5.49 Hz).

Anal Calcd for C$_{10}$H$_{14}$N$_2$O$_6$·1.3HCl·H$_2$O: C, 37.11; H, 5.39; N, 8.66. Found: C, 37.36; H, 4.99; N, 8.30.

MS (ES) m/z 258.8 [M+H]$^+$.

EXAMPLE 23

(1S,2S,4S,5R,6R)-2-(2'S-Amino-3'-methyl-butyrylamino)-4-hydroxybicyclo[3.1.0]-hexane-2,6-dicarboxylic acid hydrochloric acid

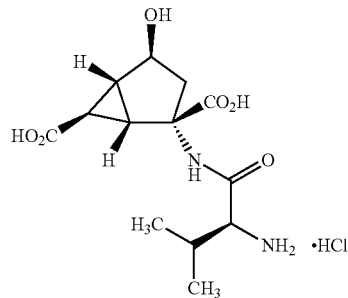

Prepare according to General Procedure C using (1S,2S, 4S,5R,6R)-2-(2'S-tert-butoxycarbonylamino-3'-methyl-butyrylamino)-4-hydroxy-bicyclo[3.1.0]hexane-2,6-dicarboxylic acid diethyl ester (480 mg, 1.19 mmoles, Preparation 24), with the exception that the tert-butoxycarbonyl protecting group is removed by treating with 4M HCl in dioxane. Yield 307 mg (76%).

[α]$_D^{23}$=+8.33 (c=0.48, MeOH).

$^1$H NMR (400 MHz, CD$_3$OD) δ 1.07 (3H, d, J=6.8 Hz), 0.11 (3H, d, J=7.3 Hz), 1.55 (1H, t, J=2.9 Hz), 1.76 (1H, dd, J=5.8, 15.6 Hz), 2.14 (1H, dd, J=3.4, 5.8 Hz), 2.24 (1H, m), 2.50 (1H, d, J=15.6 Hz), 2.64 (1H, dd, J=2.9, 5.8 Hz), 3.66 (1H, d, J=5.4 Hz), 4.32 (1H, d, J=5.8 Hz).

Anal Calcd for $C_{13}H_{20}N_2O_6 \cdot HCl \cdot 1.1H_2O$: C, 43.79; H, 6.56; N, 7.86. Found: C, 43.77; H, 6.20; N, 7.47.

HRMS calcd for $C_{13}H_{21}N_2O_6$, 301.1400. Found, 301.1400.

EXAMPLE 24

(1S,2S,4S,5R,6R)-2-(2'S-Amino-4'-methyl-pentanoylamino)-4-hydroxy-bicyclo[3.1.0]hexane-2,6-dicarboxylic acid hydrochloric acid

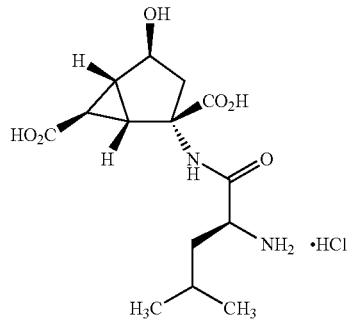

Prepare according to General Procedure C using (1S,2S,4S,5R,6R)-2-(2'S-tert-butoxycarbonylamino-4'-methyl-pentanoylamino)-4-hydroxy-bicyclo[3.1.0]hexane-2,6-dicarboxylic acid diethyl ester (460 mg, 1.11 mmoles, Preparation 25), with the exception that the tert-butoxycarbonyl protecting group is removed by treating with 4M HCl in dioxane. Yield 371 mg (95%).

$[\alpha]_D^{23}$=+4 (c=0.5, MeOH).

$^1$H NMR (400 MHz, CD$_3$OD) δ 1.01 (3H, d, J=5.8 Hz), 1.03 (3H, d, J=6.3 Hz), 1.54 (1H, t, J=2.9 Hz), 1.63-1.82 (4H, m), 2.14 (1H, dd, J=2.9, 5.8 Hz), 2.49 (1H, d, J=15.6 Hz), 2.62 (1H, dd, J=2.9, 5.8 Hz), 3.83-3.86 (1H, m), 4.32 (1H, d, J=5.8 Hz).

Anal Calcd for $C_{14}H_{22}N_2O_6 \cdot HCl \cdot 1.4H_2O$: C, 44.72; H, 6.92; N, 7.45. Found: C, 44.52; H, 6.57; N, 7.13.

HRMS calcd for $C_{14}H_{23}N_2O_6$, 315.1556. Found, 315.1569.

EXAMPLE 25

(1S,2S,4S,5R,6R)-2-(2'S-Amino-3'S-methyl-pentanoylamino)-4-hydroxy-bicyclo[3.1.0]hexane-2,6-dicarboxylic acid hydrochloric acid

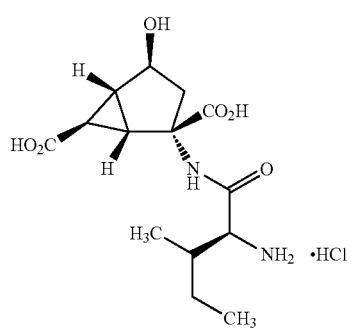

Prepare according to General Procedure C using (1S,2S,4S,5R,6R)-2-(2'S-tert-butoxycarbonylamino-3'S-methyl-pentanoylamino)-4-hydroxy-bicyclo[3.1.0]hexane-2,6-dicarboxylic acid diethyl ester (410 mg, 0.99 mmoles, Preparation 26), with the exception that the tert-butoxycarbonyl protecting group is removed by treating with 4M HCl in dioxane. Yield 330 mg (95%).

$[\alpha]_D^{23}$=+8 (c=0.5, MeOH).

$^1$H NMR (400 MHz, CD$_3$OD) δ 0.99 (3H, t, J=7.3 Hz), 1.08 (3H, t, J=7.3 Hz), 1.17-1.27 (1H, m), 1.53 (1H, t, J=2.9 Hz), 1.59-1.65 (1H, m), 1.76 (1H, dd, J=5.8, 15.6 Hz), 1.96-2.00 (1H, m), 2.14 (1H, dd, J=2.9, 5.8 Hz), 2.46 (1H, d, J=15.6 Hz), 2.66 (1H, dd, J=2.9, 5.8 Hz), 3.70 (1H, d, J=5.4 Hz), 4.31 (1H, d, J=5.8 Hz).

Anal Calcd for $C_{14}H_{22}N_2O_6 \cdot 1.1HCl \cdot 1.2H_2O$: C, 44.71; H, 6.83; N, 7.45. Found: C, 44.38; H, 6.51; N, 7.08.

HRMS calcd for $C_{14}H_{23}N_2O_6$, 315.1556. Found, 315.1566.

EXAMPLE 26

(1S,2S,4S,5R,6R)-2-[2'-(2-Amino-acetylamino)-acetylamino]-4-hydroxy-bicyclo[3.1.0]hexane-2,6-dicarboxylic acid

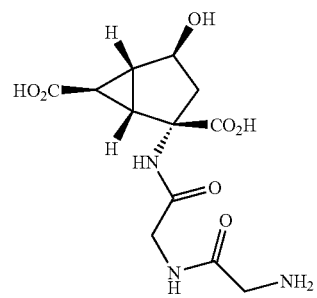

Treat (1S,2S,4S,5R,6R)-2-[2'-(2-tert-butoxycarbonylamino-acetylamino)-acetylamino]-4-hydroxy-bicyclo[3.1.0]hexane-2,6-dicarboxylic acid diethyl ester (360 mg, 0.77 mmoles, Preparation 27) with an excess of 4M HCl in dioxane and stir for 40 minutes; concentrated in vacuo. Add ethyl acetate and concentrated. Treat the solid with THF (3M) and 1N LiOH (3.0 equiv.). Stir for 1 hour then add 1N HCl until pH=3. Concentrated the reaction in vacuo. Purify via DOWEX® 50WX8-100 ion-exchange resin. Yield 188 mg (78%).

$[\alpha]_D^{23}$=+3.92 (c=0.51, H$_2$O).

$^1$H NMR 300 MHz, D$_2$O) δ 1.43 (1H, t, J=2.9 Hz), 1.53 (1H, dd, J=5.9, 15.4 Hz), 1.98 (1H, m), 2.23-2.31 (2H, m), 3.70 (2H, s), 3.82 (2H, app d, J=1.1 Hz), 4.16 (1H, d, J=5.9 Hz).

HRMS calcd for $C_{12}H_{18}N_3O_7$, 316.1145. Found, 316.1123.

EXAMPLE 27

(1S,2S,4S,5R,6R)-2-[2'-(2S-Amino-propionylamino)-acetylamino]-4-hydroxy-bicyclo[3.1.0]hexane-2,6-dicarboxylic acid

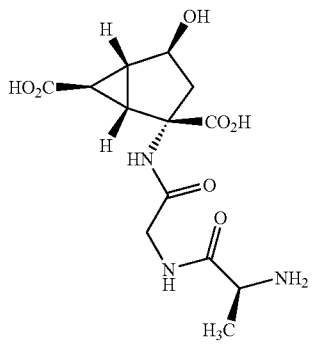

Prepare according to the general procedure outlined in Example 26 using (1S,2S,4S,5R,6R)-2-[2'-(2S-tert-butoxycarbonylamino-propionylamino)-acetylamino]-4-hydroxy-bicyclo[3.1.0]hexane-2,6-dicarboxylic acid diethyl ester (410 mg, 0.84 mmoles, Preparation 28). Yield 200 mg (72%).

$[\alpha]_D^{23}$=+23.53 (c=0.51, $H_2O$).

$^1$H NMR 300 MHz, $D_2O$) δ 1.36 (3H, d, J=7.0 Hz), 1.37 (1H, t, J=3.3 Hz), 1.49 (1H, dd, J=5.9, 15.4 Hz), 1.91 (1H, dd, J=2.9, 5.9 Hz), 2.15 (1H, dd, J=2.9, 5.9 Hz), 2.27 (1H, d, J=15.4 Hz), 3.79 (2H, s), 3.95 (1H, q, J=7.0 Hz), 4.13 (1H, d, J=5.5 Hz).

HRMS calcd for $C_{13}H_{19}N_3O_7$, 330.1301. Found, 330.1290.

EXAMPLE 28

(1S,2S,4S,5R,6R)-2-(2'S-Amino-3'-phenyl-propionylamino)-4-hydroxy-bicyclo[3.1.0]hexane-2,6-dicarboxylic acid hydrochloride

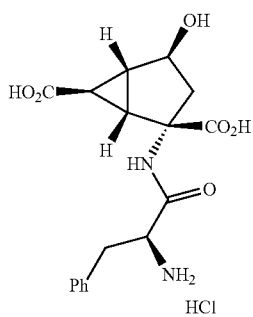

Prepare according to General Procedure C using (1S,2S,4S,5R,6R)-2-(2'-tert-butoxycarbonylamino-3'-phenyl-propionylamino)-4-hydroxy-bicyclo[3.1.0]hexane-2,6-dicarboxylic acid diethyl ester (400 mg, 0.89 mmoles, Preparation 29). Yield 290 mg (85%).

$[\alpha]_D^{23}$=+3.64 (c=0.55, MeOH).

$^1$H NMR (400 MHz, $CD_3OD$) δ 1.45 (1H, t, J=3.3 Hz), 1.60 (1H, dd, J=5.5, 15.4 Hz), 2.03 (1H, dd, J=2.6, 5.9 Hz), 2.37 (1H, d, J=15.4 Hz), 2.55 (1H, dd, J=2.9, 5.9 Hz), 2.90 (1H, dd, J=8.4, 14.3 Hz), 3.22 (1H, dd, J=5.1, 14.7 Hz), 3.97 (1H, dd, J=5.5, 8.8 Hz), 4.21 (1H, d, J=5.5 Hz), 7.19-7.31 (5H, m).

HRMS calcd for $C_{17}H_{21}N_2O_6$, 349.1400. Found, 349.1388.

Anal. Calcd for $C_{17}H_{21}N_2O_6 \cdot HCl \cdot H_2O$: C, 50.69; H, 5.76; N, 6.95; Cl, 8.80. Found: C, 50.66; H, 5.65; N, 6.85; Cl, 8.20.

MS found 349.0 $[M+H]^+$.

EXAMPLE 29

(1S,2S,4S,5R,6R)-2-(2'S-Amino-4'-carbamoyl-butyrylamino)-4-hydroxy-bicyclo[3.1.0]hexane-2,6-dicarboxylic acid hydrochloride

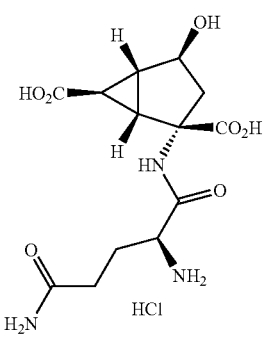

Prepare the title compound by dissolving (1S,2S,4S,5R,6R)-2-[2'-tert-butoxycarbonylamino-4'-(trityl-carbamoyl)-butyrylamino]-4-hydroxy-bicyclo[3.1.0]hexane-2,6-dicarboxylic acid diethyl ester (1.18 mmoles, Preparation 30) in THF (10 mL) and treating the solution with 2.5 N LiOH (12 mL). Allow the solution to stir 3 hours and then adjust to pH=2 with 2.5 N HCl. Extract the product four times with ethyl acetate, dry over anhydrous sodium sulfate and concentrate in-vacuo to give a white powder. Dissolve the di-acid product (0.74 mmol) in 1,2-dichloroethane (3.7 mL) and treat with anisole (0.3 mL) and trifluoroacetic acid (3.72 mL). Stir the reaction mixture at 23° C. for 2.5 hours and then concentrate in vacuo to give a brown oil. Dissolve the brown oil in water, extract five times with dichloromethane, concentrate the aqueous layer in-vacuo, treat with 1 N HCl (0.74 mL), and lyophilize. Treat the solid with another portion of 1 N HCl (2 mL) and lyophilize again to afford 446 mg (quant) of the title compound.

$[\alpha]_D^{23}$=+8.16 (c=0.49, MeOH).

$^1$H NMR (400 MHz, $CD_3OD$) δ 1.60 (1H, t, J=3.3 Hz), 1.79 (1H, dd, J=5.5, 15.4 Hz), 2.10-2.17 (3H, m), 2.46-2.55 (3H, m), 2.60 (1H, dd, J=2.9, 5.9 Hz), 3.94 (1H, t, J=6.2 Hz), 4.33 (1H, d, J=5.5 Hz).

MS found 330.0 $[M+H]^+$, 351.9 $[M+Na]^+$.

HRMS calcd for $C_{13}H_{19}N_3O_7$, 330.1301. Found, 330.1295.

EXAMPLE 30

(1S,2S,4S,5R,6R)-2-(2'S,6'-Diamino-hexanoylamino)-4-hydroxy-bicyclo[3.1.0]hexane-2,6-dicarboxylic acid bis hydrochloride

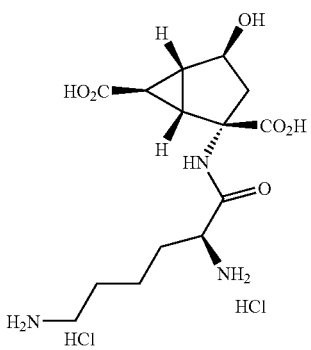

Prepare according to General Procedure C using (1S,2S,4S,5R,6R)-2-(2'S,6'-bis-tert-butoxycarbonylamino-hexanoylamino)-4-hydroxy-bicyclo[3.1.0]hexane-2,6-dicarboxylic acid diethyl ester (Preparation 31).

$^1$H NMR (400 MHz, CD$_3$OD) δ 1.47-1.59 (3H, m), 1.66-1.78 (2H, m), 1.84 (1H, dd, J=5.4, 15.2 Hz), 1.91 (2H, m), 2.16 (1H, dd, J=3.4, 5.7 Hz), 2.45 (1H, d, J=15.7 Hz), 2.66 (1H, dd, J=2.9, 5.9 Hz), 2.97 (2H t, J=7.3 Hz), 3.92 (1H, t, J=6.4 Hz), 4.33 (1H, d, J=5.4 Hz).

MS found 330.0 [M+H]$^+$.

EXAMPLE 31

(1S,2S,4S,5R,6R)-2-(2'S-Amino-3'-carbamoyl-propionylamino)-4-hydroxy-bicyclo[3.1.0]hexane-2,6-dicarboxylic acid

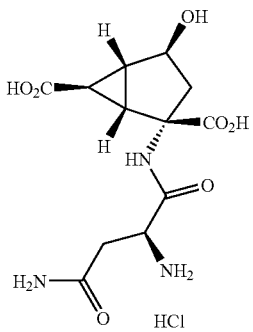

Prepare the title compound by dissolving (1S,2S,4S,5R,6R)-2-[2'-tert-butoxycarbonylamino-3'-(trityl-carbamoyl)-propionylamino]-4-hydroxy-bicyclo[3.1.0]hexane-2,6-dicarboxylic acid diethyl ester (1.07 mmoles, Preparation 32) in THF (12 mL) and treating the solution with 2.5 N LiOH (12 mL). Allow the solution to stir 3 hours and adjust to pH=2 with 2.5 N HCl. Extract the product four times with ethyl acetate, dry over anhydrous sodium sulfate and concentrate in-vacuo to give a white powder. Dissolve the di-acid product (1.22 mmol) in 1,2-dichloroethane (6 mL) and treat with anisole (1 mL) and trifluoroacetic acid (6 mL). Allow the reaction mixture to stir at 23° C. for 10 hours then concentrate in-vacuo to give a brown oil. Dilute the brown oil with diethyl ether and the product crystallized out as a white solid. Filter and wash with copious portions of ether. Dissolve the solid in a minimal amount of water, treat with 0.5 N HCl (5 mL), and lyophilize 3 times to afford 386 mg (90%) of the title compound.

[α]$_D^{23}$=0 (c=0.5, MeOH).

$^1$H NMR (400 MHz, CD$_3$OD) δ 1.59 (1H, t, 3.4 Hz), 1.76 (1H, dd, J=5.9, 16.1 Hz), 2.11 (1H, dd, J=2.9, 5.9 Hz), 2.53 (1H, d, J=16.1 Hz), 2.55 (1H, dd, J=2.9, 5.9 Hz), 2.74 (1H, dd, J=9.8, 17.1 Hz), 2.95 (1H, dd, J=3.9, 17.1 Hz), 4.19 (1H, dd, J=3.9, 9.8 Hz), 4.32 (1H, d, J=5.9 Hz).

MS found 316.0 [M+H]$^+$, 337.9 [M+Na]$^+$.

HRMS calcd for C$_{12}$H$_{16}$N$_3$O$_7$Na, 338.0964. Found, 338.0953.

EXAMPLE 32

(1S,2S,4S,5R,6R)-2-[2'S-Amino-3'-(1H-indol-3-yl)-propionylamino]-4-hydroxy-bicyclo[3.1.0]hexane-2,6-dicarboxylic acid

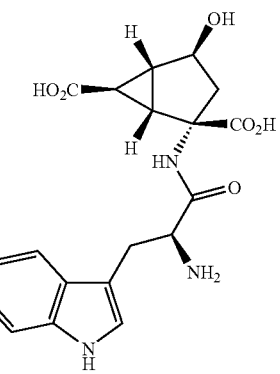

Prepare by dissolving 2-[2'-tert-butoxycarbonylamino-3'-(1'-tert-butoxycarbonyl-1H-indol-3'-yl)-propionylamino]-4-hydroxy-bicyclo[3.1.0]hexane-2,6-dicarboxylic acid diethyl ester (0.93 mmoles, Preparation 33) in THF (11 mL) and treating the solution with 2.5 N LiOH (11 mL). Allow the solution to stir 3 h and then adjust to pH=2 with 2.5 N HCl. Extract the product four times with ethyl acetate, dry over anhydrous sodium sulfate and concentrate in-vacuo to give a white powder. Dissolve the di-acid product (0.78 mmol) in a solution of 4M HCl in dioxane (20 mL) and allow the reaction mixture to stir for 3 hours at 23° C. Concentrate the reaction mixture, dilute with dichloromethane, and concentrate again in-vacuo. Dissolve the crude product in methanol, apply to a radial chromatography (silica gel) plate, allowed to spin dry, and elute with MeOH (10%)/NH$_4$OH (1%)/CHCl$_3$ to MeOH (60%)/NH$_4$OH (2%)/CHCl$_3$. Dissolve the product in water and lyophilize two times to afford 139 mg (46%) of the title compound.

[α]$_D^{23}$=+19.23 (c=0.52, MeOH).

$^1$H NMR (400 MHz, CD$_3$OD) δ 1.43 (1H, t, J=2.9 Hz), 1.57 (1H, dd, J=5.9, 15.2 Hz), 2.05 (1H, dd, J=3.4, 6.4 Hz), 2.41 (1H, d, J=14.7 Hz), 2.46 (1H, dd, J=2.4, 5.9 Hz), 3.15 (1H, dd, J=5.4, 14.7 Hz), 3.49 (1H, dd, J=5.4, 14.7 Hz), 4.05 (1H, dd, J=5.4, 9.3 Hz), 4.17 (1H, d, J=5.4 Hz), 7.09 (2H, m), 7.27 (1H, s), 7.37 (1H, d, J=8.3 Hz), 7.75 (1H, d, J=7.8 Hz).

MS found 388.0 [M+H]$^+$, 409.9 [M+Na]$^+$.

HRMS calcd for C$_{19}$H$_{21}$N$_3$O$_6$, 388.1508. Found, 388.1502.

EXAMPLE 33

(1S,2S,4S,5R,6R)-4-hydroxy-2-[(pyrrolidine-2'S-carbonyl)-amino]-bicyclo[3.1.0]hexane-2,6-dicarboxylic acid hydrochloride salt

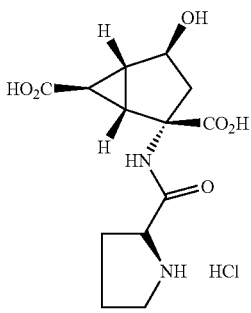

Prepare according to General Procedure C using (1S,2S,4S,5R,6R)-2-(1'-tert-butoxycarbonyl-pyrrolidine-2'S-carbonyl)-4-hydroxy-bicyclo[3.1.0]hexane-2,6-dicarboxylic acid diethyl ester (Preparation 34), with the exception that the tert-butoxycarbonyl protecting group is removed by treating with 4M HCl in dioxane.

$[\alpha]_D^{23}$=-40 (c=0.5, MeOH).

$^1$H NMR (400 MHz, CD$_3$OD) δ 1.59 (1H t, J=3 Hz), 1.78 (1H, dd, J=5.9, 15.3 Hz), 2.06 (4H, m), 2.42 (1H, m), 2.59 (2H, m), 3.35 (m, 3H), 4.27 (1H, m), 4.32 (1H, d, J=5.9 Hz).

HRMS calcd for C$_{13}$H$_{19}$N$_2$O$_6$, 299.1243. Found, 299.1242.

Anal. Calcd for C$_{13}$H$_{18}$N$_2$O$_6$.HCl.H$_2$O: C, 44.26; H, 6.00; N, 7.94. Found: C, 44.13; H, 5.78; N, 7.62.

EXAMPLE 34

(1S,2S,4S,5R,6R)-2-[2'S-Amino-3'-(4-hydroxy-phenyl)-propionylamino]-4-hydroxy-bicyclo[3.1.0]hexane-2,6-dicarboxylic acid hydrochloride salt

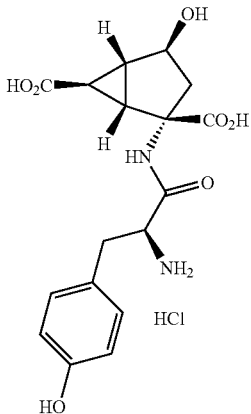

Prepare according to General Procedure C using (1S,2S,4S,5R,6R)-2-[2'S-tert-Butoxycarbonylamino-3'-(4-tert-butoxycarbonyloxy-phenyl)-propionylamino]-4-hydroxy-bicyclo[3.1.0]hexane-2,6-dicarboxylic acid diethyl ester (Preparation 35), with the exception that the tert-butoxycarbonyl protecting group was removed by treating with 4M HCl in dioxane. Yield 199 mg (50%).

$[\alpha]_D^{23}$=+8 (c=0.5, MeOH).

$^1$H NMR (400 MHz, CD$_3$OD) δ 1.48 (1H, t, J=3 Hz), 1.62 (1H, dd, J=5.9, 15.3 Hz), 2.03 (1H, m), 2.38 (1H, d, J=15.3 Hz), 2.55 (1H, m), 2.8 (1H, dd, J=8.9, 14.4 Hz), 3.12 (1H, dd, J=5.4, 14.4 Hz), 3.90 (1H, q, J=5.4 Hz), 4.21 (1H, d, J=5.9 Hz), 6.7 (2H, d, J=8.4 Hz), 7.05 (2H, d, J=8.4 Hz).

HRMS calcd for C$_{17}$H$_{21}$N$_2$O$_7$, 365.1349. Found, 365.1374.

Anal. Calcd for C$_{17}$H$_{20}$N$_2$O$_7$.1.1HCl.1.1H$_2$O: C, 48.12; H, 5.54; N, 6.60. Found: C, 47.89; H, 5.37; N, 6.50.

EXAMPLE 35

(1S,2S,4S,5R,6R)-2-(2'S-Amino-4'-methylsulfanyl-butyrylamino)-4-hydroxy-bicyclo[3.1.0]hexane-2,6-dicarboxylic acid bis ammonium salt

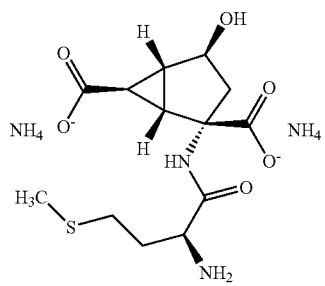

Prepare according to General Procedure C using (1S,2S,4S,5R,6R)-2-(2'S-tert-Butoxycarbonylamino-4'-methylsulfanyl-butyrylamino)-4-hydroxy-bicyclo[3.1.0]hexane-2,6-dicarboxylic acid diethyl ester (Preparation 36), with the exception that the tert-butoxycarbonyl protecting group was removed by treating with 4M HCl in dioxane. The final compound was loaded with MeOH on to a 2 mm Chromatotron plate and eluted with 50/49.5/0.5 CHCl$_3$/MeOH/NH$_4$OH. The amount of NH$_4$OH was increased to 1% over the course of the elution to give the zwitterionic compound. Yield 136 mg (37%).

$[\alpha]_D^{23}$=+28 (c=1.0, MeOH).

$^1$H NMR (400 MHz, CD$_3$OD) δ 1.63 (1H, dd, J=6.0, 15.6 Hz), 2.03 (2H, m), 2.12 (3H, s), 2.18 (1H, m), 2.35 (1H, m), 2.49 (1H, d, J=15.6 Hz), 2.65 (2H, t, J=8.4 Hz), 3.84 (1H, t, J=6.0 Hz), 4.19 (1H, d, J=6.0 Hz). HRMS calcd for C$_{13}$H$_{21}$N$_2$O$_6$S, 333.1120. Found, 333.1105.

EXAMPLE 36

(1S,2S,4S,5R,6R)-2-[2'S-(2S-Amino-propionylamino)-propionylamino]-4-hydroxy-bicyclo[3.1.0.]hexane)-2,6-dicarboxylic acid

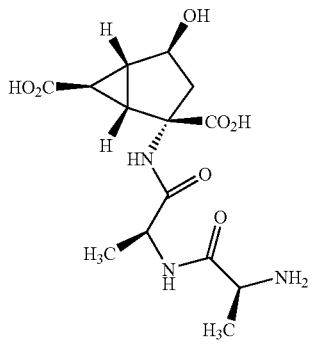

Stir (1S,2S,4S,5R,6R)-2-[2'S-(2S-tert-butoxycarbonylamino-propionylamino) propionylamino]-4-hydroxy-bicyclo[3.1.0.]hexane-2,6-dicarboxylic acid diethyl ester (0.045 g, 0.1 mmol, Preparation 39) in 1 ml of 4N HCl in dioxane for 40 min then concentrate the reaction in vacuo. Stir the crude material in THF (5 ml) and 0.5N LiOH (0.35 mmol) for 1 hour. Adjust the pH=2 with 0.5 N HCl and concentrate the reaction. Purify the crude product using cation exchange chromatography (Dowex® 50X8-100; elute with 10% pyridine/H$_2$O) to yield 19 mg (55.3%) of the title compound.

$^1$H NMR (300 MHz, D$_2$O) δ 1.23 (3H, d, J=7.3 Hz), 1.36 (3H, d, J=7.3 Hz), 1.40-145 (1H, m), 1.50 (1H, dd, J=5.5, 15.4 Hz), 1.90-1.96 (1H, m), 2.20 (1H, dd, J=2.6, 5.9 Hz), 2.29 (1H, d, J=15.4 Hz), 3.90 (1H, q, J=7.3 Hz), 4.15-4.22 (2H, m).
MS (ES) m/z 342.1 [M−1]$^-$.
HRMS calcd for C$_{14}$H$_{22}$N$_3$O$_7$, 344.1458. Found, 344.1457.

EXAMPLE 37

(1S,2S,4S,5R,6R)-2-[2'S-(2-Amino-acetylamino)-propionylamino]-4-hydroxy-bicyclo[3.1.0.]hexane-2,6-dicarboxylic acid

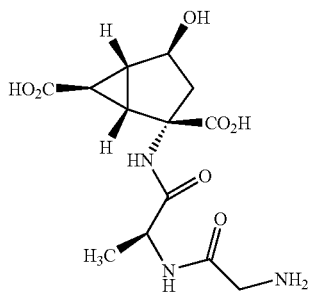

(1S,2S,4S,5R,6R)-2-[2'S-(2-tert-butoxycarbonylamino-acetylamino)-propionylamino]-4-hydroxy-bicyclo[3.1.0.]hexane-2,6-dicarboxylic acid diethyl ester (0.12 g, 0.25 mmol, Preparation 40) in THF (5 ml) and 1N LiOH (1.0 mmol) for 1 hour. Adjust the mixture to pH=2 using 1N HCl and concentrate. Stir the crude material in a saturated HCl (g) ethyl acetate solution at 0° C. Remove excess HCl (g) by purging with N$_2$ and concentrate the reaction. Purify the crude product using cation exchange chromatography (Dowex® 50X8-100; elute with 10% pyridine/H$_2$O) to yield 0.06 g (72.9%) of the title compound.

[α]$_D^{23}$=−42.11 (c=0.57, H$_2$O).

$^1$H NMR (300 MHz, D$_2$O) δ 1.21 (3H, d, J=7.3 Hz), 1.39 (1H, m), 1.50 (1H, dd, J=5.7, 15.8 Hz), 1.91 (1H, m), 2.15 (1H, dd, J=2.6, 5.9 Hz), 2.28 (1H, d, J=15.0 Hz), 3.65 (2H, s), 4.14 (1H, app d, J=5.9 Hz), 4.20 (1H, app q, J=7.3 Hz).

HRMS calcd for C$_{13}$H$_{20}$N$_3$O$_7$, 330.1301. Found, 330.1299.

EXAMPLE 38

(1S,2S,4S,5R,6R)-2-[2'S-(2S-Amino-4-methyl-pentanoylamino)-propionylamino]-4-hydroxy-bicyclo[3.1.0]hexane-2,6-dicarboxylic acid

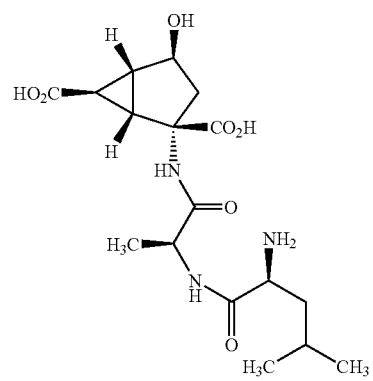

Prepare according to General Procedure C using (1S,2S,4S,5R,6R)-2-[2'-(2S-tert-butoxycarbonylamino-4-methyl-pentanoylamino)-propionylamino]-4-hydroxy-bicyclo[3.1.0]hexane-2,6-dicarboxylic acid diethyl ester (Preparation 41). Yield 0.21 g (57%, 0.50 mmoles) of a white solid.

[α]$_D^{23}$=−3.64° (c=0.55, MeOH).

$^1$H NMR (300 MHz, CD$_3$OD) δ 0.89 (3H, d, J=4.4 Hz), 0.91 (3H, d, J=4.0 Hz), 1.29 (3H, d, J=7.0 Hz), 1.52 (1H, t, J=3.3 Hz), 1.55-1.67 (4H, m), 1.97 (1H, dd, J=2.9, 5.9 Hz), 2.38 (1H, dd, J=2.9, 5.9 Hz), 2.45 (1H, d, J=15.4 Hz), 3.75-3.80 (1H, m), 4.18 (1H, d, J=5.9 Hz), 4.33 (1H, app. q, J=7.0 Hz), Anal Calcd for C$_{17}$H$_{27}$N$_3$O$_7$.1.0HCl.1.6H$_2$O: C, 45.30; H, 6.98; N, 9.32; Cl, 7.87. Found: C, 44.95; H, 6.54; N, 9.12; Cl, 7.53.

HRMS (ES) calcd for C$_{17}$H$_{28}$N$_3$O$_7$ [M+H]$^+$, 386.1927. Found, 386.1911.

EXAMPLE 39

(1S,2S,4S,5R,6R)-2-[2'S-(2-Amino-3-methyl-butyrylamino)-propionylamino]-4-hydroxy-bicyclo[3.1.0]hexane-2,6-dicarboxylic acid

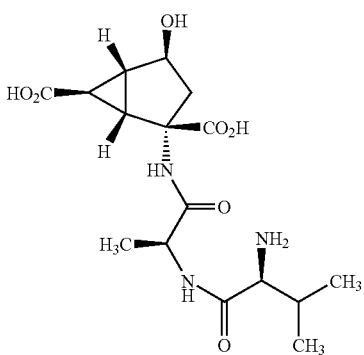

Prepare according to General Procedure C using (1S,2S, 4S,5R,6R)-2-[2'-(2S-tert-Butoxycarbonylamino-3-methyl-butyrylamino)-propionylamino]-4-hydroxy-bicyclo[3.1.0]hexane-2,6-dicarboxylic acid diethyl ester (Preparation 42). Yield 0.15 g (88%, 0.37 mmoles) of a white solid.

$[\alpha]_D^{23}$=−15.69° (c=0.51, MeOH).

$^1$H NMR (300 MHz, CD$_3$OD) δ 0.92 (3H, d, J=7.0 Hz), 0.95 (3H, d, J=7.0 Hz), 1.28 (3H, d, J=7.0 Hz), 1.52 (1H, t, J=2.9 Hz), 1.60 (1H, dd, J=5.9, 15.4 Hz), 1.98 (1H, dd, J=3.3, 5.9 Hz), 2.03-2.15 (1H, m), 2.39 (1H, dd, J=2.9, 6.2 Hz), 2.45 (1H, d, J=15.4 Hz), 3.56 (1H, d, J=5.5 Hz), 4.18 (1H, d, J=5.9 Hz), 4.33 (1H, app. q, J=7.0 Hz), 8.82 (1H, s).

Anal Calcd for C$_{16}$H$_{25}$N$_3$O$_7$·1.0HCl·1.5H$_2$O: C, 44.19; H, 6.72; N, 9.66; Cl, 8.15. Found: C, 44.32; H, 6.48; N, 9.14; Cl, 7.66.

HRMS (ES) calcd for C$_{16}$H$_{26}$N$_3$O$_7$ [M+H]$^+$, 372.1771. Found, 372.1758.

EXAMPLE 40

(1R,2S,4R,5R,6R)-2-(2'S-2'-Aminopropionyl)amino-4-fluoro-bicyclo[3.1.0]hexane-2,6-dicarboxylic acid mesylate monohydrate

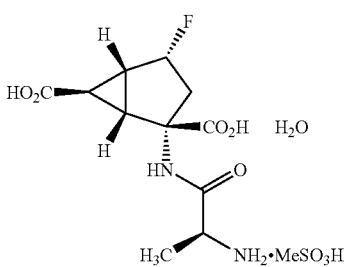

Add 16 mL of water followed by 11.4 mL (175 mmol) of methanesulfonic acid to a hazy solution of (1R;2S,4R,5R, 6R)-2-(2'S-2'-(tert-butoxycarbonylamino)propionyl)amino-4-fluoro-bicyclo[3.1.0]hexane-2,6-dicarboxylic acid (32.8 g, 87.5 mmol, Preparation 52) in 295 mL of acetone at gentle reflux dropwise to give a clear, faint yellow solution which yields a slurry after 5 minutes. Stir for 130 minutes, remove the heat source, and add another 295 mL of acetone over 30 minutes. Cool the slurry to room temperature, then stir an additional 2 hours. Filter the slurry, wash with acetone (2×82 mL), and vacuum dry at 45° C. for 16 hours to give 31.5 g (93%) of the title compound as a white solid.

The material may be further recrystallized. Mix 30.5 g of the above crude product with 152.5 mL of acetone and 35 mL of water. Heat to 55° C., and add water (3.66 mL) to effect complete dissolution. Dilute the solution with 61 mL of acetone and optionally seed. Remove the heat source and allow the mixture to gradually cool until good nucleation had commenced. Add 396 mL of acetone to the slurry over 70 minutes, then stir at room temperature for an additional 3 hours. Filter, wash with acetone (3×91 mL), and vacuum dry at 45° C. several hours (typically overnight) to yield 27.7 g (91% recovery) of the title compound as a white solid.

mp (DSC) 200° C.

$[\alpha]^{25}{}_D$ +34° (c 1.0, CH$_3$OH)

400 MHz $^1$H NMR (DMSO-d$_6$) δ 12.76 (br s, 2H), 9.18 (s 1H), 8.07 (br s, 3H), 5.50-5.36 (m, 1H), 3.87 (d, 1H, J=6.8 Hz), 2.82 (dd, 1H, J=14, 8.0 Hz), 2.38 (s, 3H), 2.25 (m, 2H), 1.96 (t, 1H, J=3.0 Hz), 1.39 (m, 1H), 1.37 (d, 3H, J=6.8 Hz).

100 MHz $^{13}$C NMR (DMSO-d$_6$) δ 173.1, 172.3, 169.7, 92.8 (d, C—F splitting), 63.2 (d, C—F splitting), 48.0, 39.7, 36.4 (d, C—F splitting), 32.5 (d, C—F splitting), 29.3 (d, C—F splitting), 19.3 (d, C—F splitting), 16.9.

FTIR (KBr) 3461 (w), 3379 (w), 3269 (m), 2653 (s), 2591 (s), 2529 (s), 1724 (s), 1691 (s), 1353 (m), 1287 (s), 1271 (s), 1256 (s), 1212 (s), 1147 (s), 1052 (s), 1024 (s), 787 (m) cm$^{-1}$.

Anal. Calcd for C$_{12}$H$_{21}$FN$_2$O$_9$S: C, 37.11; H, 5.45; N, 7.21. Found: C, 37.12; H, 5.45; N, 7.16.

EXAMPLE 41

(1R,4S,5S,6S)-4-(2'S-4'-methylthio-2'-aminobutanonyl)amino-2,2-dioxo-2λ$^6$-thia-bicyclo[3.1.0]hexane-4,6-dicarboxylic acid monohydrate

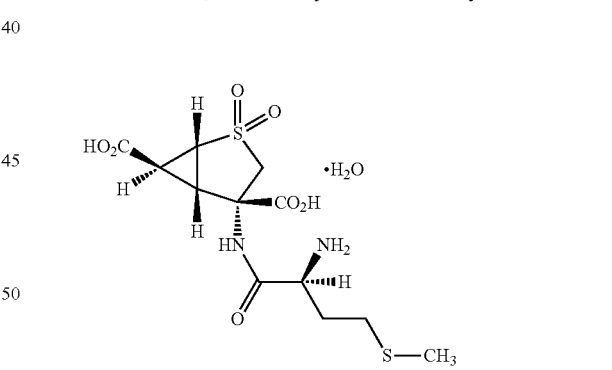

Heat a slurry of (1R,4S,5S,6S)-4-(2'S-4'-methylthio-2'-(tert-butoxycarbonyl)aminobutanonyl)amino-2,2-dioxo-2λ$^6$-thia-bicyclo[3.1.0]hexane-4,6-dicarboxylic acid monosodium salt (110.04 g, 225.3 mmol, Preparation 55) in acetone (110 mL) and water (550 mL) to 55° C. Add concentrated hydrochloric acid (56 mL, 675.8 mmol) dropwise to the stirring slurry to gradually afford dissolution. Upon completion of the addition, stir the solution at 55° C. for 2 hours. Remove the heat source and allow the solution to cool to room temperature. Filter the solution and rinse with 20 mL of water. Slowly add 2N sodium hydroxide (165 mL, 330 mmol) to the solution to raise pH to 1.71 at which time precipitation occurs. Stir for 10 minutes; a thin slurry forms and the pH drops to 0.98. Add more 2N sodium hydroxide (62 mL, 124 mmol) to the resultant slurry to raise the pH to 3.06 followed by stirring for 3 hours giving a final pH of 3.24. Filter the slurry, wash with water (2×165 mL), and dry at 45° C. for 15 hours to afford 73.27 g (85% weight yield) of the title compound as a white solid.

mp (DSC) 203° C.

$[\alpha]^{25}_D$ +13.4 (c 1.19, 1N HCl).

500 MHz $^1$H NMR (D$_2$O) δ 3.99 (t, 1H, J=6.0 Hz), 3.93 (d, 1H, J=15.0 Hz), 3.50 (dd, 1H, J=1.0, 4.0 Hz), 3.12 (d, 1H, J=15.0 Hz), 2.95 (dd, 1H, J=4.0, 7.0 Hz), 2.48 (t, 2H, J=8.0 Hz), 2.33 (t, 1H, J=4.0), 2.09-1.98 (m, 5H).

$^{13}$C NMR (125 MHz, D$_2$O) δ 173.50, 172.60, 169.18, 61.66, 54.76, 52.19, 42.55, 31.70, 30.10, 28.09, 23.53, 14.14.

FTIR (ATR) 3558.54 (s), 3024.05 (s), 2959.87 (s), 1748.83 (s), 1692.89 (s), 1681.99 (s), 1617.50 (s), 1567.63 (s), 1497.65 (s), 1314.11 (s), 1282.22 (s), 1263.26 (s), 1239.01 (s), 1101.46 (s), 884.62 (s), 809.95 (s), 773.46 (s) cm$^{-1}$.

Anal. Calcd for C$_{12}$H$_{18}$N$_2$O$_7$S$_2$.H$_2$O: C, 37.49; H, 5.24; N, 7.29. Found: C, 37.34; H, 5.04; N, 7.15.

EXAMPLE 42

(1R,4S,5S,6S)-4-(2'S-4'-methylthio-2'-aminobutanonyl)amino-2,2-dioxo-2λ$^6$-thia-bicyclo[3.1.0]hexane-4,6-dicarboxylic acid tosylate

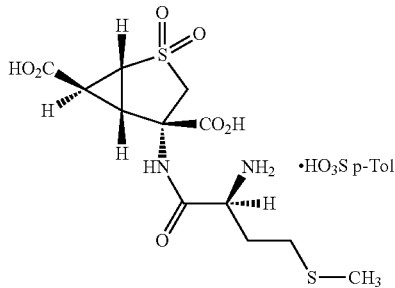

Heat a mixture of (1R,4S,5S,6S)-4-(2'S-4'-methylthio-2'-(tert-butoxycarbonyl)aminobutanonyl)amino-2,2-dioxo-2λ$^6$-thia-bicyclo[3.1.0]hexane-4,6-dicarboxylic acid (118.09 g corrected, 253 mmol, Preparation 56) and p-toluenesulfonic acid monohydrate (54 g, 278 mmol) in toluene (1180 mL) to 75° C., which results in a thick slurry. Stir the slurry at reflux for 165 minutes. Remove the heat source and allow the slurry to cool to room temperature followed by stirring overnight. Filter the slurry, wash with toluene (3×240 mL), and dry in vacuo at 45° C. for 22 hours to provide 134.92 g (98% yield) of the title compound.

mp (DSC) 255° C.

$[\alpha]^{25}_D$ +8.3 (c 1.2, CH$_3$OH).

500 MHz $^1$H NMR (CD$_3$OD) δ7.71 (d, 2H, J=8.0 Hz), 7.24 (d, 2H, J=8.0 Hz), 4.14 (d, 1H, J=15 Hz), 4.00 (t, 1H, J=6.0 Hz), 3.54 (dd, 3H, J=4.0, 7.0 Hz), 3.13 (d, 1H, J=15 Hz), 3.01 (dd, 1H, J=4.0, 7.0 Hz), 2.60 (t, 2H, J=8.0 Hz), 2.49 (t, 1H, J=4.0 Hz), 2.37 (s, 3H), 2.19-2.12 (m, 5H).

$^{13}$C NMR (125 MHz, CD$_3$OD) δ 170.49, 169.69, 168.99, 142.18, 140.67, 182.73, 125.79, 60.26, 54.76, 52.21, 42.44, 30.90, 30.77, 27.20, 22.33, 20.17, 13.96.

FTIR (ATR) 3091.19 (w), 1730.91 (s), 1668.22 (s), 1563.97 (s), 1518.49 (s), 1312.69 (m), 1247.46 (s), 1212.05 (s), 1156.33 (s), 1123.09 (s), 1035.95 (s), 1011.36 (s), 892.41 (s), 814.02 (s), 683.69 (s) cm$^{-1}$.

EXAMPLE 43

(1R,4S,5S,6S)-4-(2'S-4'-methylthio-2'-aminobutanonyl)amino-2,2-dioxo-2λ$^6$-thia-bicyclo[3.1.0]hexane-4,6-dicarboxylic acid mesylate

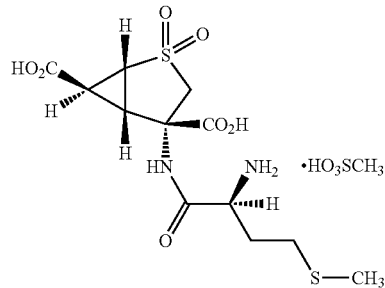

Heat a slurry of (1R,4S,5S,6S)-4-(2'S-4'-methylthio-2'-(tert-butoxycarbonyl)aminobutanonyl)amino-2,2-dioxo-2λ$^6$-thia-bicyclo[3.1.0]hexane-4,6-dicarboxylic acid (1.08 g, 2.31 mmol, Preparation 56) in 13 mL of propionitrile to 85° C. Add water (540 µL) to the slurry, then add methanesulfonic acid dropwise (225 µL, 3.47 mmol) Stir the slurry for 90 minutes. Remove the heat source and add propionitrile (30 mL). Cool the slurry to room temperature and stir for 90 minutes. Filter, wash with propionitrile (3×2.7 mL), and dry at 45° C. overnight to give 1.04 g (97%) of the title compound.

mp (DSC) 244° C.

$[\alpha]^{25}_D$ +10.2 (c 1.16, CH$_3$OH).

500 MHz $^1$H NMR (CD$_3$OD) δ 4.16 (d, 1H, J=15 Hz), 4.00 (t, 1H, J=6.0 Hz), 3.54 (dd, 1H, J=4.0, 7.0 Hz), 3.15 (d, 1H, J=15 Hz), 3.01 (dd, 1H, J=4.0, 7.0 Hz), 2.71 (s, 3H), 2.61 (t, 2H, J=8.0), 2.51 (t, 1H, J=4.0), 2.20-2.14 (m, 5H).

$^{13}$C NMR (125 MHz, CD$_3$OD) δ 170.50, 169.71, 169.00, 60.27, 54.78, 52.18, 42.43, 38.35, 30.90, 30.78, 28.20, 22.35, 13.96.

FTIR (ATR) 3055.57 (m), 1725.90 (s), 1693.60 (s), 1527.33 (s), 1528.96 (s), 1320.89 (s), 1176.86 (s), 1152.70 (s), 1118.55 (s), 1051.42 (s), 816.49 (s), 786.63 (s) cm$^{-1}$.

Anal. Calcd for C$_{12}$H$_{18}$N$_2$O$_7$S$_2$.CH$_4$O$_3$S: C, 33.76; H, 4.79; N, 6.06. Found: C, 33.98; H, 4.82; N, 5.98.

EXAMPLE 44

(1R,2S,5R,6R)-2-(2'R-aminopropionyl)amino-6-fluoro-bicyclo[3.1.0]hexane-2,6-dicarboxylic acid hydrochloride

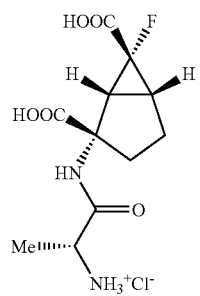

Add 1.13 mL (2.8 mmol) of 2.5 N LiOH to a solution of 0.20 g (0.47 mmol) of Isomer A from Preparation 60 in THF (1.2 mL) and stir the resulting mixture overnight at room temperature. Wash the solution with ether, neutralize at 0° C. with 1N HCl, and extract with EtOAc (3×3 mL). Dry the combined organic layers over anhydrous $MgSO_4$ and concentrate under reduced pressure. Dissolve the crude in 3.76 mL of 1N HCl in EtOAc and stir overnight. Decant the solvent, wash with ether, and dry the product with an Ar stream to give the title compound (83 mg, 57% yield) as a white solid.

$^1$H-NMR (300 MHz, $CDCl_3$): 1.28 (d, 3H, J=7.1 Hz), 1.64-1.69 (m, 1H), 1.86-2.02 (m, 1H), 2.11-2.21 (m, 3H), 2.54 (d, 1H, J=7.1 Hz), 3.84 (q, 1H, J=7.1 Hz).

EXAMPLE 45

(1S,2R,5S,6S)-2-(2'R-aminopropionyl)amino-6-fluoro-bicyclo[3.1.0]hexane-2,6-dicarboxylic acid hydrochloride

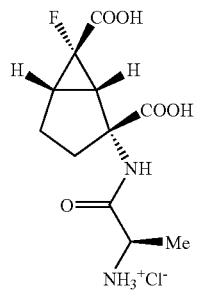

Beginning with a solution Isomer B of Preparation 60, the title compound is prepared essentially as Example 44.

$^1$H-NMR (300 MHz, $CDCl_3$): 1.30 (d, 3H, J=7.1 Hz), 1.59-1.65 (m, 1H), 1.85-2.03 (m, 1H), 2.05-2.25 (m, 3H), 2.53 (d, 1H, J=6.6 Hz), 3.85 (q, 1H, J=7.1 Hz).

EXAMPLE 46

(1S,2S,4S,5R,6R)-2-(2'S-aminopropionyl)amino-4-hydroxy-bicyclo[3.1.0]hexane-2,6-dicarboxylic acid hydrochloride

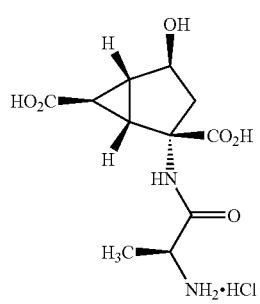

Prepare according to General Procedure C using (1S,2S,4S,5R,6R)-2-(2'S-tert-butoxycarbonylamino-propionylamino)-4-hydroxy-bicyclo[3.1.0]hexane-2,6-dicarboxylic acid diethyl ester (0.47 g, 1.1 mmol, Preparation 37) to yield 0.23 g (67.7%) of the title compound.

$[\alpha]_D^{23}$=-4.1 (c=0.49, MeOH).

$^1$H NMR ($CD_3OD$) δ 1.51 (3H, d, J=7.0 Hz), 1.56 (1H, t, J=2.9 Hz), 1.77 (1H, dd, J=5.8, 15.8 Hz), 2.1-2.13 (1H, m), 2.52 (1H, d, J=16.1 Hz), 2.57 (1H, dd, J=2.9, 5.9 Hz), 3.88 (1H, dd, J=7.0, 14.3 Hz), 4.32 (1H, d, J=5.5 Hz).

Anal. Calcd for $C_{11}H_{17}N_2O_6 \cdot 1.1HCl \cdot 0.9H_2O$: C, 40.12; H, 5.80; N, 8.53. Found: C, 39.85; H, 5.41; N, 8.36.

HRMS calcd for $C_{11}H_{16}N_2O_6Na$, 295.0906. Found, 295.0883.

Prodrug compounds of the present invention may be evaluated against the corresponding parent compound through various cellular uptake assays. These assays can provide comparative data to permit one of ordinary skill in the art to identify compounds which are readily absorbed into the cell to provide superior exposure. Two such assays include the Gly-Sar Uptake Assay and the Caco-2 Assay, described below.

Gly-Sar Uptake Assay

It has been realized that some orally administered peptidomimetic drugs are absorbed through the intestinal peptide transport system. Yang et al., Pharm. Res. 16(9) (1999). In particular, the intestinal peptide transporter hPepT1 has been studied for its expression of inhibition of peptidyl uptake and its corresponding level of recognition within a cell. Meredith, et al., Eur. J. Biochem., 267, 3723-3728 (2000). Further, characterizing the intestinal absorption mechanism of amino acids in the hPepT1 transporter has been targeted as an effective strategy for identifying improved oral drug absorptions. Han, et al., Polym. Prepr. (Am. Chem. Soc., Div. Polym. Chem.) 40(1): 259-260 (1999); Sawada, et al., J. Pharmacol. Exp. Ther., 291(2): 705-709 (1999).

U.S. Pat. No. 5,849,525 describes methods which could be used to measure the level of affinity of compounds of the present invention with the hPepT1 transporter.

For example, stably transfected Chinese Hamster Ovary (CHO) cells over-expressing the hPepT1 transporter could be used to test compounds of the present invention. The CHO cells would monitored for the uptake of Gly-Sar, which when uptake in the presence of the prodrug compounds of the present invention is in amounts greater than when the cell is free from prodrug compounds of the present invention would be indicative of agonist activity; and which when uptake of the prodrug compounds of the present invention is less than the uptake in the absence of prodrug compounds of the present invention would be indicative of inhibitory activity. Compounds of the present invention generally exhibit $EC_{50}$ values of less than 5 mM.

Caco-2 Assay

Another particular method for measuring the uptake of compounds of the present invention into cells is to study the peptide transport carrier of human intestinal cell line Caco-2. Human adenocarcinoma cells (Memorial Sloan-Kettering Cancer Center, Rye, N.Y., and/or ATCC, Rockville, Md.) are passaged in Dulbecco's Modified Eagle medium containing 10% fetal calf serum and 1% Minimal Essential Media non-essential amino acid solution without addition of sodium pyruvate or antibiotics. These cells were mycoplasma-free and were used between passage numbers 28 and 40. For flux measurements, between 5 to $10 \times 10^4$ cells are grown in collagen-coated multiwell dishes for 13-18 days and the medium is replaced every two to three days.

Drug uptake is measured at 37° C. using a test compound employing a cluster-tray technique (see Gazzola, et al., Anal. Biochem. 115, 368-74 (1981)). The flux buffer is bicarbonate-free Earle's balanced salt solution containing 25 mM Mes titrated to pH 6.0 with KOH, and choline chloride in place of sodium chloride. The osmolality of the flux buffer is adjusted to 300±5 mosmol/kg with choline chloride. [$^3$H]Inulin is used as a marker for the extracellular fluid that adheres to cells during the washing procedure to estimate the zero time for determining the rate of uptake. Fresh solutions of the test compounds and dipeptides are prepared daily. At the end of the experiment cells, are lysed in water, test compounds can be detected in cell lysates using LC/MS/MS. Protein is measured by the method described in Smith, et al., Anal. Biochem. 150, 76-85 (1985).

Uptake is measured over a 40 minute. Initial uptake rates are calculated in the linear region of the time course regression and an estimated zero time as described above using linear regression. Percent inhibition is calculated based on the control uptake rate measured in the absence of a dipeptide. For examples of this Caco-2 assay, see Dantzig & Bergin, Biochim. Biophys. Acta 1027, 211-17 (1990).

In Vivo Exposure as Measured by Rat Plasma Concentration

To study the in vivo exposure of compounds of Formula II following oral dosing of compounds of Formula I in comparison to compounds of Formula II, studies measuring the plasma concentrations of the respective compound of Formula II in rats are performed. Mature Fischer 344 male rats (190-270 gram) are obtained from Harlan Sprague-Dawley, Cumberland, Ind., USA, and acclimated in the study housing for 3 days. On day 4, test compounds are dissolved in buffered water (1 mg/ml=test compound/20 mM potassium dihydrogen phosphate, pH=2) and given orally as a single 5 mg/kg dose. Blood samples are collected through orbital sinus or cardiac puncture (last time point) at 0.5 and 1 hour or, alternatively, at 1 and 3 hours. Plasma samples are stored at −20° C. in the presence of phenylmethylsulfonyl fluoride, a protease inhibitor, prior to analysis. Plasma samples and internal standard compounds are pretreated by solid phase extraction (SAX support, methanol/water/dilute acetic acid).

As shown in Tables 1A and 1B below, the plasma concentrations (ng/ml) of the respective compound of Formula II for each test compound are determined by LC/MS/MS and are presented as a sum of the concentrations at the 0.5 and 1 hour or, alternatively, at the 1 and 3 hour sample time points.

TABLE 1A

In Vivo Exposure Assay

| Compound | Rat Exposure (ng/ml of (1R,4S,5S,6S)-4-(2'S-Aminopropionyl)amino-]-2,2-dioxo-2λ$^6$-thiabicyclo[3.1.0.]hexane-4,6-dicarboxylic acid hydrochloride) |
|---|---|
| Example 1 | 2251 ng/ml (following 10 mg/kg p.o.) |
| Non-prodrug form of Example 1 | 1521 ng/ml (following 5 mg/kg p.o.) |
|  | 3981 ng/ml (following 10 mg/kg p.o.) |

TABLE 1B

In Vivo Exposure Assay

| Compound | Rat Exposure (ng/ml of (1R,2S,4R,5R,6R)-2-(2'S-Aminopropionyl)amino-4-fluorobicyclo[3.1.0]hexane-2,6-dicarboxylic acid hydrochloride) |
|---|---|
| Example 14 | 5271 ng/ml (following 5 mg/kg p.o.) |
| Non-prodrug form of Example 14 | 1162 ng/ml (following 5 mg/kg p.o.) |
|  | 1342 ng/ml (following 10 mg/kg p.o.) |

As shown above in Tables 1A and 1B, when given orally to rats, the compounds of the current invention exhibit comparable plasma concentration of the parent compound. This demonstrates compounds of the present invention are converted to the parent compounds, compounds of Formula II, in vivo.

The compounds of the present invention are preferably formulated prior to administration. Therefore, another aspect of the present invention is a pharmaceutical formulation comprising a compound of Formula I, or a pharmaceutically acceptable salt thereof, and a pharmaceutically-acceptable carrier, diluent, or excipient. The pharmaceutical formulations may be prepared by procedures well-known by one of ordinary skill in the art. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well-known in the art.

The compositions are preferably formulated in a unit dosage form, each dosage containing from about 5 mg to about 500 mg active ingredient, preferably about 25 mg to about 300 mg active ingredient. As used herein the term "active ingredient" refers to a compound included within the scope of Formula I.

The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient.

The invention claimed is:

1. A compound of Formula I

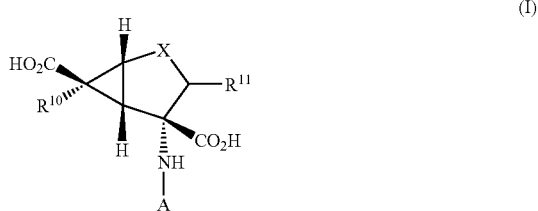

wherein:

A is H-(Q)p-;

Q is independently selected, each time taken from the group amino acyl derived from an amino acid selected from the group consisting of:

natural amino acids and unnatural amino acids selected from the D-isomers of the natural α-amino acids; Aib (aminobutyric acid), βAib (3-aminoisobutyric acid), Nva (norvaline), β-Ala, Aad (2-aminoadipic acid), βAad (3-aminoadipic acid), Abu (2-aminobutyric acid), Gaba (γ-aminobutyric acid), Acp (6-aminocaproic acid), Dbu (2,4-diaminobutryic acid), α-aminopimelic acid, TMSA (trimethylsilyl-Ala), aIle (allo-isoleucine), Nle (norleucine), tert-Leu, Cit (citrulline), Orn, Dpm (2,2'-diaminopimelic acid), Dpr (2,3-diaminopropionic acid), α- or β-Nal, Cha (cyclohexyl-Ala), hydroxyproline, Sar (sarcosine), O-methyl tyrosine, phenyl glycine, MeGly ($N^\alpha$-methylglycine), EtGly ($N^\alpha$-ethylglycine), and EtAsn ($N^\alpha$-ethylasparagine);

p is an integer from 1 to 10;

X is $SO_2$;

$R^{10}$ is hydrogen or fluoro; and $R^{11}$ is hydrogen, fluoro, or hydroxy;

or a pharmaceutically acceptable salt thereof.

2. The compound according to claim 1 wherein p is an integer from 1 to 3.

3. The compound according to claim 1 wherein p is 1.

4. The compound according to claim 3 wherein Q is an amino acyl derived from a natural amino acid.

5. A compound of Formula I

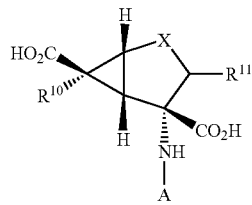

(I)

wherein:

A is H-(Q)p-;

Q is glycyl, alanyl, valyl, leucyl, isoleucyl, prolyl, phenylalanyl, tyrosyl, tryptophyl, methionyl, lysyl, or serinyl;

p is an integer from 1 to 10;

X is $SO_2$;

$R^{10}$ is hydrogen or fluoro; and $R^{11}$ is hydrogen, fluoro, or hydroxy;

or a pharmaceutically acceptable salt thereof.

6. The compound according to claim 5 wherein p is an integer from 1 to 3.

7. The compound according to claim 5 wherein p is 1.

8. The compound according to claim 7 wherein Q is methionyl.

9. The compound according to claim 8 wherein $R^{10}$ is hydrogen.

10. The compound according to claim 9 wherein $R^{11}$ is hydrogen.

11. A pharmaceutically acceptable salt according to claim 1 that is an acid-addition salt made with an acid which provides a pharmaceutically acceptable anion; a base-addition salt made with a base which provides a pharmaceutically acceptable anion for a compound which contains an acidic moiety; or a zwitterionic compound which contains oppositely charged groups.

12. The compound according to claim 1 wherein

A is H-(Q)$_p$-;

Q is L-alanyl;

p is 1;

X is $SO_2$;

$R^{10}$ hydrogen; and $R^{11}$ hydrogen;

or the hydrochloride salt, tosylate salt, mesylate salt, esylate salt, besylate salt, or monosodium salt thereof.

13. The compound according to claim 12 which is (1R,4S,5S,6S)-4-(2'S-Aminopropionyl)amino]-2,2-dioxo-2$\lambda^6$-thia-bicyclo[3.1.0.]hexane-4,6-dicarboxylic acid hydrochloride or (1R,4S,5S,6S)-4-(2'S-2'-Aminopropionyl)amino-2,2-dioxo-2$\lambda^6$-thia-bicyclo[3.1.0.]hexane-4,6-dicarboxylic acid tosylate.

14. A process for preparing a compound of Formula I, or a pharmaceutically acceptable salt thereof, as claimed in claim 1 comprising acylating a compound of formula (ii)

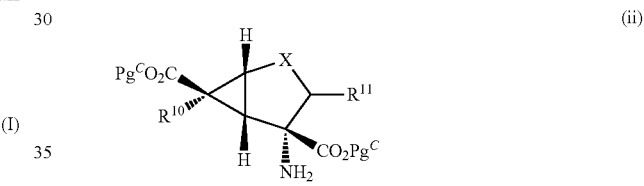

(ii)

with a corresponding amino acyl of Formula III $Pg^N$-A-  (III)

wherein $Pg^N$ is a nitrogen-protecting group;

whereafter, for any of the above procedures, when a functional group is protected using a protecting group, removing the protecting group;

whereafter, for any of the above procedures: when a pharmaceutically acceptable salt of a compound of Formula I is required, reacting the basic form of such a compound of Formula I with an acid affording a pharmaceutically acceptable counterion; or for a compound of Formula I which bears an acidic moiety, reacting the acidic form of such a compound of Formula I with a base which affords a pharmaceutically acceptable cation; or for a zwitterionic compound of Formula I, neutralizing the acid-addition salt form or base-addition salt form of such a compound of Formula I.

15. A pharmaceutical formulation comprising in association with a pharmaceutically acceptable carrier, diluent or excipient, the compound according to claim 1.

* * * * *